US 7,759,315 B2

(12) United States Patent
Cuzzocrea et al.

(10) Patent No.: US 7,759,315 B2
(45) Date of Patent: Jul. 20, 2010

(54) TREATMENT OF INFLAMMATORY CONDITIONS OF THE INTESTINE

(75) Inventors: Salvatore Cuzzocrea, Messina (IT); Christoph Thiemermann, Essex (GB); Gillian Cockerill, London (GB)

(73) Assignee: CSL Behring AG, Bern (CH)

( * ) Notice: Subject to any disclaimer, the term of this patent is extended or adjusted under 35 U.S.C. 154(b) by 600 days.

(21) Appl. No.: 11/074,723

(22) Filed: Mar. 9, 2005

(65) Prior Publication Data
US 2006/0205643 A1    Sep. 14, 2006

(51) Int. Cl.
*A61K 38/00* (2006.01)
*C07K 1/00* (2006.01)

(52) U.S. Cl. .................. 514/21; 530/359; 530/326
(58) Field of Classification Search .................. None
See application file for complete search history.

(56) References Cited

U.S. PATENT DOCUMENTS

| 5,652,339 | A |   | 7/1997 | Lerch et al. |
| 5,780,592 | A | * | 7/1998 | Mullner et al. ............. 530/359 |
| 6,559,284 | B1 |  | 5/2003 | Ageland et al. |
| 6,998,388 | B1 | * | 2/2006 | Cockerill et al. ............. 514/21 |

FOREIGN PATENT DOCUMENTS

| WO | WO-87/02062 A1 |   | 9/1987 |
| WO | WO-88/03166 A1 |   | 5/1988 |
| WO | WO-90/12879 A2 |   | 1/1990 |
| WO | WO-99/16408 A2 |   | 4/1999 |
| WO | WO-99/16459 A1 |   | 4/1999 |
| WO | WO 01/13939 | * | 3/2001 |

OTHER PUBLICATIONS

Wells, 1990, Biochemistry 29:8509-8517.*
Ngo et al., 1994, The Protein Folding Problem and Tertiary Structure Prediction, pp. 492-495.*
Cuzzocrea et al. 2004. Shock 21:342-351.*
Hoffmann et al. 2002. Pathobiology 70:121-130.*
Nayar et al. 2004. Postgrad Med J. 80:206-213.*
Cotran et al. 1999. Pathologic Basis of Disease, 6th edition.*
Cockerill G.W. et al.; International Review of Cytology, vol. 188, pp. 257-297 (1999).
Nanjee, M. N. et al., Arterioscier Thromb Vasc Biol., vol. 19, pp. 979-989 (1999).
Gordon, David J. et al.; Circulation, vol. 79, pp. 8-15 (1989).
Paszty, Chris et al.; J. Clin. Invest., vol. 94, pp. 899-903 (1994).
Tangirala, Rajendra K. et al.; Circulation, vol. 100, pp. 1816-1822 (1999).
McDonald, Michelle C. et al.; Shock, vol. 20, No. 6, pp. 551-557 (2003).
Cockerill, Gillian W. et al.; FASEB J., vol. 15, pp. 1941-1952 (2001).
van Leeuwen, Henk J. et al.; Neth. J. Med., vol. 59, pp. 102-110 (2001).
Cockerill, Gillian W. et al.; Circulation, vol. 103, pp. 108-112 (2001).
Pajkrt, D. et al.; J. Exp. Med., vol. 184, pp. 1601-1608 (1996).
Thiemermann, Christoph et al.; J. Am. Soc. Nephrol., vol. 14, pp. 1833-1843 (2003).
Cuzzocrea, Salvatore et al.; Pharmacol. Rev., vol. 53, pp. 135-159 (2001).
Cuzzocrea, Salvatore et al.; Shock, vol. 18, No. 2, pp. 169-176 (2002).
Cuzzocrea, Salvatore et al.; Eur. J. Pharmacol., vol. 432, pp. 79-89 (2001).
Parks, Dale A.; Gut, vol. 30, pp. 293-298 (1989).
Mahida, Y.R. et al.; Gut, vol. 30, pp. 1362-1370 (1989).
Verspaget, H.W. et al.; Gut, vol. 29, pp. 223-228 (1988).
Crama-Bohbouth, G.E. et al.; Digestion, vol. 40, pp. 227-236 (1988).
Grisham, M.B. et al.; Digestive Disease & Sciences, vol. 33, No. 3, pp. 6S:15S (1988).
Butcher, E.C. ; Res. Immunol., vol. 144, pp. 695-698 (1993).
Wertheimer, S. J. et al.; J. Biol. Chem.; vol. 267, No .17, pp. 12030-12035 (1992).
Wallace, J.L. et al.; Gastroenterology, vol. 102, pp. 18-27 (1992).
Matz, C.E. et al.; J. Biol. Chem.; vol. 257, pp. 4535-4540 (1982).
Lerch, P.G. et al.; Vox Sang, vol. 71, pp. 155-164 (1996).
Chang et al., "Clindamycin-Induced Enterocolitis in Hamsters as a Model of Pseudomembranous Colitis in Patients," *Infection and Immunity*, May 1978, pp. 526-529, vol. 20, No. 2, American Society for Microbiology, USA.
Elmer et al., "Suppression by *Saccharomyces boulardii* of Toxigenic *Clostridium difficile* Overgrowth after Vancomycin Treatment in Hamsters," *Antimicrobial Agents and Chemotherapy*, Jan. 1987, pp. 129-131, vol. 31, No. 1, American Society for Microbiology, USA.
Fukuda et al., "Prebiotic treatment of experimental colitis with germinated barley foodstuff: A comparison with probiotic or antibiotic treatment," *International Journal of Molecular Medicine*, 2002, pp. 65-70, vol. 9.
Kitahora et al., "Active Oxygen Species Generated by Monocytes and Polymorphonuclear Cells in Crohn's Disease," *Digestive Diseases and Sciences*, Aug. 1988, pp. 951-955, vol. 33, No. 8, Plenum Publishing Corporation.
Jul. 13, 2007 Email from publication coordinator at *Shock Journal*.
Jewell, D.P., Chapter 14.10 "Crohn's disease," and Chapter 14.11 "Ulcerative Colitis," *Oxford Textbook of Medicine*, 4th Edition, pp. 604-613, 612-613, vol. 2: Sections 11-17, Warrell et al. (Eds.), Oxford University Press, 2003.
Jouret-Mourin et al., "Colites infectieuses," *Acta Endoscopica*, 2002, pp. 167-183, vol. 32, No. 2.
*Stedman's Medical Dictionary*, 23rd Edition, 1976, pp. 725 and 1279, Williams & Wilkins, Baltimore/London.
Surawicz et al., "Pseudomembranous Colitis: Causes and Cures," *Digestion*, 1999, pp. 91-100, vol. 60.

\* cited by examiner

*Primary Examiner*—Gary B. Nickol
*Assistant Examiner*—Shulamith H Shafer
(74) *Attorney, Agent, or Firm*—Foley & Lardner LLP

(57) ABSTRACT

A method for the treatment and/or prophylaxis of an inflammatory condition of the intestine of a patient, comprises parenteral administration to the patient of an effective amount of high density lipoprotein (HDL).

16 Claims, 13 Drawing Sheets

TREATMENT OF INFLAMMATORY CONDITIONS OF THE INTESTINE

FIELD OF THE INVENTION

This invention relates generally to a method for the treatment and/or prophylaxis of inflammatory conditions of the intestine, including but not limited to inflammation and inflammatory damage associated with ischaemia/reperfusion injury of the intestine, inflammatory bowel disease and colitis. More particularly, the present invention relates to the use of high density lipoproteins (HDLs) in the treatment and/or prophylaxis of these inflammatory conditions of the intestine.

BACKGROUND OF THE INVENTION

Bibliographic details of the publications referred to in this specification are referenced at the end of the description. The reference to any prior art document in the specification is not, and should not be taken as, an acknowledgment or any form of suggestion that the document forms part of the common general knowledge in Australia.

High-density lipoproteins (HDLs) represent a broad group of mostly spheroidal plasma lipoproteins, which exhibit considerable diversity in their size, apolipoprotein (apo) and lipid composition. HDL particles fall into the density range of 1.063-1.21 g/ml (1) and as they are smaller than other lipoproteins, HDLs can penetrate between endothelial cells more readily allowing relatively high concentrations to accumulate in tissue fluids (2). The major apolipoprotein of almost all plasma HDLs is apo A-1, which in association with phospholipids and cholesterol, encloses a core of cholesteryl esters (1). Nascent (i.e. newly synthesised) HDLs secreted by the liver and intestine contain no cholesteryl esters and are discoidal in shape (1). The negative association of plasma HDL concentration with coronary artery disease has been well documented in epidemiological studies (3). Although experiments in animals have demonstrated an anti-atherogenic activity of HDLs (4), it is not yet known whether this protective effect is related to the role of the lipoprotein in reverse cholesterol transport or to a different mechanism. The mechanism/mechanisms via which HDLs provide these cardioprotective actions are not clearly understood, but may include a role for HDLs in reverse transport of cholesterol from peripheral tissues to the liver, inhibition of the oxidation of low-density lipoproteins, or modulation of vasodilatation and platelet activation mediated by changes in the production of prostacyclin (5). HDLs can also activate endothelial nitric oxide synthase subsequent to its interaction with scavenger receptor-B1 (SR-B1). Although HDLs are involved in the removal of cholesterol from extra-hepatic tissues, this subset of lipoproteins has recently been reported to possess functions unrelated to their role in plasma cholesterol transport. Almost 10 years ago, it was reported that in transgenic mice in which plasma levels of HDL were two-fold higher, the increase in plasma levels of TNF-α as well as mortality caused by bacterial lipopolysaccharide (LPS) were significantly reduced (6). Subsequently, it has been demonstrated that administration of native HDL or reconstituted HDL (=recHDL) significantly reduces organ injury and levels of mortality in animal models of endotoxic (LPS-mediated) and haemorrhagic shock (7). The beneficial actions observed in these models are—at least in part—mediated by the ability of HDLs to bind and inactivate LPS (6,8), directly inhibit expression of adhesion molecules on endothelial cells and via modulation of the expression of proinflammatory cytokines (6,9). In human volunteers, systemic administration of HDLs also downregulates the LPS ligand CD14 on monocytes and attenuates the release of TNF-α, IL-6 and IL-8 caused by small doses of intravenously administered LPS (10). HDL has also been shown to directly inhibit the TNF-α-induced expression of P-selectin on human endothelial cells (6). In addition, it has been reported that HDLs reduces the renal injury, dysfunction and inflammation caused by bilateral renal artery occlusion and reperfusion in the rat (11).

A growing body of data indicates that oxygen-derived free radicals such as superoxide ($O_2^-$), nitric oxide (NO) and hydroxyl radicals ($OH^-$) have a role in mediating the intestinal damage in ischaemia/reperfusion [I/R] (12,13) as well as in inflammatory bowel disease (IBD) (14). The intestine is well endowed with enzymes capable of producing such free radicals (15). Moreover, when inflammation is present the many phagocytic cells that are attracted and activated can produce large amounts of free radicals. Several studies suggest that peripheral blood monocytes (16), and isolated intestinal macrophages (17), from patients with IBD produce increased amounts of free radicals. Also high numbers of peripheral polymorphonuclear leukocytes (PMNs), which are capable of producing large amounts of oxygen-derived free radicals (18), migrate into the intestinal wall of such patients (19). Grisham and Granger (20) hypothesised that—like in I/R injury—in ulcerative colitis transient ischaemic and subsequent reperfusion produce high levels of free radicals. This process initiates a cascade of events leading to the recruitment and activation of PMNs. In the last few years, various studies have gained substantial insight into the importance of specific adhesion molecules and mediators in processes, which finally result in the recruitment of PMNs at a specific site of inflammation. Activated PMNs, therefore, play a crucial role in the destruction of foreign antigens and the breakdown and remodelling of injured tissue. PMN-endothelial interactions involve a complex interplay among adhesion glycoproteins (i.e. integrins, members of the immunoglobulin superfamily and selectins). The firm adhesion of PMNs to the endothelium, however, is a complex phenomenon, which also involves other endothelium-based adhesion molecules. In fact, endothelial adhesion molecules are considered to play a pivotal role in the localisation and development of an inflammatory reaction (21). Intercellular adhesion molecule-1 (ICAM-1) is an adhesion molecule normally expressed at a low basal level, but its expression can be enhanced by various inflammatory mediators such as TNF-α and IL-1β (22).

Models of splanchnic artery occlusion shock (SAO) and 2,4,6-dinitrobenzene-sulfonic acid (DNBS)-induced colitis have been widely employed to investigate the pathophysiology of intestinal damage associated with I/R and with IBD. In work leading to the present invention, the inventors have investigated whether recHDL reduces the intestinal injury and inflammation caused by SAO shock and the chronic inflammatory response (colitis) caused by injection of DNBS in the rat. In order to highlight the possible mechanisms through which HDLs confer protection, the following end-points of the inflammatory response have been determined: (1) PMN infiltration (determined as myeloperoxidase [MPO] activity, (2) pro-inflammatory cytokine production, (3) expression of adhesion molecules (i.e. ICAM-1), (4) lipid peroxidation (evaluated as malondialdehyde [MDA] levels) (5) peroxynitrite formation, (6) activation of the nuclear enzyme poly (ADP-ribose) (PAR) polymerase (PARP) and (7) morphological changes in the intestine.

SUMMARY OF THE INVENTION

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

In one aspect, the present invention provides a method for the treatment and/or prophylaxis of an inflammatory condition of the intestine of a patient, which comprises parenteral administration to the patient of an effective amount of high density lipoprotein (HDL).

In another aspect, the present invention provides the use of high density lipoprotein (HDL) in the manufacture of a medicament for parenteral administration to a patient for the treatment and/or prophylaxis of an inflammatory condition of the intestine of the patient.

In yet another aspect, the invention provides an agent for parenteral administration in the treatment and/or prophylaxis of an inflammatory condition of the intestine of a patient, which comprises high density lipoprotein (HDL).

DETAILED DESCRIPTION OF THE INVENTION

Figure 1:
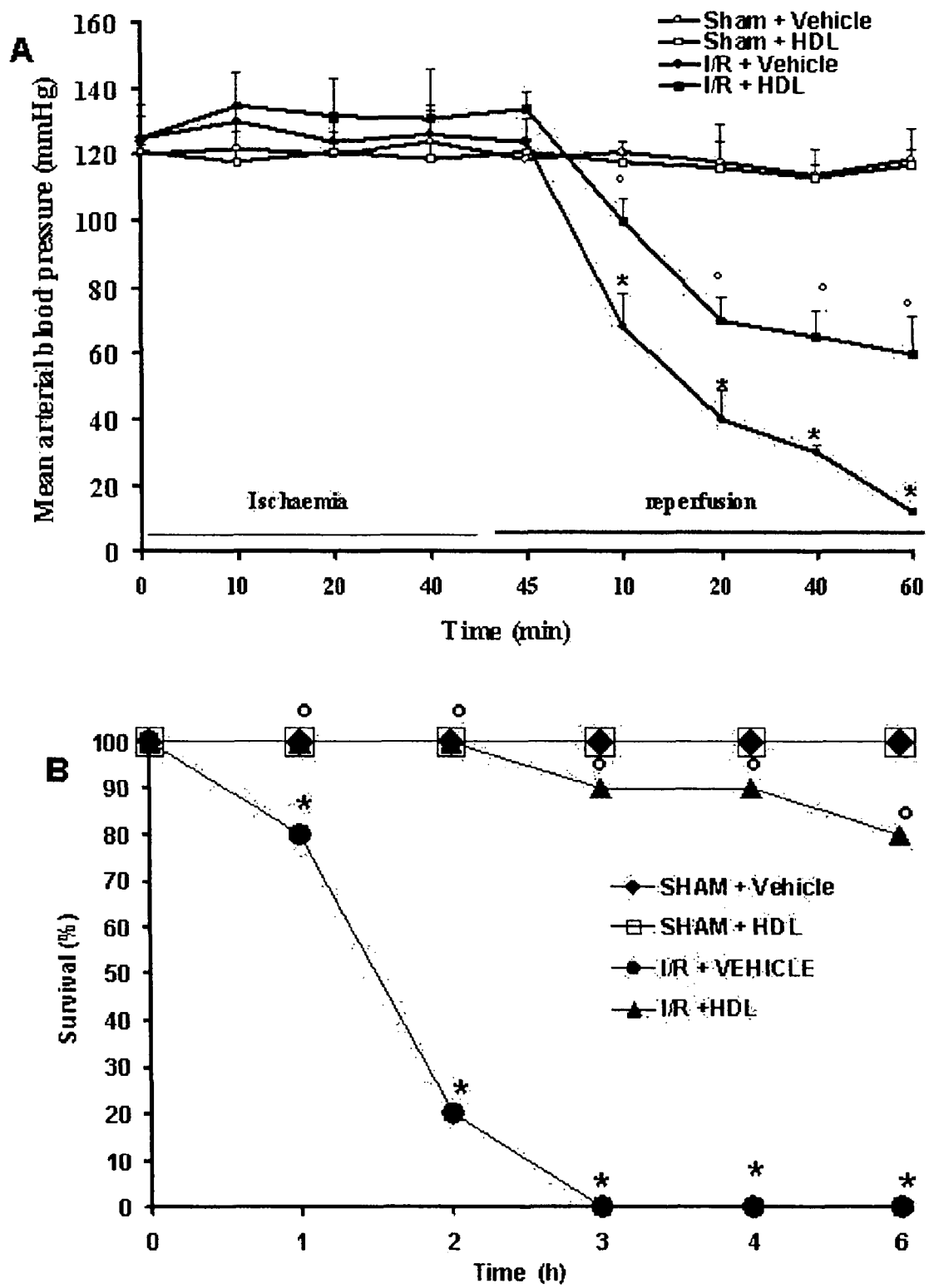
FIG. 1 shows the effect of HDL treatment on mean blood pressure and survival. Effect of HDL treatment on MAP (A) and mortality (B). No significant alteration of MAP was observed in sham-operated rats. Fall in MAP and the mortality in SAO rats was significantly reduced by HDL treatment (80 mg/kg). Values are means±S.E.M. of 10 rats for each group. *P<0.01 versus sham, °P<0.01 versus I/R.

High-density lipoproteins (HDLs) have been shown to reduce the organ injury and mortality in animal models of shock by reducing the expression of adhesion molecules and pro-inflammatory enzymes. However, there is limited evidence that HDL treatment reduces inflammation. As inflammation plays an important role in the development of colitis as well as ischaemia/reperfusion (I/R) injury of the intestine, the inventors have investigated the effects of HDL in animal models associated with gut injury and inflammation [splanchnic artery occlusion (SAO) shock and dinitrobenzene sulfonic acid (DNBS) induced colitis], and shown that the administration of reconstituted HDL (recHDL) (80 mg/kg i.v. bolus 30 min prior ischaemia in the SAO-shock model or 40 mg/kg i.v. every 24 h in the colitis model) exerts potent anti-inflammatory effects (e.g. reduced inflammatory cell infiltration and histological injury, and delayed the development of the clinical signs) in vivo. Furthermore, recHDL reduced (i) the staining for nitrotyrosine and poly (ADP-ribose) (immunohistochemistry) and; (ii) the expression of intercellular adhesion molecule-1 in the ileum of SAO-shocked rats and in the colon from DNBS-treated rats. Thus, recHDL reduces the inflammation caused by intestinal I/R and colitis.

In one aspect, the present invention provides a method for the treatment and/or prophylaxis of an inflammatory condition of the intestine of a patient, which comprises parenteral administration to the patient of an effective amount of high density lipoprotein (HDL).

Reference herein to "treatment" or "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Inflammatory conditions of the intestine to which the present invention relates include, but are not limited to, inflammation and inflammatory damage associated with ischaemia/reperfusion (I/R) injury of the intestine, inflammatory bowel disease (including Crohn's disease and ulcerative colitis), acute infective colitis, and pseudomembranous colitis (an antibiotic-induced condition caused by Clostridium overgrowth). Such diseases are described in relevant standard textbooks which include Harrison's Principles of Internal Medicine, Oxford Textbook of Medicine, and Principles and Practice of Gastroenterology and Hepatology.

In accordance with the present invention, HDL is administered to a patient. The term "HDL" as used herein relates to all forms of high density lipoproteins and includes nascent HDL or reconstituted HDL (RHDL) or any mixture thereof, as well as recombinant HDL or an analogue thereof with functional relationship to nascent or reconstituted HDL. Such analogues include functional peptides derived from the apolipoprotein (Apo) structure such as those described in International Patent Publications Nos. WO 99/16459 and WO 99/16408, the contents of which are incorporated herein by reference For example: (i) a 22 to 29 or 15 to 26-residue peptide or peptide analogue which forms an amphipathic α helix in the presence of lipids and which comprises formula (I):

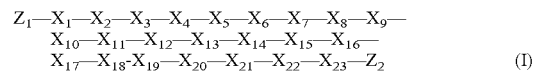

(I)

or a pharmaceutically acceptable salt thereof, wherein:

$X_1$ is Pro (P), Ala (A), Gly (G), Gln (Q), Asn (N), Asp (D) or D-Pro (p);

$X_2$ is an aliphatic residue;

$X_3$ is Leu (L) or Phe (F);

$X_4$ is an acidic residue;

$X_5$ is Leu (L) or Phe (F);

$X_6$ is Leu (L) or Phe (F);

$X_7$ is a hydrophilic residue;

$X_8$ is an acidic or a basic residue;

$X_9$ is Leu (L) or Gly (G);

$X_{10}$ is Leu (L), Trp (W) or Gly (G);

$X_{11}$ is a hydrophilic residue;

$X_{12}$ is a hydrophilic residue;

$X_{13}$ is Gly (G) or an aliphatic residue;

$X_{14}$ is Leu (L), Trp (W), Gly (G) or NaI:

$X_{15}$ is a hydrophilic residue;

$X_{16}$ is a hydrophobic residue;

$X_{17}$ is a hydrophobic residue;

$X_{18}$ is Gln (O), Asn (N) or a basic residue;

$X_{19}$ is Gln (O), Asn (N) or a basic residue;

$X_{20}$ is a basic residue;

$X_{21}$ is an aliphatic residue;

$X_{22}$ is a basic residue;

$X_{23}$ is absent or a basic residue;

$Z_1$ is $H_2N$— or RC(O)NH—;

$Z_2$ is —C(O)NRR, —C(O)OR or —C(O)OH or a salt thereof;

each R is independently —H, ($C_1$-$C_6$) alkyl, ($C_1$-$C_6$) alkenyl, ($C_1$-$C_6$) alkenyl, ($C_5$-$C_{20}$) aryl, ($C_6$-$C_{26}$) alkaryl, 5-20 membered heteroaryl, 6-26 membered alkheteroaryl or a 1 to 4-residue peptide or peptide analogue in which one or more bonds between residues 1-4 or 1-7 are independently a substituted amide, an isotere of an amide or an amide mimetic; and each "—" between residues $X_1$ through $X_{23}$ independently designates an amide linkage, a substituted amide linkage, an isotere of an amide or an amide mimetic; or (ii) an altered form of formula (I) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$ is conservatively substituted with another residue.

In another example: (1) a 15 to 22 or 18 to 22-residue peptide or peptide analogue which forms an amphipathic α helix in the presence of lipids and which comprises formula (II):

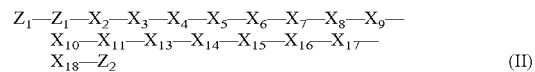

(II)

or a pharmaceutically acceptable salt thereof, wherein:

$X_1$ is Pro (P), Ala (A), Gly (G), Gln (O), Asn (N), or D-Pro (p);

$X_2$ is an aliphatic amino acid;

$X_3$ is Leu (L);

$X_4$ is an acidic amino acid;

$X_5$ is Leu (L) or Phe (F);

$X_6$ is Leu (L) or Phe (F);

$X_7$ is a basic amino acid;

$X_8$ is an acidic amino acid;

$X_9$ is Leu (L) or Trp (W);

$X_{10}$ is Leu (L) or Trp (W);

$X_{11}$ is an acidic amino acid or Asn (N);

$X_{12}$ is an acidic amino acid;

$X_{13}$ is Leu (L), Trp (W) or Phe (F);

$X_{14}$ is a basic amino acid or Leu (L);

$X_{15}$ is Gln (O) or Asn (N);

$X_{16}$ is a basic amino acid;

$X_{17}$ is a Leu (L);

$X_{18}$ is a basic amino acid;

$Z_1$ is $H_2N$— or RC(O)NH—;

$Z_2$ is —C(O)NRR, —C(O)OR or —C(O)OH or a salt thereof;

each R is independently —H, $(C_1$-$C_6)$ alkyl, $(C_1$-$C_6)$ alkenyl, $(C_1$-$C_6)$ alkynyl, $(C_5$-$C_{20})$ aryl, $(C_6$-$C_6)$ alkaryl, 5-20 membered heteroaryl, 6-26 membered alkheteroaryl or a 1-4-residue peptide or peptide analogue in which, optionally, one or more bonds between residues 1-4 or 1-7 are independently a substituted amide, an isotere of an amide or an amide mimetic; each "—" between residues $X_1$ through $X_{18}$ independently designates an amide linkage, a substituted amide linkage, an isotere of an amide or an amide mimetic; and optionally, at least one L-enantiomeric residue of formula (II) other than Pro (P) at $X_1$ is replaced with an identical D-enantiomeric residue; or (ii) an altered form of formula (II) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, or $X_{18}$ is conservatively substituted with another residue; or (iii) an altered for of formula (II) in which up to eight of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, or $X_{18}$ are optionally deleted or a 14 to 21-residue deleted peptide or peptide analogue according to formula (II) in which at least one and up to eight of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, or $X_{18}$ are optionally deleted and wherein at least one remaining L-enantiomeric residue of formula (II) is replaced with an identical D-enantiomeric residue; or (iv) an 18 to 22-residue altered peptide or peptide analogue according to formula (II) in which at least one and up to eight of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, or $X_{18}$ is conservatively substituted and wherein at least one L-enantiomeric residue of the resulting altered peptide or peptide analogue is replaced with an identical D-enantiomeric residue; or an N-terminally blocked form, a C-terminally blocked form, or an N- and C-terminally blocked form of formula (II).

For example, the HDL analogue PVLDLFRELLNELLEALKQKLK (SEQ ID NO: 4) included in the table below is useful in accordance with the methods described herein.

| | | LCAT ACTIVATION EXHIBITED BY EXEMPLARY CORE PEPTIDES | | | | | |
|---|---|---|---|---|---|---|---|
| PEPTIDE | | AMINO ACID SEQUENCE | ACTIVITY (%) LCAT | He (%) free | He (%) mice | He (%) SUVs | He (%) TFE |
| 1 | (SEQ ID NO:1) | PVLDLFRELLNELLEZLKQKLK | 120% | 77 | 85 | 81 | 69 |
| 2 | (SEQ ID NO:2) | GVLDLFRELLNELLEALKQKLKK | 105% | | | | |
| 3 | (SEQ ID NO:3) | PVLDLFRELLNELLEWLKQKLK | 98% | 70 | 95 | 80 | 95 |
| 4 | (SEQ ID NO:4) | PVLDLFRELLNELLEALKQKLK | 93% | 80 | 95 | 97 | 94 |
| 5 | (SEQ ID NO:5) | pVLDLFRELLNELLEALKQKLKK | 90% | | | | |
| 6 | (SEQ ID NO:6) | PVLDLFRELLNEXLEALKQKLK | 80% | 57 | 93 | 70 | 99 |
| 7 | (SEQ ID NO:7) | PVLDLFKELLNELLEALKQKLK | 83% | 77 | 89 | 85 | 73 |
| 8 | (SEQ ID NO:8) | PVLDLFRELLNEGLEALKQKLK | 83% | 20 | 90 | 61 | 93 |
| 9 | (SEQ ID NO:9) | PVLDLFRELGNELLEALKQKLK | 83% | | | | |
| 10 | (SEQ ID NO:10) | PVLDLFRELLNELLEAZKQKLK | 79% | 60 | 87 | 70 | 71 |
| 11 | (SEQ ID NO:11) | PVLDLFKELLQELLEALKQKLK | 72% | | | | |
| 12 | (SEQ ID NO:12) | PVLDLFRELLNELLEAGKQKLK | 70% | | | | |
| 13 | (SEQ ID NO:13) | GVLDLFRELLNEGLEALKQKLK | 67% | | | | |
| 14 | (SEQ ID NO:14) | PVLDLFRELLNELLEALOQOLO | 61% | 70 | 96 | 80 | |
| 15 | (SEQ ID NO:15) | PVLDLFRELWNELLEALKQKLK | 60% | 55 | 60 | 64 | 68 |
| 16 | (SEQ ID NO:16) | PVLDLLRELLNELLEALKQKLK | 59% | | | | |
| 17 | (SEQ ID NO:17) | PVLELFKELLQELLEALKQKLK | 59% | | | | |
| 18 | (SEQ ID NO:18) | GVLDLFRELLNELLEALKQKLK | 58% | | | | |
| 19 | (SEQ ID NO:19) | pVLDLFRELLNEGLEALKQKLK | 58% | | | | |
| 20 | (SEQ ID NO:20) | PVLDLFREGLNELLEALKQKLK | 57% | | | | |
| 21 | (SEQ ID NO:21) | pVLDLFRELLNELLEALKQKLK | 57% | | | | |
| 22 | (SEQ ID NO:22) | PVLDLFRELLNELLEGLKQKLK | 54% | | | | |
| 23 | (SEQ ID NO:23) | PLLELFKELLQELLEALKQKLK | 54% | | | | |
| 24 | (SEQ ID NO:24) | PVLDLFRELLNELLEALKQKLK | 53% | | | | |
| 25 | (SEQ ID NO:25) | PVLDFFRELLNEXLEALKQKLK | 51% | 46 | 82 | | 93 |
| 26 | (SEQ ID NO:26) | PVLDLFRELLNELLELLKQKLK | 47% | | | | |
| 27 | (SEQ ID NO:27) | PVLDLFRELLNELZEALKQKLK | 44% | 72 | 92 | 82 | 81 |
| 28 | (SEQ ID NO:28) | PVLDLFRELLNELWEALKQKLK | 40% | 82 | 98 | 90 | 81 |
| 29 | (SEQ ID NO:29) | AVLDLFRELLNELLEALKQKLK | 39% | | | | |

-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mice | He (%) SUVs | He (%) TFE |
|---|---|---|---|---|---|---|
| 30 | (SEQ ID NO:30) PVLDLFRELLNELLEALKQKLK† | 38% | 85 | 90 | 98 | 90 |
| 31 | (SEQ ID NO:31) PVLDLFLELLNEXLEALKQKLK | 34% | 49 | 98 | | 90 |
| 32 | (SEQ ID NO:32) XVLDLFRELLNELLEALKQKLK | 33% | | | | |
| 33 | (SEQ ID NO:33) PVLDLFREKLNELLEALKQKLK | 33% | | | | |
| 34 | (SEQ ID NO:34) PVLDZFRELLNELLEALKQKLK | 32% | 58 | 67 | 68 | 62 |
| 35 | (SEQ ID NO:35) PVLDWFRELLNELLEALKQKLK | 31% | 49 (sp) | 59 | 61 | |
| 36 | (SEQ ID NO:36) PLLELLKELLQELLEALKQKLK | 31% | 95 | 100 | | 95 |
| 37 | (SEQ ID NO:37) PVLDLFREWLNELLEALKQKLK | 29% | 65 | 75 | 76 | 73 |
| 38 | (SEQ ID NO:38) PVLDLFRELLNEXLEAWKQKLK | 29% | 25 | 49 | 21 | 49 |
| 39 | (SEQ ID NO:39) PVLDLFRELLEELLKALKKKLK | 25% | 66 | 69 | 68 | 72 |
| 40 | (SEQ ID NO:40) PVLDLFNELLRELLEALQKKLK | 25% | 66 | 84 | 79 | 77 |
| 41 | (SEQ ID NO:41) PVLDLWRELLNEXLEALKQKLK | 25% | 53 | 73 | 85 | 69 |
| 42 | (SEQ ID NO:42) PVLDEFREKLNEXWEALKQKLK | 25% | 15 | 74 | 27 | 76 |
| 43 | (SEQ ID NO:43) PVLDEFREKLWEXLEALKQKLK | 25% | | | | |
| 44 | (SEQ ID NO:44) pvldefreklneXlealkgklk | 25% | 20 | 86 | | |
| 45 | (SEQ ID NO:45) PVLDEFREKLNEXLEALKQKLK | 24% | 24 | 84 | 25 | 86 |
| 46 | (SEQ ID NO:46) PVLDEFREKLNEXLEALKQKLK | 23% | 30 | 86 | 58 | 85 |
| 47 | (SEQ ID NO:47) ~VLDLFRELLNEGLEALKQKLK | 23% | | | | |
| 48 | (SEQ ID NO:48) pvLDLFRELLNELLEALKQKLK | 22% | | | | |
| 49 | (SEQ ID NO:49) PVLDLFRNLLEKLLEALEQKLK | 22% | 57 | 65 | 52 | 57 |
| 50 | (SEQ ID NO:50) PVLDLFRELLWEXLEALKQKLK | 21% | 68 | 84 | 89 | 76 |
| 51 | (SEQ ID NO:51) PVLDLFWELLNEXLEALKQKLK | 20% | 63 | 82 | 81 | 73 |
| 52 | (SEQ ID NO:52) PVWDEFREKLNEXLEALKQKLK | 20% | sp | sp | sp | |
| 53 | (SEQ ID NO:53) VVLDLFRELLNELLEALKQKLK | 19% | | | | |
| 54 | (SEQ ID NO:54) PVLDLFRELLNEWLEALKQKLK | 19% | 76 | 71 | 84 | 78 |
| 55 | (SEQ ID NO:55) P~~~LFRELLNELLEALKQKLK | 19% | 38 | 72 | 78 | 75 |
| 56 | (SEQ ID NO:56) PVLDLFRELLNELLEALKQKKK | 18% | | | | |
| 57 | (SEQ ID NO:57) PVLDLFRNLLEELLKALEQKLK | 18% | | | | |
| 58 | (SEQ ID NO:58) PVLDEFREKLNEXLEALKQKL~ | 18% | | | | |
| 59 | (SEQ ID NO:59) LVLDLFRELLNELLEALKQKLK | 17% | | | | |
| 60 | (SEQ ID NO:60) PVLDLFRELLNELLEALKQ~~~ | 16% | 39 | 83 | 66 | 84 |
| 61 | (SEQ ID NO:61) PVLDEFRWKLNEXLEALKQKLK | 16% | | | | |
| 62 | (SEQ ID NO:62) PVLDEWREKLNEXLEALKQKLK | 16% | 15 | 85 | 43 | |
| 63 | (SEQ ID NO:63) PVLDFFREKLNEXLEALKQKLK | 16% | | | | |
| 64 | (SEQ ID NO:64) PWLDEFREKLNEXLEALKQKLK | 15% | | | | |
| 65 | (SEQ ID NO:65) ~VLDEFREKLNEXLEALKQKLK | 15% | | | | |
| 66 | (SEQ ID NO:66) PVLDLFRNLLEELLEALQKKLK | 15% | 64 | 82 | 66 | 70 |
| 67 | (SEQ ID NO:67) ~VLDLFRELLNELLEALKQKLK | 14% | 81 | 90 | 84 | 94 |
| 68 | (SEQ ID NO:68) PVLDEFRELLKEXLEALKQKLK | 14% | | | | |
| 69 | (SEQ ID NO:69) PVLDEFRKKLNEXLEALKQKLK | 13% | | | | |
| 70 | (SEQ ID NO:70) PVLDEFRELLYEXLEALKQKLK | 12% | 27 | 78 | 33 | 66 |
| 71 | (SEQ ID NO:71) PVLDEFREKLNELXEALKQKLK | 11% | | | | |
| 72 | (SEQ ID NO:72) PVLDLFRELLNEXLWALKQKLK | 11% | sp | sp | sp | |
| 73 | (SEQ ID NO:73) PVLDEFWEKLNEXLEALKQKLK | 10% | | | | |
| 74 | (SEQ ID NO:74) PVLDKFREKLNEXLEALKQKLK | 10% | | | | |
| 75[1/] | (SEQ ID NO:75) PVLDEFREKLNEELEALKQKLK | 10% | 18 | 28 | 23 | 55 |
| 76 | (SEQ ID NO:76) PVLDEFRELLFEXLEALKQKLK | 9% | 41 | 88 | | 66 |
| 77 | (SEQ ID NO:77) PVLDEFREKLNKXLEALKQKLK | 9% | | | | |
| 78 | (SEQ ID NO:78) PVLDEFRDKLNEXLEALKQKLK | | | | | |
| 79 | (SEQ ID NO:79) PVLDEFRELLNELLEALKQKLK | 9% | | | | |
| 80 | (SEQ ID NO:80) PVLDLFERLLNELLEALQKKLK | 9% | | | | |
| 81 | (SEQ ID NO:81) PVLDEFREKLNWXLEALKQKLK | | | | | |
| 82 | (SEQ ID NO:82) ~~~LDEFREKLNEXLEALKQKLK | 8% | | | | |
| 83 | (SEQ ID NO:83) PVLDEFREKLNEXLEALWQKLK | | | | | |
| 84 | (SEQ ID NO:84) PVLDEFREKLNELLEALKQKLK | 7% | | | | |
| 85 | (SEQ ID NO:85) P~LDLFRELLNELLEALKQKLK | 7% | 58 | 61 | 64 | 69 |
| 86 | (SEQ ID NO:86) PVLELFERLLDELLNALQKKLK | 7% | | | | |
| 87 | (SEQ ID NO:87) pllellkellqellealkqklk | 7% | 100 | 100 | | 100 |
| 88 | (SEQ ID NO:88) PVLDKFRELLNEXLEALKQKLK | 7% | | | | |
| 89 | (SEQ ID NO:89) PVLDEFREKLNEXLWALKQKLK | 6% | | | | |
| 90 | (SEQ ID NO:90) ~~~DEFREKLNEXLEALKQKLK | 6% | | | | |
| 91 | (SEQ ID NO:91) PVLDEFRELLNEXLEALKQKLK | 6% | 43 | 100 | | 100 |
| 92 | (SEQ ID NO:92) PVLDEFRELYNEXLEALKQKLK | 5% | | | | |
| 93 | (SEQ ID NO:93) PVLDEFREKLNEXLKALKQKLK | 5% | | | | |
| 94[2/] | (SEQ ID NO:94) PVLDEFREKLNEALEALKQKLK | 5% | 18 | 70 | 27 | 63 |
| 95 | (SEQ ID NO:95) PVLDLFRELLNLXLEALKQKLK | 5% | sp | sp | | |
| 96 | (SEQ ID NO:96) pvldlfrellneXlealkgklk | 5% | 52 | 85 | 63 | 81 |
| 97 | (SEQ ID NO:97) PVLDLFRELLNELLE~~~~~~~ | 4% | | | | |
| 98 | (SEQ ID NO:98) PVLDLFRELLNEELEALKQKLK | 2% | | | | |
| 99 | (SEQ ID NO:99) KLKQKLAELLENLLERFLDLVP | 2% | 72 | 88 | 80 | 80 |
| 100 | (SEQ ID NO:100) pvldlfrellneXlealkqklk | 2% | 83 | 92 | | 98 |
| 101 | (SEQ ID NO:101) PVLDLFRELLNWXLEALKQKLK | 2% | sp | sp | | |
| 102 | (SEQ ID NO:102) PVLDLFRELLNLXLEALKEKLK | 2% | sp | | | |
| 103 | (SEQ ID NO:103) PVLDEFRELLNEELEALKQKAK | 1% | | | | |

-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mice | He (%) SUVs | He (%) TFE |
|---|---|---|---|---|---|---|
| 104 | (SEQ ID NO:104) P~~~~~~~LLNELLEALKQKLK | 1% | 21 | 49 | 29 | 55 |
| 105 | (SEQ ID NO:105) PAADAFREAANEAAEAAKQKAK | 1% | 29 | 28 | 32 | 65 |
| 106 | (SEQ ID NO:106) PVLDLFREKLNEELEALKQKLK | 0% | | | | |
| 107 | (SEQ ID NO:107) klkqklaellenllerfldlvp | 0% | sp | sp | | 77 |
| 108 | (SEQ ID NO:108) PVLDLFRWLLNEXLEALKQKLK | 0% | 28 | 55 | | 54 |
| 109[3/] | (SEQ ID NO:109) PVLDEFREKLNERLEALKQKLK | 0% | 19 | 45 | 23 | 58 |
| 110 | (SEQ ID NO:110) PVLDEFREKLNEXXEALKQKLK | 0% | | | | |
| 111 | (SEQ ID NO:111) PVLDEFREKLWEXWEALKQKLK | 0% | | | | |
| 112 | (SEQ ID NO:112) PVLDEFREKLNEXSEALKQKLK | 0% | | | | |
| 113 | (SEQ ID NO:113) PVLDEFREKLNEPLEALKQKLK | 0% | 6 | 22 | | |
| 114 | (SEQ ID NO:114) PVLDEFREKLNEXMEALKQKLK | 0% | | | | |
| 115 | (SEQ ID NO:115) PKLDEFREKLNEXLEALKQKLK | 0% | | | | |
| 116 | (SEQ ID NO:116) PHLDEFREKLNEXLEALKQKLK | 0% | | | | |
| 117 | (SEQ ID NO:117) PELDEFREKLNEXLEALKQKLK | 0% | | | | |
| 118 | (SEQ ID NO:118) PVLDEFREKLNEXLEALEQKLK | 0% | | | | |
| 119 | (SEQ ID NO:119) PVLDEFREKLNEELEAXKQKLK | 0% | | | | |
| 120 | (SEQ ID NO:120) PVLDEFREKLNEELEXLKQKLK | 0% | | | | |
| 121 | (SEQ ID NO:121) PVLDEFREKLNEELEALWQKLK | 0% | | | | |
| 122 | (SEQ ID NO:122) PVLDEFREKLNEELEWLKQKLK | 0% | | | | |
| 123 | (SEQ ID NO:123) QVLDLFRELLNELLEALKQKLK | | | | | |
| 124 | (SEQ ID NO:124) PVLDLFOELLNELLEALOQOLO | | | | | |
| 125 | (SEQ ID NO:125) NVLDLFRELLNELLEALKQKLK | | | | | |
| 126 | (SEQ ID NO:126) PVLDLFRELLNELGEALKQKLK | | | | | |
| 127 | (SEQ ID NO:127) PVLDLFRELLNELLELLKQKLK | 47% | | | | |
| 128 | (SEQ ID NO:128) PVLDLFRELLNELLEFLKQKLK | | | | | |
| 129 | (SEQ ID NO:129) PVLELFNDLLRELLEALQKKLK | | | | | |
| 130 | (SEQ ID NO:130) PVLELFNDLLRELLEALKQKLK | | | | | |
| 131 | (SEQ ID NO:131) PVLELFKELLLNELLDALRQKLK | | | | | |
| 132 | (SEQ ID NO:132) PVLDLFRELLENLLEAL1QKKLK | | | | | |
| 133 | (SEQ ID NO:133) PVLELFERLLEDLLQALNKKLK | | | | | |
| 134 | (SEQ ID NO:134) PVLELFERLLEDLLKALNQKLK | | | | | |
| 135 | (SEQ ID NO:135) DVLDLFRELLNELLEALKQKLK | | | | | |
| 136 | (SEQ ID NO:136) PALELFKDLLQELLEALKQKLK | | | | | |
| 137 | (SEQ ID NO:137) PVLDLFRELLNEGLEAZKQKLK | | | | | |
| 138 | (SEQ ID NO:138) PVLDLFRELLNEGLEWLKQKLK | | | | | |
| 139 | (SEQ ID NO:139) PVLDLFRELWNEGLEALKQKLK | | | | | |
| 140 | (SEQ ID NO:140) PVLDLFRELLNEGLEALOQOLO | | | | | |
| 141 | (SEQ ID NO:141) PVLDFFRELLNEGLEALKQKLK | | | | | |
| 142 | (SEQ ID NO:142) PVLELFRELLNEGLEALKQKLK | | | | | |
| 143 | (SEQ ID NO:143) PVLDLFRELLNEGLEALKQKLK* | | | | | |
| 144 | (SEQ ID NO:144) pVLELFENLLERLLDALQKKLK | 111% | 89 | 88 | | 95 |
| 145 | (SEQ ID NO:145) GVLELFENLLERLLDALQKKLK | 100% | 55 | 51 | | 58 |
| 146 | (SEQ ID NO:146) PVLELFENLLERLLDALQKKLK | 86% | 97 | 100 | 100 | 95 |
| 147 | (SEQ ID NO:147) PVLELFENLLERLFDALQKKLK | 76% | | | | |
| 148 | (SEQ ID NO:148) PVLELFENLLERLGDALQKKLK | 75% | 10 | 76 | 23 | 80 |
| 149 | (SEQ ID NO:149) PVLELFENLWERLLDALQKKLK | 63% | 28 | 54 | | 47 |
| 150 | (SEQ ID NO:150) PLLELFENLLERLLDALQKKLK | 57% | | | | |
| 151 | (SEQ ID NO:151) PVLELFENLGERLLDALQKKLK | 55% | | | | |
| 152 | (SEQ ID NO:152) PVFELFENLLERLLDALQKKLK | 50% | | | | |
| 153 | (SEQ ID NO:153) AVLELFENLLERLLDALQKKLK | 49% | | | | |
| 154 | (SEQ ID NO:154) PVLELFENLLERGLDALQKKLK | 39% | 13 | 76 | 25 | 80 |
| 155 | (SEQ ID NO:155) PVLELFLNLWERLLDALQKKLK | 38% | | | | |
| 156 | (SEQ ID NO:156) PVLELFLNLLERLLDALQKKLK | 35% | | | | |
| 157 | (SEQ ID NO:157) PVLEFFENLLERLLDALQKKLK | 30% | | | | |
| 159 | (SEQ ID NO:158) PVLELFNLLERLLDWLQKKLK | 30% | | | | |
| 159 | (SEQ ID NO:159) PVLDLFENLLERLLDALQKKLK | 28% | | | | |
| 160 | (SEQ ID NO:160) PVLELFENLLERLLDWLQKKLK | 28% | 65 | 73 | 75 | 61 |
| 161 | (SEQ ID NO:161) PVLELFENLLERLLEALQKKLK | 27% | | | | |
| 162 | (SEQ ID NO:162) PVLELFENWLERLLDALQKKLK | 27% | 68 | 83 | 81 | |
| 163 | (SEQ ID NO:163) PVLELFENLLERLWDALQKKLK | 26% | 27 | 53 | | 55 |
| 164 | (SEQ ID NO:164) PVLELFENLLERLLDAWQKKLK | 24% | 37 | 66 | 51 | 61 |
| 165 | (SEQ ID NO:165) PVLELFENLLERLLDLLQKKLK | 23% | | | | |
| 166 | (SEQ ID NO:166) PVLELFLNLLEKLLDALQKKLK | 22% | | | | |
| 167 | (SEQ ID NO:167) PVLELFENGLERLLDALQKKLK | 18% | | | | |
| 168 | (SEQ ID NO:168) PVLELFEQLLEKLLDALQKKLK | 17% | | | | |
| 169 | (SEQ ID NO:169) PVLELFENLLEKLLDALQKKLK | 17% | | | | |
| 170 | (SEQ ID NO:170) PVLELFENLLEOLLDALQOOLO | 17% | | | | |
| 171 | (SEQ ID NO:171) PVLELFENLLEKLLDLLQKKLK | 16% | | | | |
| 172 | (SEQ ID NO:172) PVLELFLNLLERLGDALQKKLK | 16% | | | | |
| 173 | (SEQ ID NO:173) PVLDLFDNLLDRLLDLLNKKLK | 15% | | | | |
| 174 | (SEQ ID NO:174) pvlelfenllerlldalgkklk | 13% | | | | |
| 175 | (SEQ ID NO:175) PVLELFENLLERLLELLNKKLK | 13% | | | | |
| 176 | (SEQ ID NO:176) PVLELWENLLERLLDALQKKLK | 11% | | | | |
| 177 | (SEQ ID NO:177) GVLELFLNLLERLLDALQKKLK | 10% | | | | |

-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mice | He (%) SUVs | He (%) TFE |
|---|---|---|---|---|---|---|
| 178 | (SEQ ID NO:178) PVLELFDNLLEKLLEALQKKLR | 9% | | | | |
| 179 | (SEQ ID NO:179) PVLELFDNLLERLLDALQKKLK | 8% | | | | |
| 180 | (SEQ ID NO:180) PVLELFDNLLDKLLDALQKKLR | 8% | | | | |
| 181 | (SEQ ID NO:181) PVLELFENLLERWLDALQKKLK | 8% | | | | |
| 182 | (SEQ ID NO:182) PVLELFENLLEKLLEALQKKLK | 7% | | | | |
| 183 | (SEQ ID NO:183) PLLELFENLLEKLLDALQKKLK | 6% | | | | |
| 184 | (SEQ ID NO:184) PVLELFLNLLERLLDAWQKKLK | 4% | | | | |
| 185 | (SEQ ID NO:185) PVLELFENLLERLLDALQOOLO | 3% | | | | |
| 186 | (SEQ ID NO:186) PVLELFEQLLERLLDALQKKLK | | | | | |
| 187 | (SEQ ID NO:187) PVLELFENLLERLLDALNKKLK | | | | | |
| 188 | (SEQ ID NO:188) PVLELFENLLDRLLDALQKKLK | | | | | |
| 189 | (SEQ ID NO:189) DVLELFENLLERLLDALQKKLK | | | | | |
| 190 | (SEQ ID NO:190) PVLEFWDNLLDKLLDALQKKLR | | | | | |
| 191 | (SEQ ID NO:191) PVLDLLRELLEELKQKLK* | 100% | | | | |
| 192 | (SEQ ID NO:192) PVLDLFKELLEELKQKLK* | 100% | 36 | | | 56 |
| 193 | (SEQ ID NO:193) PVLDLFRELLEELKQKLK* | 96% | 34 | 88 | 87 | 87 |
| 194 | (SEQ ID NO:194) PVLELFRELLEELKQKLK* | 88% | 38 | 93 | | 93 |
| 195 | (SEQ ID NO:195) PVLELFKELLEELKQKLK* | 87% | | | | |
| 196 | (SEQ ID NO:196) PVLDLFRELLEELKNKLK* | 81% | | | | |
| 197 | (SEQ ID NO:197) PLLDLFRELLEELKQKLK* | 81% | 43 | 70 | | 69 |
| 198 | (SEQ ID NO:198) GVLDLFRELLEELKQKLK* | 80% | | | | |
| 199 | (SEQ ID NO:199) PVLDLFRELWEELKQKLK* | 76% | 35 | 77 | 80 | 79 |
| 200 | (SEQ ID NO:200) NVLDLFRELLEELKQKLK* | 75% | | | | |
| 201 | (SEQ ID NO:201) PLLDLFKELLEELKQKLK* | 74% | | | | |
| 202 | (SEQ ID NO:202) PALELFKDLLEELRQKLR* | 70% | | | | |
| 203 | (SEQ ID NO:203) AVLDLFRELLEELKQKLK* | 66% | | | | |
| 204 | (SEQ ID NO:204) PVLDFFRELLEELKQKLK* | 63% | | | | |
| 205 | (SEQ ID NO:205) PVLDLFREWLEELKQKLK* | 60% | | | | |
| 206 | (SEQ ID NO:206) PLLELLKELLEELKQKLK* | 57% | | | | |
| 207 | (SEQ ID NO:207) PVLELLKELLEELKQKLK* | 50% | | | | |
| 208 | (SEQ ID NO:208) PALELFKDLLEELRQRLK* | 48% | | | | |
| 209 | (SEQ ID NO:209) PVLDLFRELLNELLQKLK | 47% | 54 | 71 | 67 | 62 |
| 210 | (SEQ ID NO:210) PVLDLFRELLEELKQKLK | 46% | 20 | 63 | 37 | 53 |
| 211 | (SEQ ID NO:211) PVLDLFRELLEELOQOLO* | 45% | | | | |
| 212 | (SEQ ID NO:212) PVLDLFOELLEELOQOLK* | 43% | | | | |
| 213 | (SEQ ID NO:213) PALELFKDLLEEFRQRLK* | 42% | | | | |
| 214 | (SEQ ID NO:214) pVLDLFRELLEELKQKLK* | 39% | | | | |
| 215 | (SEQ ID NO:215) PVLDLFRELLEEWKQKLK* | 38% | 28 | 63 | 53 | 68 |
| 216 | (SEQ ID NO:216) PVLELFKELLEELKQKLK | 35% | | | | |
| 217 | (SEQ ID NO:217) PVLDLFRELLELLKQKLK | 30% | 52 | 78 | 76 | 70 |
| 218 | (SEQ ID NO:218) PVLDLFRELLNELLQKLK* | 29% | | | | |
| 219 | (SEQ ID NO:219) PVLDLFRELLNELWQKLK | 24% | | | | |
| 220 | (SEQ ID NO:220) PVLDLFRELLEELQKKLK | 22% | 27 | 64 | 54 | 64 |
| 221 | (SEQ ID NO:221) DVLDLFRELLEELKQKLK* | 12% | | | | |
| 222 | (SEQ ID NO:222) PVLDAFRELLEALLQLKK | 8% | | | | |
| 223 | (SEQ ID NO:223) PVLDAFRELLEALAQLKK | 8% | 21 | 56 | 23 | 51 |
| 224 | (SEQ ID NO:224) PVLDLFREGWEELKQKLK | 8% | | | | |
| 225 | (SEQ ID NO:225) PVLDAFRELAEALAQLKK | 1% | | | | |
| 226 | (SEQ ID NO:226) PVLDAFRELGEALLQLKK | 1% | | | | |
| 227 | (SEQ ID NO:227) PVLDLFRELGEELKQKLK* | 0% | | | | |
| 228 | (SEQ ID NO:228) PVLDLFREGLEELKQKLK* | 0% | | | | |
| 229 | (SEQ ID NO:229) PVLDLFRELLEEGKQKLK* | 0% | | | | |
| 230 | (SEQ ID NO:230) PVLELFERLLEDLQKKLK | | | | | |
| 231 | (SEQ ID NO:231) PVLDLFRELLEKLEQKLK | | | | | |
| 232 | (SEQ ID NO:232) PLLELFKELLEELKQKLK* | | | | | |
| 237[4/] | (SEQ ID NO:237) LDDLLQKWAEAFNQLLKK | 11% | 30 | 66 | 45 | — |
| 238[5/] | (SEQ ID NO:238) EWLKAFYEKVLEKLKELF* | 19% | 49 | 72 | 60 | 58 |
| 239[6/] | (SEQ ID NO:239) EWLEAFYKKVLEKLKELF* | 11% | 44 | 49 | | sp |
| 240 | (SEQ ID NO:240) DWLKAFYDKVAEKLKEAF* | 10% | 16 | 68 | 59 | 57 |
| 241 | (SEQ ID NO:241) DWFKAFYDKVFEKFKEFF | 8% | | | | |
| 242[7/] | (SEQ ID NO:242) GIKKFLGSIWKFIKAFVG | 7% | | | | |
| 243 | (SEQ ID NO:243) DWFKAFYDKVAEKFKEAF | 5% | 10 | 64 | 50 | |
| 244[8/] | (SEQ ID NO:244) DWLKAPYDKVAEKLKEAF | 5% | 9 | 40 | 13 | 48 |
| 245 | (SEQ ID NO:245) DWLKAFYDKVFEKFKEFF | 4% | 38 | 77 | 70 | sp |
| 246[9/] | (SEQ ID NO:246) EWLEAFYKKVLEKLKELF | 4% | 18 | 44 | 47 | |
| 247 | (SEQ ID NO:247) DWFKAFYDKFFEKFKEFF | 3% | | | | |
| 248[10/] | (SEQ ID NO:248) EWLKAFYEKVLEKLKELF | 3% | 18 | 45 | 13 | |
| 249[11/] | (SEQ ID NO:249) EWLKAEYEKVEEKLKELF* | | | | | |
| 250[12/] | (SEQ ID NO:250) EWLKAEYEKVLEKLKELF* | | | | | |
| 251[13/] | (SEQ ID NO:251) EWLKAFYKKVLEKLKELF* | | | | | |
| 252 | (SEQ ID NO:252) PVLDLFRELLEQKLK* | | | | | |
| 253 | (SEQ ID NO:253) PVLDLFRELLEELKQK* | | | | | |
| 254 | (SEQ ID NO:254) PVLDLFRELLEKLKQK* | | | | | |
| 255 | (SEQ ID NO:255) PVLDLFRELLEKLQK* | | | | | |

-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mice | He (%) SUVs | He (%) TFE |
|---|---|---|---|---|---|---|
| 256 | (SEQ ID NO:256) PVLDLFRELLEALKQK* | | | | | |
| 257 | (SEQ ID NO:257) PVLDLFENLLERLKQK* | | | | | |
| 258 | (SEQ ID NO:258) PVLDLFRELLNELKQK* | | | | | |

[1] Segreat's Consensus 22-mer peptide (Anantharamaiah et al., 1990, Arteriosclerosis 10(1): 95-105).
[2] [A$^{13}$]-Consensus 22-mer peptide (Anantharamaiah et al., 1990, Arteriosclerosis 10(1): 95-105).
[3] [R$^{13}$]-Consensus 22-mer peptide (Anantharamaiah et al., 1990, Arteriosclerosis 10(1): 95-105).
[4] Id-3 peptide (Labeur et al., 1997, Arteriosclerosis, Thrombosis and Vascular Biology 17(3): 580-588).
[5] Ac-18AMOD-C(O)NH$_2$ peptide (Epand et al., 1987, J. Biol. Chem, 262(19): 9389-9396).
[6] Ac-18AM4-C(O)NH$_2$ peptide (Brasseur, 1993, Biochim. Biophys. Acta 1170: 1-7).
[7] 18L peptide (Degreat et al., 1990, Proteins: Structure, Function and Genetics 8: 103-117).
[8] 18A peptide (Anantharamiah et al., 1985, J. Biol. Chem. 260(18): 10248-10255).
[9] 18AM4 peptide (Rosseneu et al., WO93/25581; Corijn et al., 1993, Biochim. Biophysy. Acta 1170: 8-16).
[10] [Glu$^{1,8}$; Leu$^{5,11,17}$] 18A peptide (Epand et al., 1987, J. Biol Chem. 262(19): 9389-9396).
[11] Ac-18AM3-C(O)NH$_2$ (Rosseneu et al., WO93/25581).
[12] Ac-18AM2-C(O)NH$_2$ (Rosseneu et al., WO93/25581).
[13] Ac-18AM1-C(O)NH$_2$ (Rosseneu et al., WO93/25581).
In the table, * indicates peptides that are N-terminal acetylated and C-terminal amidated;
†indicates peptides that are N-terminal dansylated;
sp indicates peptides that exhibited solubility problems under the experimental conditions;
X is Aib;
Z is Nal;
O is Orn;
He (%) designates percent helicity;
mics designates micelles;
~ and indicates deleted amino acids.

The high density lipoproteins comprise a protein component, and lipid. The proteins are preferably apolipoproteins, e.g. human apolipoproteins such as apolipoprotein A-I (apoA-II) or apolipoprotein A-II (apoA-II) or recombinant apolipoproteins, or functionally homologous peptides with similar properties. Suitable lipids are phospholipids, preferably phosphatidyl choline, optionally mixed with other lipids (cholesterol, cholesterol esters, triglycerides, or other lipids). The lipids may be synthetic lipids, naturally occurring lipids or combinations thereof.

Production of reconstituted HDL is described, by way of example, in U.S. Pat. No. 5,652,339 and by Matz and Jonas (24) and Lerch et al. (25). Production of recombinant HDL is described, by way of example, in European Patent No. EP 469017 (in yeast), U.S. Pat. No. 6,559,284 (in *E. coli*), and International Patent Publications Nos. WO 87/02062 (in *E. coli*, yeast and Cho cells) and WO 88/03166 (in *E. coli*). The contents of each of these documents are incorporated herein by reference.

Preferably, the HDL is reconstituted HDL.

The HDL is administered in an effective amount. An "effective amount" means an amount necessary at least partly to attain the desired response, or to delay the onset or inhibit progression or halt altogether, the onset or progression of the particular condition being treated. The amount varies depending upon the health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials.

Preferred HDL dosage ranges are from 0.1-200 mg, more preferably 10-80 mg, HDL (weight based on apolipoprotein) per kg body weight per treatment. For example, the dosage of HDL which is administered may be about 0.2-100 mg HDL per kg body weight (weight based on apolipoprotein) given as an intravenous injection and/or as an infusion for a clinically necessary period of time, e.g. for a period ranging from a few minutes to several hours, e.g. up to 24 hours. If necessary, the HDL administration may be repeated one or several times. The actual amount administered will be determined both by the nature of the disease which is being treated and by the rate at which the HDL is being administered.

Preferably, the patient is a human, however the present invention extends to treatment and/or prophylaxis of other mammalian patients including primates, livestock animals (e.g. sheep, pigs, cattle, horses, donkeys), laboratory test animals (e.g. mice, rabbits, rats, guinea pigs), companion animals (e.g. dogs, cats) and captive wild animals.

In accordance with the present invention, the HDL is administered to a patient by a parenteral route of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular) and under the skin (subcutaneous). The HDL may also be administered in a depot or slow release formulation, for example, subcutaneously, intradermally or intramuscularly, in a dosage which is sufficient to obtain the desired pharmacological effect.

Compositions suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, for example as a solution in a polyethylene glycol and lactic acid. Among the acceptable vehicles and solvents that may be employed are water, Ringer's solution and isotonic sodium chloride solution. In addition, sterile, fixed oils are conveniently employed as a solvent or suspending medium. For this purpose, any bland fixed oil may be employed including synthetic mono- or di-glycerides. In addition, fatty acids such as oleic acid find use in the preparation of injectables.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer.

The present invention also provides the use of high density lipoprotein (HDL) in the manufacture of a medicament for parenteral administration to a patient for the treatment and/or prophylaxis of an inflammatory condition of the intestine of the patient.

In yet another aspect, the invention provides an agent for parenteral administration in the treatment and/or prophylaxis of an inflammatory condition of the intestine of a patient, which comprises high density lipoprotein (HDL).

The present invention is further illustrated by the following non-limiting Examples.

EXAMPLES

Materials and Methods

Animals

Male Sprague-Dawley rats (300-350 g; Charles River; Milan; Italy) were housed in a controlled environment and provided with standard rodent chow and water. Animal care was in compliance with Italian regulations on protection of animals used for experimental and other scientific purpose (D.M. 116192) as well as with the EEC regulations (O.J. of E.C. L 358/1 Dec. 18, 1986).

Experimental Groups (Colitis Study)

Upon completion of surgical procedures, rats were randomly allocated into the following four groups: (i) DNBS+ saline group; rats were given DNBS (100 mg/kg, i.c.) (N=10), (ii) DNBS+recHDL group; rats were subjected to identical procedures as above and administered recHDL (40 mg/kg/day, i.v.) for 3 days (N=10), (iii) Sham+saline group; (sham-operated) rats were subjected to identical procedures as above except that the vehicle alone (50% ethanol, 0.8 ml) was injected instead of DNBS and were maintained under anaesthesia for the duration of the experiment (N=10), (vi) Sham+ HDL group; identical to sham-operated rats except for the administration of recHDL (40 mg/kg/day, i.v.) (N=10). The dose of recHDL used in the present study was taken from previous studies showing efficacy in models of renal I/R injury (11).

Experimental Groups (SAO Study)

Upon completion of surgical procedures, rats were randomly allocated into the following four groups: (i) I/R+saline group; rats were subjected to SAO shock (45 min) followed by reperfusion (6 h) (N=10), (ii) I/R+rec HDL group; rats were subjected to identical surgical procedures as above and administered recHDL (80 mg/kg, i.v.) 30 min prior to commencement of I/R (N=10), (iii) Sham+saline group; (sham-operated) rats were subjected to identical surgical procedures except for SAO shock and were maintained under anaesthesia for the duration of the experiment (N=10), (vi) Sham+re-cHDL group; identical to sham-operated rats except for the administration of recHDL (80 mg/kg, i.v.) 30 min prior to commencing I/R (N=10).

Induction of Experimental Colitis

Colitis was induced by using a technique of acid-induced colon inflammation as described previously (23). In fasted rats lightly anaesthetised with isoflurane, a 3.5 F catheter was inserted into the colon via the anus until approximately the splenic flexure (8 cm from the anus). DNBS (100 mg/kg i.c.) was dissolved in 50% ethanol (total volume, 0.8 ml). Thereafter, the animals were kept for 15 minutes in a Trendelenburg position to avoid reflux. After colitis and sham-colitis induction, the animals were observed for 3 days. On Day 4, the animals were weighed and anaesthetised with chloral hydrate (400 mg/kg, i.p.), and the abdomen was opened by a midline incision. The colon was removed, freed from surrounding tissues, opened along the antimesenteric border, rinsed, weighed, and processed for histology and immunohistochemistry. The macroscopic damage score, according to Wallace et al. (23) was assessed.

Splanchnic Artery Occlusion Shock (SAO-Shock)

Male Sprague-Dawley rats were anaesthetised with sodium pentobarbital (45 mg/kg, i.p.). Following anaesthesia, catheters were placed in the carotid artery and jugular vein as described previously (13). Blood pressure was monitored continuously by a Maclab A/D converter (AD Instruments), and stored and displayed on a Macintosh personal computer. After midline laparotomy, the celiac and superior mesenteric arteries were isolated near their aortic origins. During this procedure, the intestinal tract was maintained at 37° C. by placing it between gauze pads soaked with warmed 0.9% NaCl solution.

Rats were observed for a 30 min stabilisation period before either splanchnic ischaemia or sham ischaemia. SAO shock was induced by clamping both the superior mesenteric artery and the celiac trunk, resulting in a total occlusion of these arteries for 45 min. After this period of occlusion, the clamps were removed. In one study, the various groups of rats were sacrificed 60 min after the commencement of reperfusion for histological examination of the bowel and for biochemical studies, as described below. In another set of studies, the various groups of rats were observed for 6 h following reperfusion in order to determine survival differences.

Reconstituted High Density Lipoprotein (recHDL).

The discoidal recHDLs were provided by ZLB-Bioplasma, Bern, Switzerland. The particles, containing human apo A-I as the sole protein and soybean phosphatidylcholine as the sole phospholipid were prepared using cholate dialysis (24). Their physicochemical properties have been described in detail (25).

Light Microscopy

Ileum was collected after 1 h of reperfusion from the rats subjected to SAO shock. The colon was collected 4 days after DNBS administration. After fixation for 1 week at room temperature in Dietrich solution (14.25% ethanol, 1.85% formaldehyde, 1% acetic acid), samples were dehydrated in graded ethanol and embedded in Paraplast (Sherwood Medical, Mahwah, N.J.). Thereafter, 7-mm sections were deparaffinized with xylene, stained with haematoxylin-eosin and trichromic van Giesson's stain, and observed in a Dialux 22 Leitz (Wetziar, Germany) microscope. Colon damage was scored by two independent observers as described previously (26), according to the following morphological criteria: 0, no damage; 1, localised hyperaemia without ulcers; 2, linear ulcers with no significant inflammation; 3, linear ulcers with inflammation at one site; 4, two or more major sites of inflammation and ulceration extending>1 cm along the length of the colon; and 5-8, one point is added for each centimeter of ulceration beyond an initial 2 cm.

Immunohistochemical Localisation for ICAM-I, Nitrotyrosine and Poly (ADP-Ribose) (PAR).

At the specified time, the ileum and the colon tissues were fixed in 10% (w/v) phosphate buffered saline (PBS)-buffered formaldehyde and 8 µm sections were prepared from paraffin embedded tissues. After deparaffinization, endogenous peroxidase was quenched with 0.3% (v/v) hydrogen peroxide in 60% (v/v) methanol for 30 min. The sections were permeablised with 0.1% (w/v) Triton X-100 in PBS for 20 min. Nonspecific adsorption was minimised by incubating the sections in 2% (v/v) normal goat serum in PBS for 20 min. Endogenous biotin or avidin binding sites were blocked by sequential incubation for 15 min with biotin and avidin (DBA, Milan, Italy), respectively. Sections were incubated overnight with anti-nitrotyrosine rabbit polyclonal antibody (1:500 in PBS, v/v) or with anti-poly (ADP-ribose) goat polyclonal antibody (1:500 in PBS, v/v) or with mouse anti-rat antibody directed at ICAM-1 (CD54) (1:500 in PBS, v/v) (DBA, Milan, Italy). Sections were washed with PBS, and incubated with secondary antibody. Specific labelling was detected with a biotin-conjugated goat anti-rabbit IgG and avidin-biotin peroxidase complex (DBA, Milan, Italy). To verify the binding specificity for ICAM-1 and PAR, some sections were also incubated with primary antibody only (no secondary antibody) or with secondary antibody only (no primary antibody). In these situations, no positive staining was found in the sections indicating that the immunoreactions were positive in all the experiments carried out. In order to confirm that the immunoreactions for the nitrotyrosine were specific some sections were also incubated with the primary antibody (anti-nitrotyrosine) in the presence of excess nitrotyrosine (10 mM) to verify the binding specificity. Immunocytochemistry photographs (N=5) were assessed by densitometry as previously described (27) by using Optilab Graftek software on a Macintosh personal computer.

Myeloperoxidase (MPO) Activity

MPO activity, an indicator of PMN accumulation, was determined as previously described (28). At the specified time point the ileum and the colon were removed and weighed. The tissues were homogenised in a solution containing 0.5% hexa-decyl-trimethyl-ammonium bromide and 10 mM 3-(N-morpholino)-propane-sulfonic acid dissolved in 80 mM sodium phosphate buffer (pH 7), and centrifuged for 30 min at 20,000 g at 4° C. An aliquot of the supernatant was then allowed to react with a solution of tetra-methyl-benzidine (16 mM) and 1 mM hydrogen peroxide. The rate of change in absorbance was measured by a spectrophotometer at 650 nm.

MPO activity was defined as the quantity of enzyme degrading 1 µmol of peroxide/min at 37° C. and was expressed in units per gram weight of wet tissue.

Malondialdehyde (MDA) Measurement

The levels of MDA in the ileum and colon were determined as an indicator of lipid peroxidation (29). At the specified time point the ileum and the colon were removed, weighed and homogenised in 1.15% KCl solution. An aliquot (100 µl) of the homogenate was added to a reaction mixture containing 200 µl of 8.1% SDS, 1500 µl of 20% acetic acid (pH 3.5), 1500 µl of 0.8% thiobarbituric acid and 700 µl distilled water. Samples were then boiled for 1 h at 95° C. and centrifuged at 3,000×g for 10 min. The absorbance of the supernatant was measured by spectrophotometry at 650 nm.

Measurement of Cytokines

The levels of TNF-α and IL-1β were evaluated in the plasma collected 60 min after reperfusion in the SAO model and in the colon tissues at 4 days after intra-colonic injection of DNBS. The assay was carried out by using a colorimetric, commercial kit (Calbiochem-Novabiochem Corporation, USA). The ELISA (Enzyme-Linked Immunosorbent Assay) has a lower detection limit of 5 pg/ml.

Materials.

Biotin blocking kit, biotin-conjugated goat anti-rabbit IgG and avidin-biotin peroxidase complex were obtained from Vector Laboratories (Burlingame, Calif., USA). Primary anti-nitrotyrosine antibody was purchased from Upstate Biotech (Saranac Lake, N.Y.). Primary ICAM-1 (CD54) was purchased from Pharmingen (DBA, Milan, Italy). All other reagents and compounds used were purchased from Sigma Chemical Company (Sigma, St. Louis, Mo.).

Data Analysis

All values in the figures and text are expressed as mean±standard error (s.e.m.) of the mean of N observations. For the in vivo studies N represents the number of animals studied. In the experiments involving histology or immunohistochemistry, the figures shown are representative of at least three experiments performed on different experimental days. The results were analysed by one-way ANOVA followed by a Bonferroni post-hoc test for multiple comparisons. A p-value less of than 0.05 was considered significant.

Results

Protective Effects of HDL in Splanchnic Artery Occlusion Shock

Figure 2:
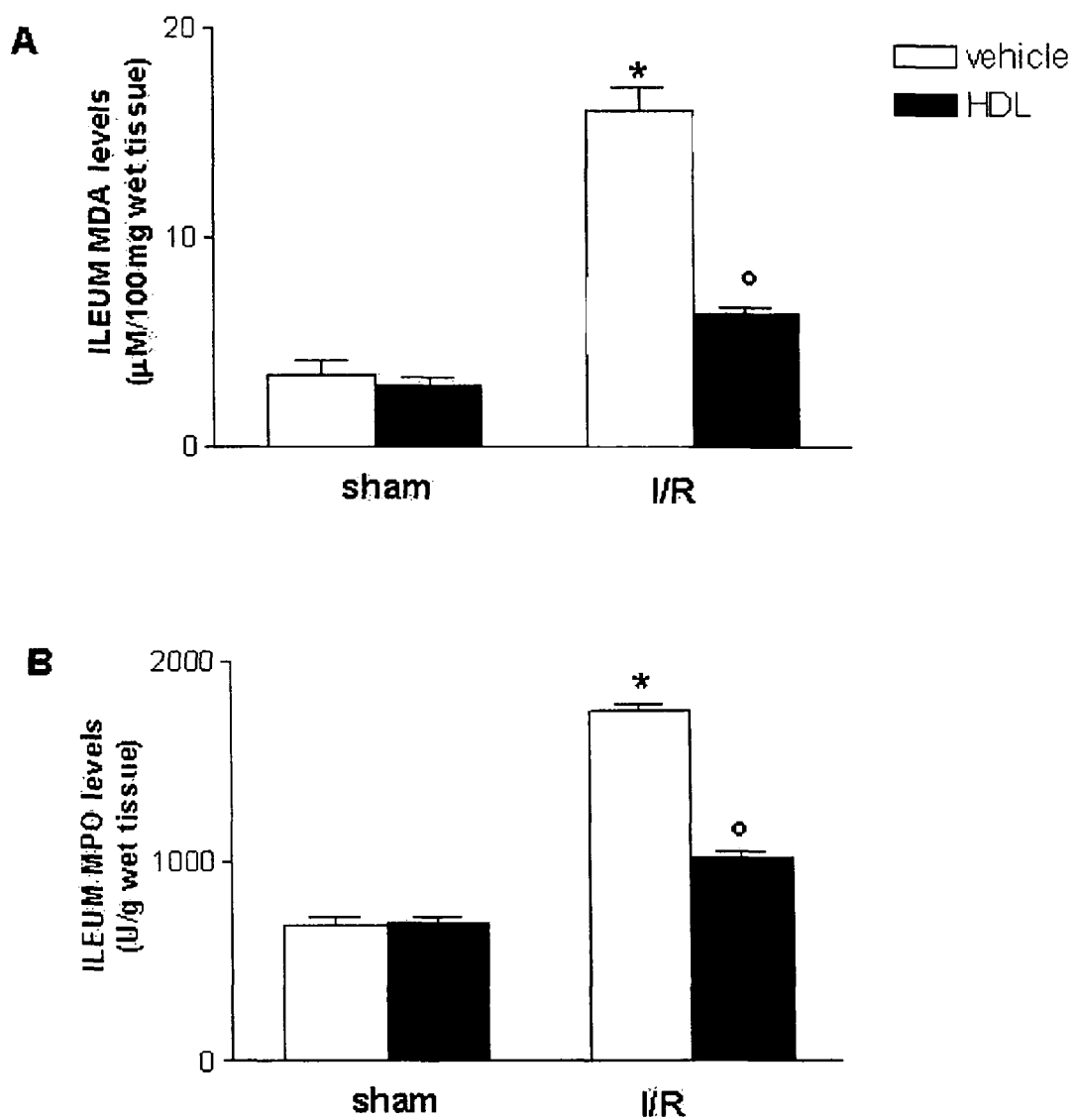
FIG. 2 shows MDA and MPO tissue levels. Reperfusion of the ischaemic splanchnic circulation leads to profound increase in MDA levels (A) and in MPO (B) in ileum tissues which is inhibited by HDL treatment (80 mg/kg). Values are means±S.E.M. of 10 rats for each group. *P<0.01 versus sham, °P<0.01 versus I/R.
Figure 3:
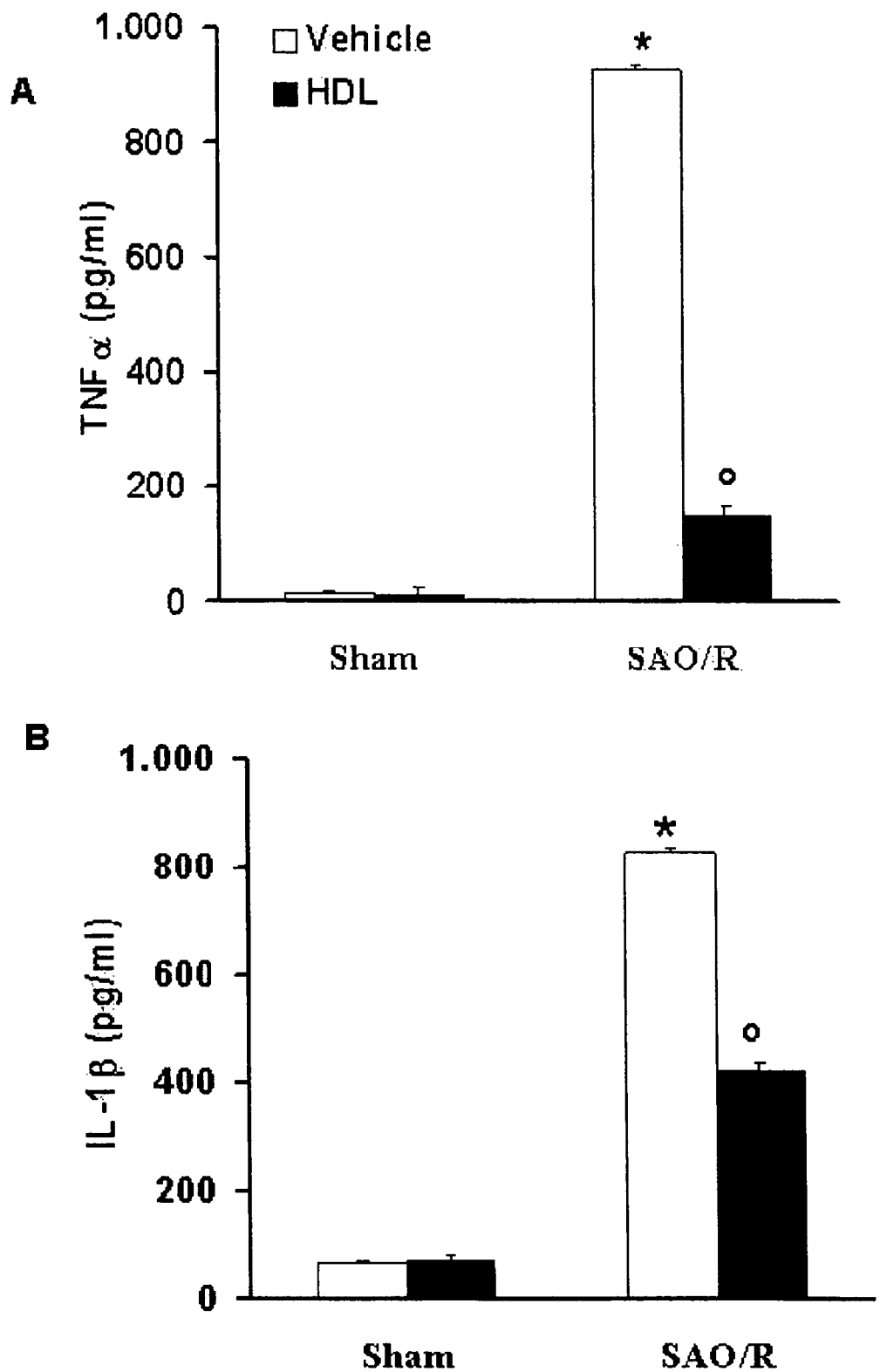
FIG. 3 shows plasma levels of TNF-α and IL-1β. Reperfusion of the ischaemic splanchnic circulation leads to profound increase in plasma TNFα and IL-1β production and this is inhibited by HDL (80 mg/kg). Values are means±S.E.M. of 10 rats for each group. *P<0.01 versus sham, °P<0.01 versus I/R.
Figure 4:
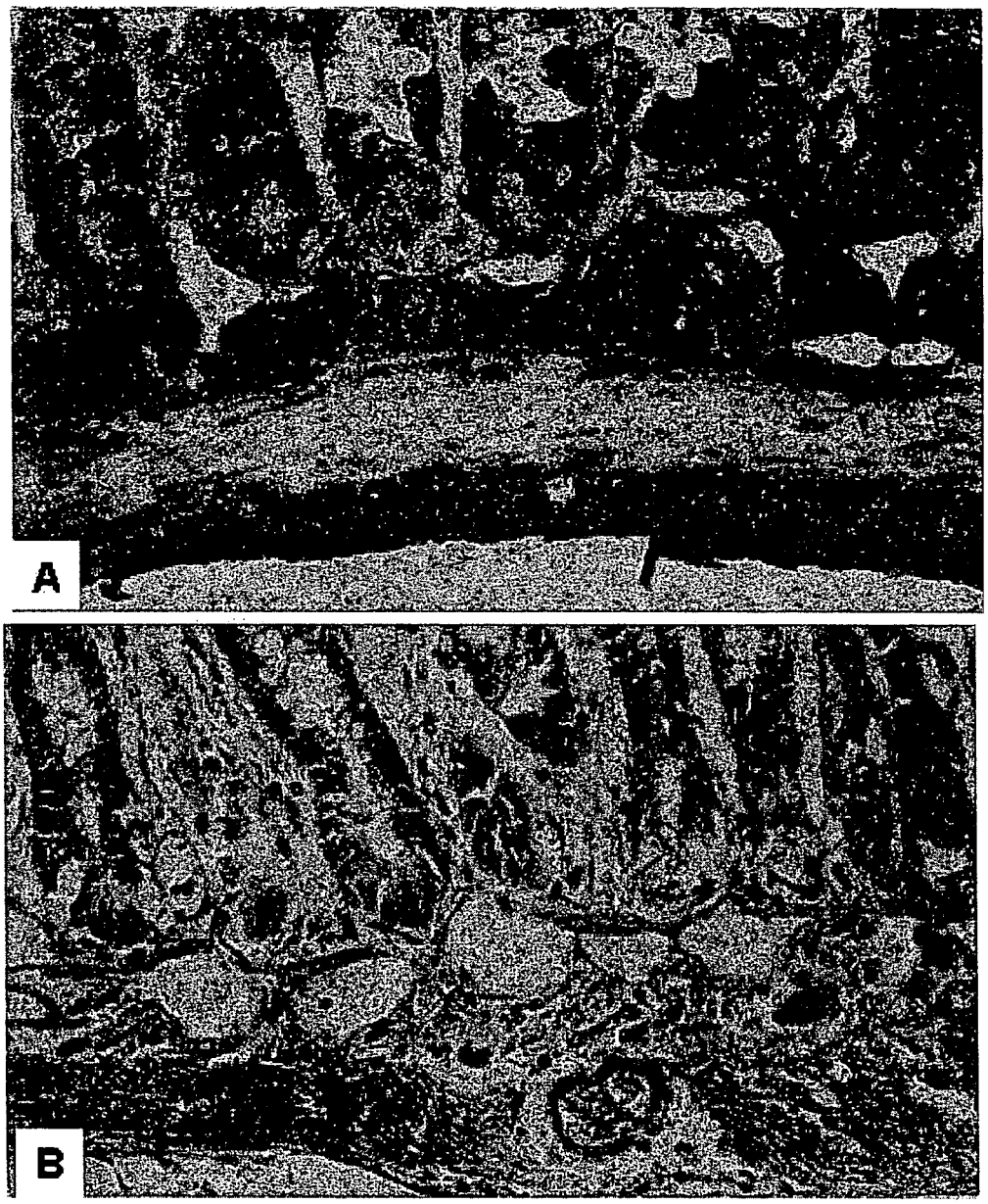
FIG. 4 shows immunohistochemical staining of ICAM-1. I/R induced an increase of the positive staining for ICAM-1 along the endothelium wall (A). In HDL-treated rats (B) subjected to SAO-shock, there was no increase of immunostaining for ICAM-1, which was present only along the endothelium wall. Original magnification: ×500. Figure is representative of at least 3 experiments performed on different experimental days.
Figure 5:
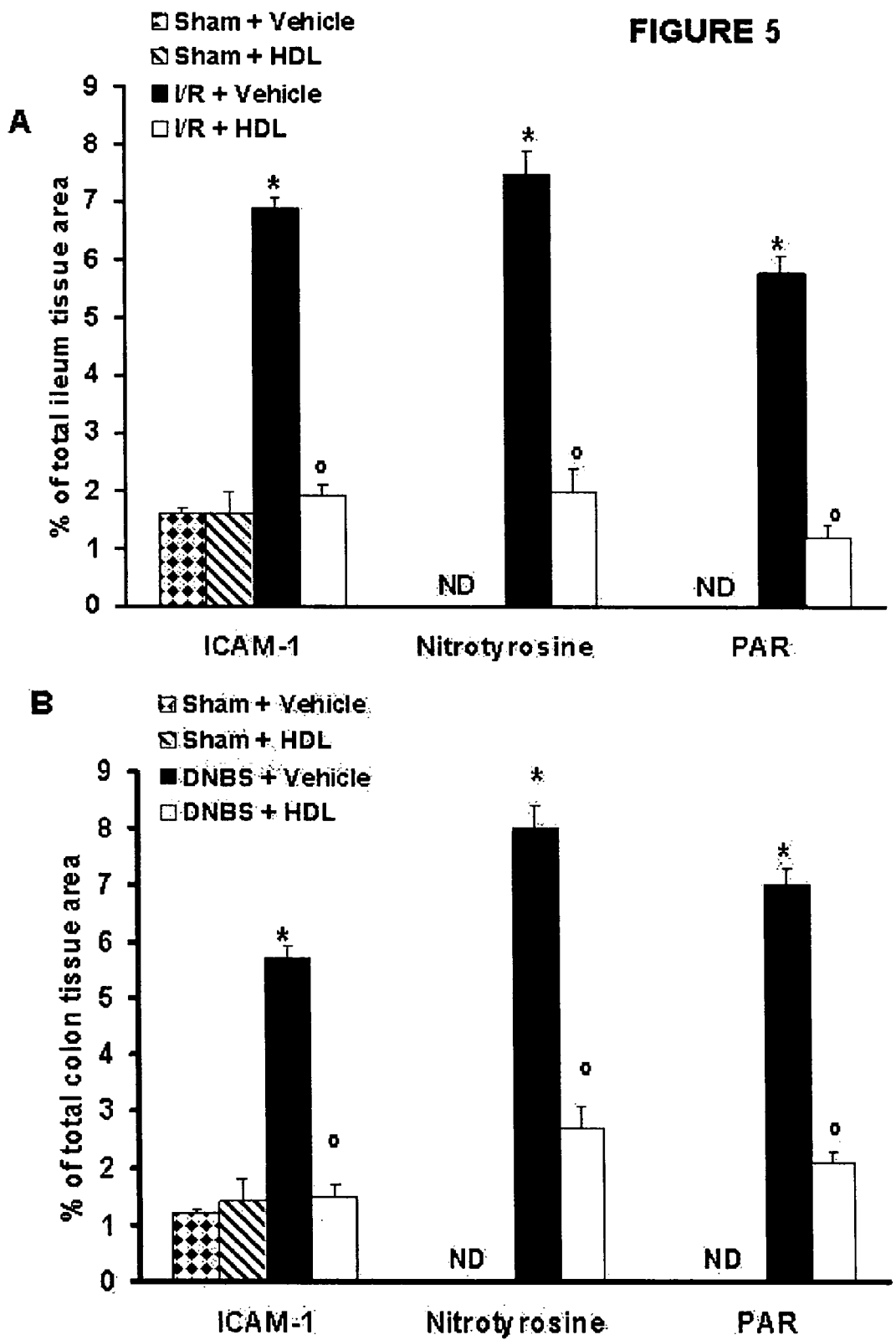
FIG. 5 shows typical Densitometry evaluation. Densitometry analysis of Immunocytochemistry photographs (n=5) for ICAM-1, nitrotyrosine and PAR from ileum (A) and from colon (B) was assessed. The assay was carried out by using Optilab Graftek software on a Macintosh personal computer (CPU G3-266). Data are expressed as % of total tissue area. *P<0.01 versus Sham. °P<0.01 versus IR or versus DNBS.
Figure 6:
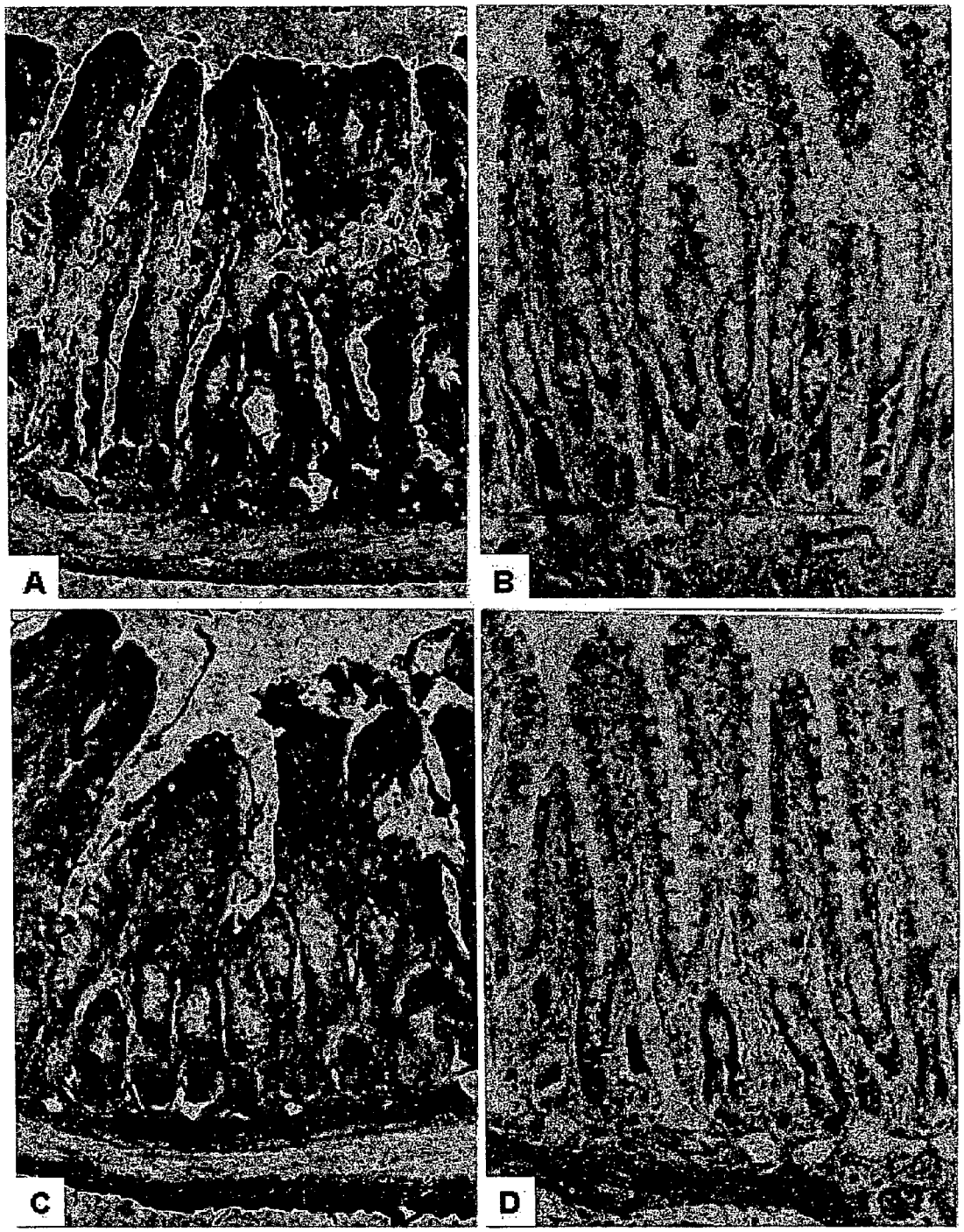
FIG. 6 shows immunohistochemical staining of nitrotyrosine and PAR. After reperfusion nitrotyrosine (A) and PAR (C) staining was localised in the injured area from a SAO-shocked rat. There was no detectable immunostaining for nitrotyrosine (B) and PAR (D) in the ileum from HDL-treated rats. Original magnification: ×500. Figure is representative of at least 3 experiments performed on different experimental days.
Figure 7:
FIG. 7 shows the effect of HDL treatment on the tissue damage. Distal ileum section from SAO shocked-rats showed inflammatory cell infiltration extending through the wall and concentrated below the epithelial layer and demonstrating oedema of the distal portion of the villi (A). Distal ileum from HDL-treated rats (B) shows reduced SAO-induced organ injury. Original magnification: ×125. Figure is representative of at least 3 experiments performed on different experimental days.
Figure 7:
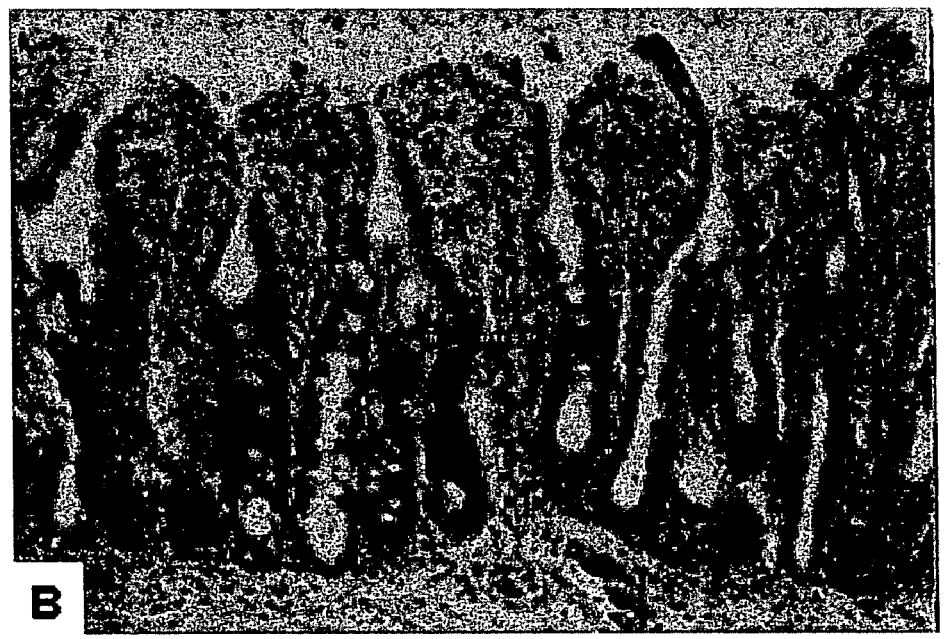

Occlusion of the splanchnic arteries produced an increase in MAP, which then decreased until death occurred (FIG. 1A). The mean survival time was found to be 74±1.7 min, whereas control sham animals survived for the entire period of the experiment (FIG. 1B). Administration of recHDL significantly prevented the fall in blood pressure seen after reperfusion and increased the survival rate (FIG. 1). Having established the survival time, in another series of experiments, animals were sacrificed either after the period of ischaemia or 60 minutes post-reperfusion in order to collect blood and tissues for biochemical analysis. Reperfusion of the ischaemic splanchnic circulation led to the following events: a substantial increase in intestinal lipid peroxidation products as determined by increased levels of MDA (FIG. 2A), TNF-α and IL-1β (FIG. 3), and a profound infiltration of PMNs into the intestine as determined by MPO activity (FIG. 2B). Ileum sections collected from SAO-shocked rats at 60 min of reperfusion showed an increase of positive staining for ICAM-1 along vessels and in the necrotic tissue (FIGS. 4A, 5A). These inflammatory events were triggered by the reperfusion phase since no changes were observed when blood or tissues were removed after the period of ischaemia alone (FIG. 5A). recHDL (80 mg/kg), when given i.v. 30 min prior to ischaemia, significantly inhibited the increased levels of MDA in the ileum (FIG. 2A) as well as TNF-α and IL-1β (FIG. 3). HDL significantly reduced the PMN infiltration into the ileum (FIG. 2B) and the up-regulation of ICAM-1, which was expressed in the endothelium along the vascular wall (FIGS. 4B, 5A). Staining of ileum sections obtained from sham-operated rats with anti-ICAM-1 antibody showed a specific staining along vessels, demonstrating that ICAM-1 is constitutively expressed (FIG. 5A). In addition, ileum sections obtained from SAO-shocked rats at 60 min of reperfusion showed positive staining for nitrotyrosine (FIGS. 5A, 6A) and PAR (FIGS. 5A, 6C). Administration of recHDL reduced the degree of immunostaining for nitrotyrosine (FIG. 5A, 6B) and PAR (FIG. 5A, 6D) in the repressed intestine. No staining for either nitrotyrosine or PAR was observed in sham-operated rats (FIG. 5A). Finally, histological examinations of the small intestine at 60 min post reperfusion (see representative sections in FIG. 7) revealed the following pathological changes: Ileum sections showed inflammatory infiltration by inflammatory cells extending through the wall and concentrated below the epithelial layer (FIG. 7A). recHDL treated rats show a significant reduction in organ injury (FIG. 7B). No histological alterations were observed in sham-treated rats (data not shown).

Protective Effects of HDL in DNBS-Induced Colitis

Figure 8:
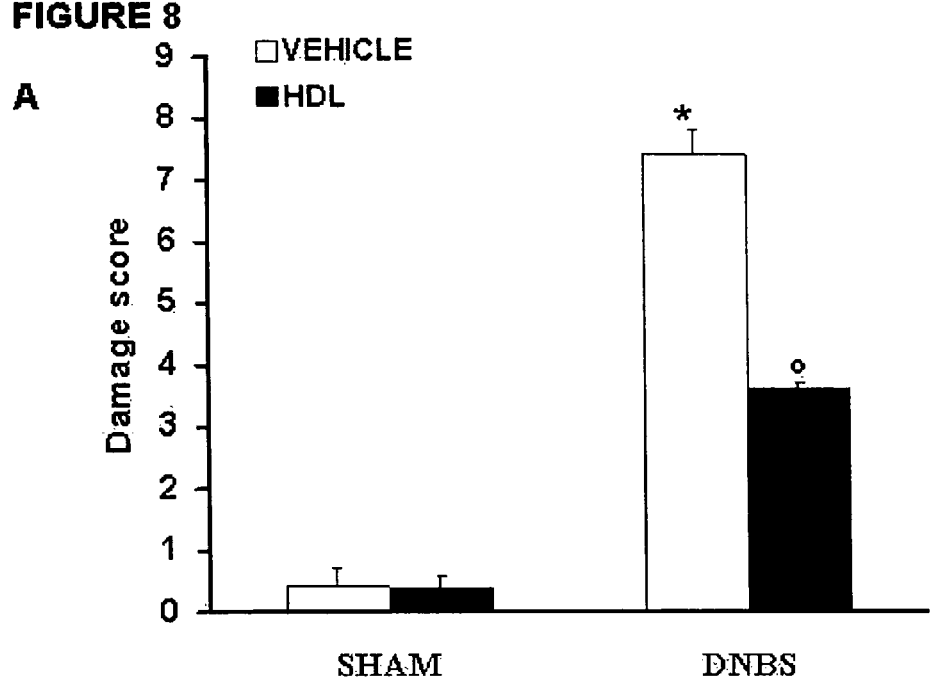
FIG. 8 shows the effect of HDL treatment on the damage score and on colon injury. Colonic damage (A) was scored on a 0 (normal) to 10 (severe) scale by two independent observers. Histological examination of descending colon from DNBS-treated rats (B) reveals a complete alteration of the epithelial layer, muscularis mucosa and submucosal as well as a diffuse inflammatory cells infiltration in perilesional area. Treatment with HDL (C) significantly reduced the damage score (A) and corrected the disturbances in morphology and reduced the inflammatory cells infiltration associated with DNBS administration. Original magnification: ×100. Figure is representative of at least 3 experiments performed on different experimental days. Values are means±S.E.M. of 10 rats for each group. *P<0.01 vs. sham; °P<0.01 vs. DNBS.
Figure 8:
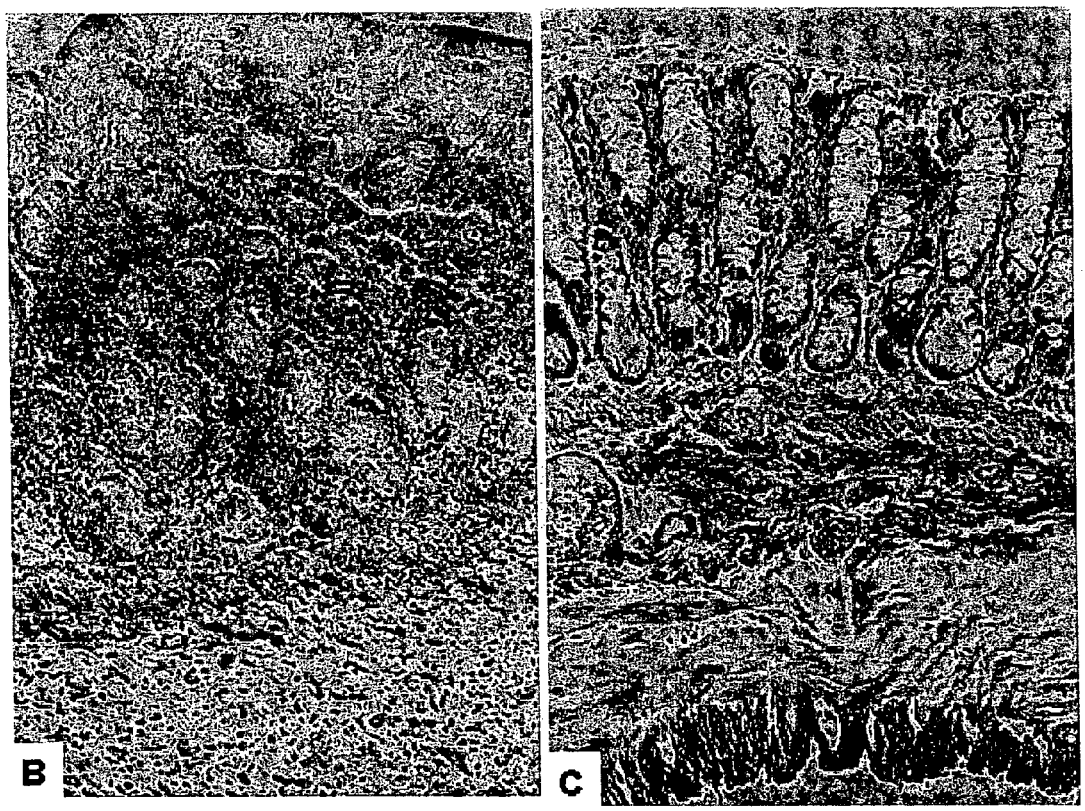
Figure 9:
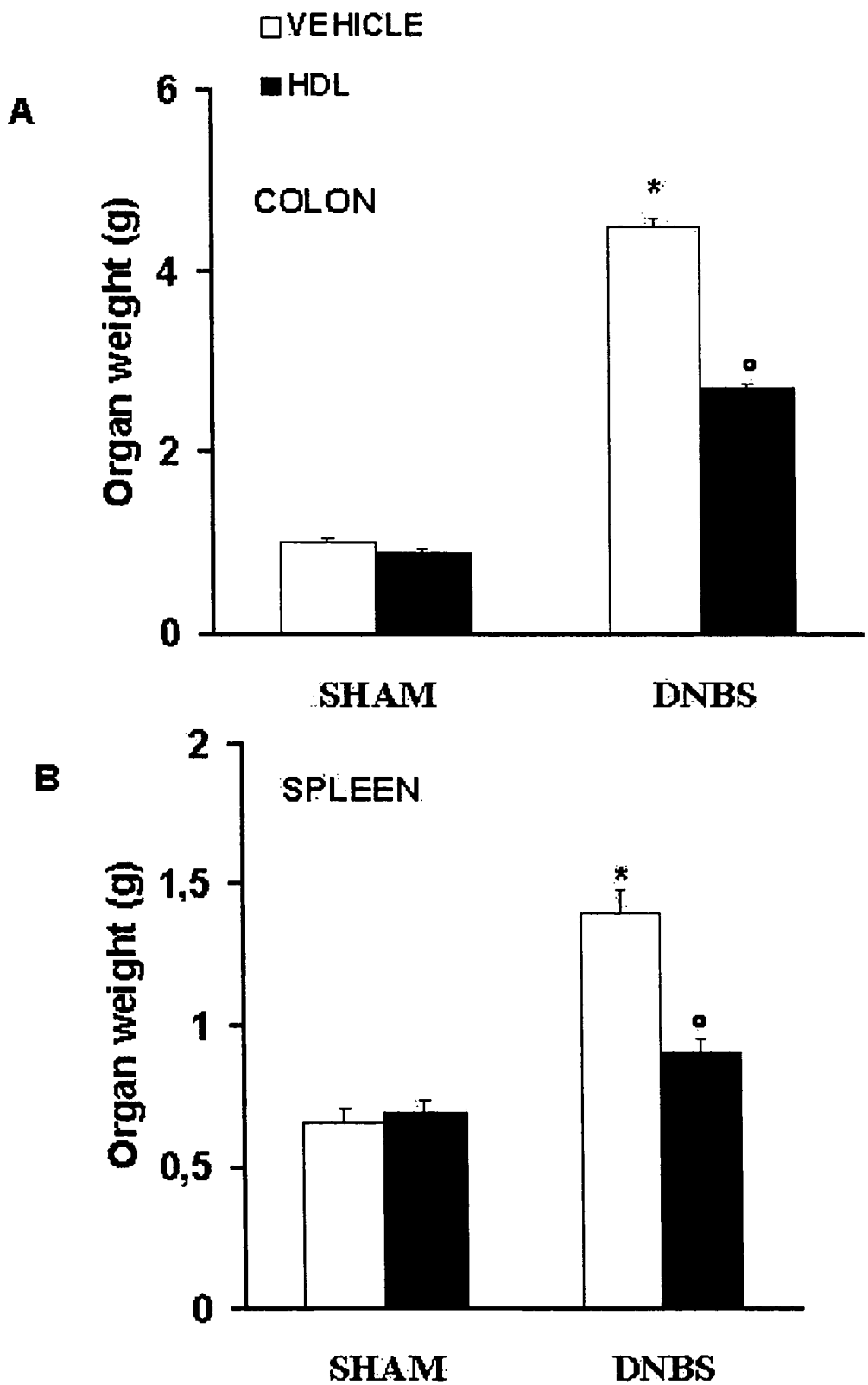
FIG. 9 shows organ weight. A significant increase was consistently seen at 4 days after DNBS injection in colon (A) and spleen (B). The weight of the organs was significantly reduced in the rats which had been treated with HDL. Values are means±s.e. means of 10 rats for each group. *p<0.01 vs. sham; °p<0.01 vs. DNBS.
Figure 10:
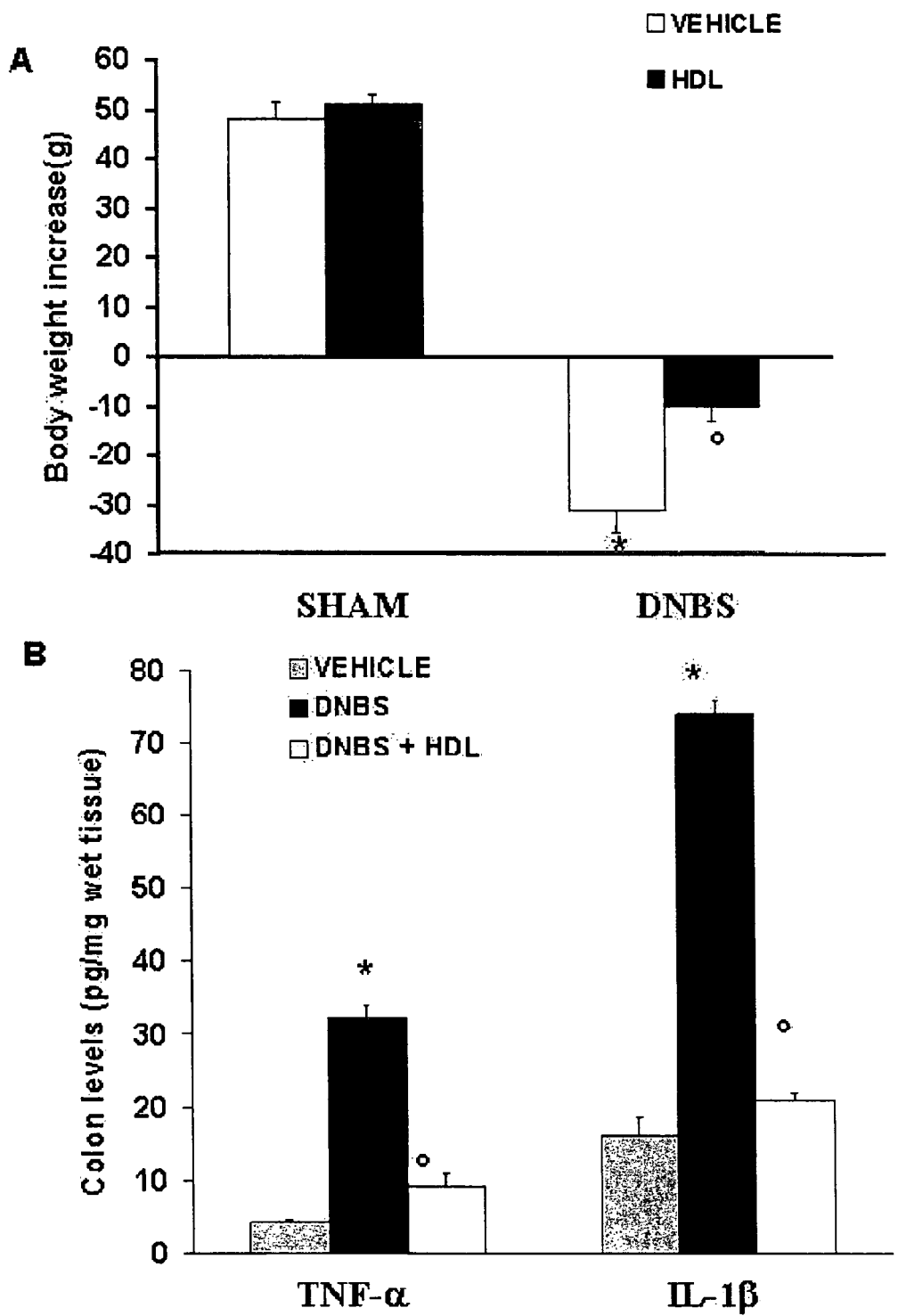
FIG. 10 shows the effect of HDL treatment on body weight changes and TNF-α and IL-1β levels at 4 days after DNBS intracolonic administration. A significant loss of body weight (A) and an increase of TNF-α and IL-1β (B) were observed in the DNBS-treated rats. HDL treatment significantly prevented the loss of body weight and reduced the increase of cytokine levels in the colon. Values are means±S.E.M. of 10 rats for each group. *P<0.01 vs. sham; °P<0.01 vs. DNBS.

Four days after intra-colonic administration of DNBS, the colon appeared flaccid and filled with liquid stool. The macroscopic inspection of cecum, colon and rectum showed presence of mucosal congestion, erosion and haemorrhagic ulcerations (FIG. 8A). The histopathological features included a transmural necrosis and oedema and a diffuse PMN cellular infiltrate in the submucosa (FIG. 8B). The inflammatory changes of the intestinal tract were associated with an increase in the weight of the colon (FIG. 9A). Treatment of rats with recHDL (40 mg/kg/day) significantly attenuated the extent and severity of the histological signs of colon injury (FIGS. 8A, 8C). A significant increase in the weight of the spleen, an indicator of inflammation, was also noted in vehicle-treated rats, which had received DNBS (FIG. 9B). No significant increase in weight of either colon or spleen was observed in DNBS-rats, which had been treated with recHDL (FIG. 9). The severe colitis caused by DNBS was associated with a significant loss in body weight (FIG. 10A). Treatment of DNBS-rats with recHDL significantly reduced the loss in body weight (FIG. 10A). Colonic injury by DNBS administration was also characterised by an increase of pro-inflammatory cytokines (TNF-α, and IL-1β) in the colon (FIG. 10B). recHDL treatment reduced the increase in TNF-α and IL-1β as observed in colonic tissues (FIG. 10B).

Figure 11:
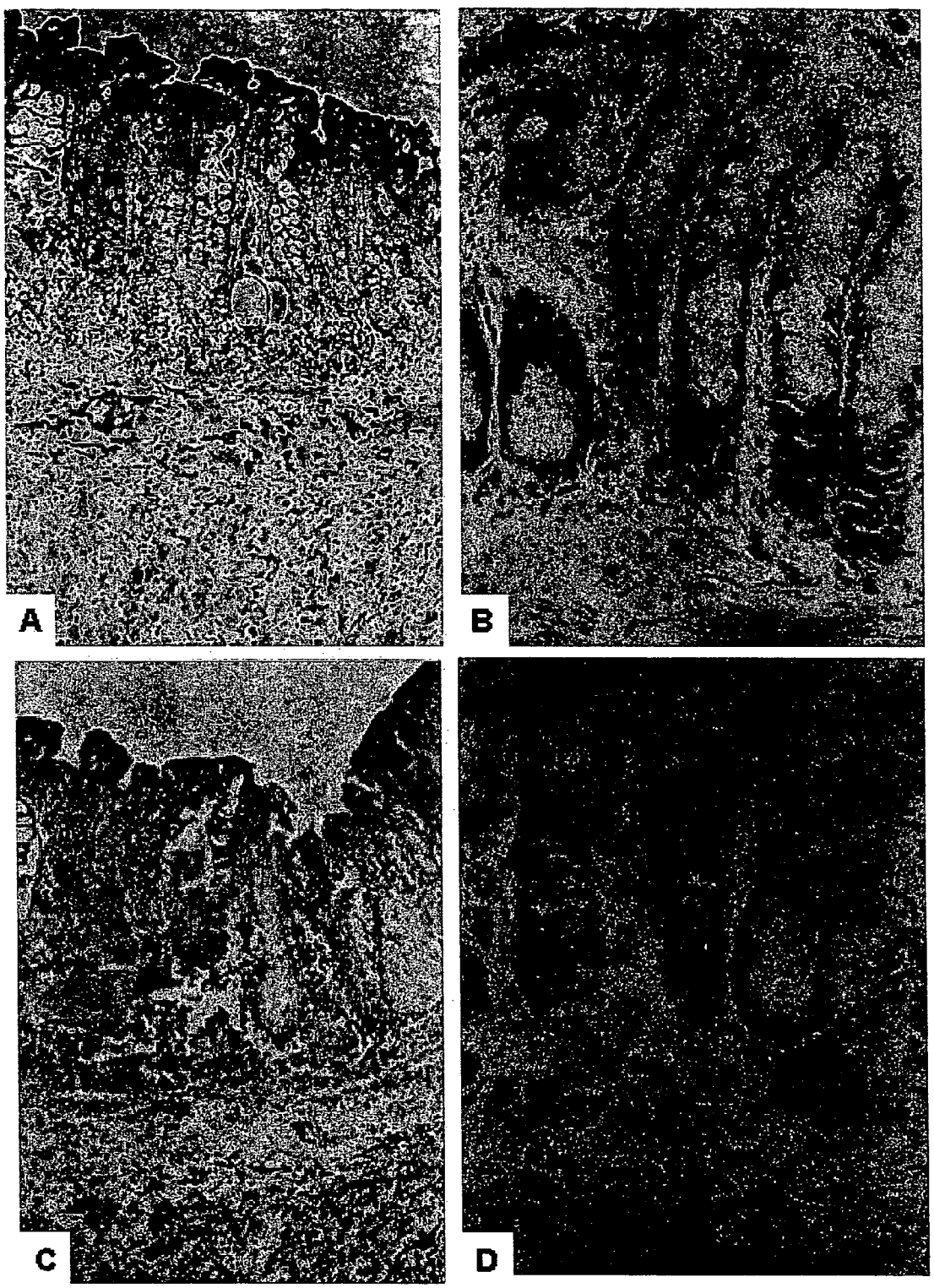
FIG. 11 shows immunohistochemical localisation for nitrotyrosine and for poly (ADP-ribose) in the colon. Immunohistochemical for nitrotyrosine (A) and for poly (ADP-ribose) (C) show positive staining primarily localised in the infiltrated inflammatory cells and in disrupted epithelial cells from a DNBS treated rats. The intensity of the positive staining for nitrotyrosine (B) and for poly (ADP-ribose) (D) was significantly reduced in the colon from HDL-treated rats. Original magnification: ×250. Figure is representative of at least 3 experiments performed on different experimental days.
Figure 12:
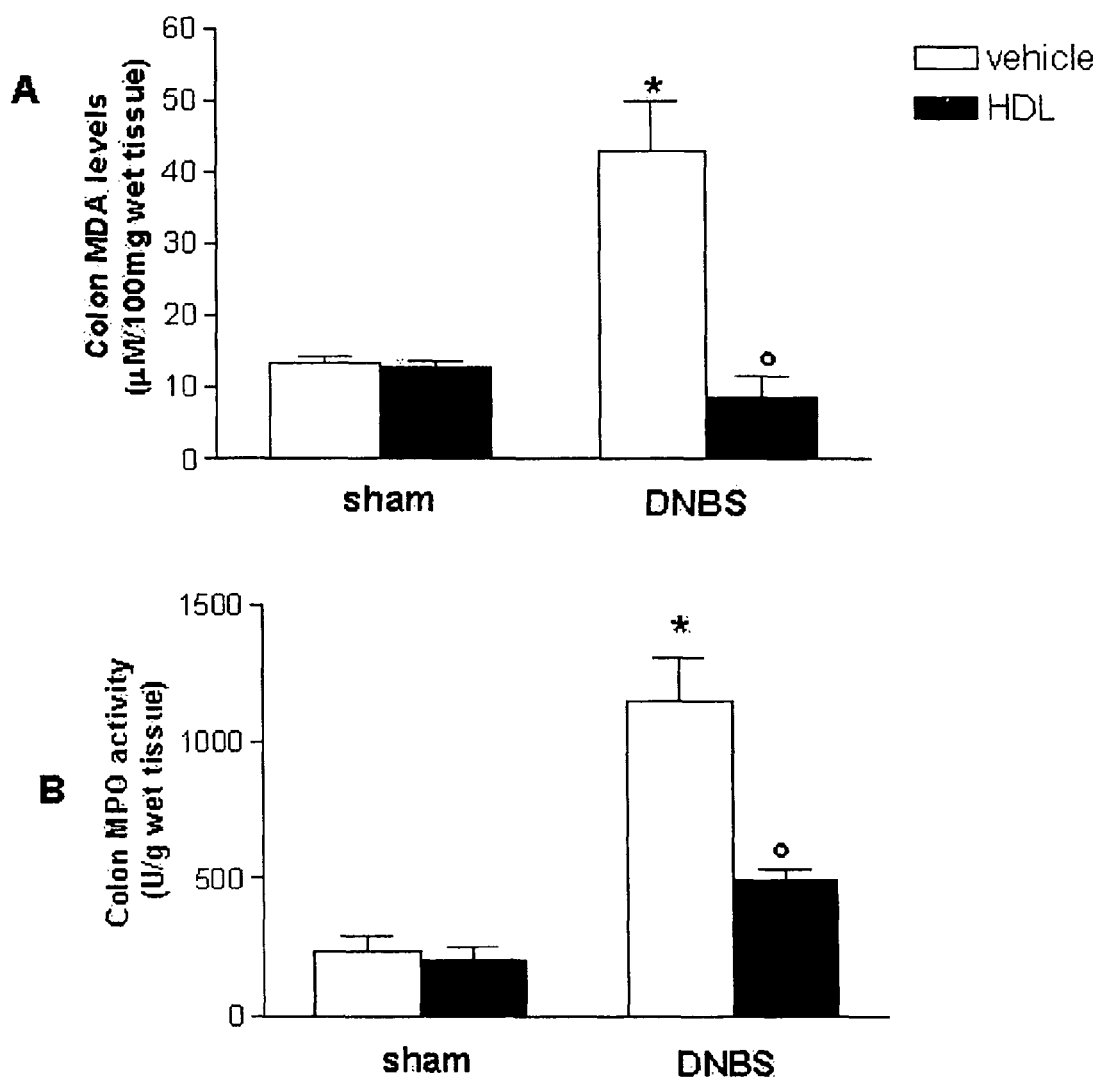
FIG. 12 shows the effect of HDL on neutrophil infiltration and lipid peroxidation. Malondialdehyde (MDA) (A) and myeloperoxidase (MPO) activity (B) in the colon from DNBS-treated rats. MPO activity and MDA levels were significantly increased in DNBS-treated rats in comparison to sham. HDL-treated rats show a significant reduction of MPO activity and MDA levels. Values are means±s.e. means of 10 rats for each group. *p<0.01 vs. sham; °p<0.01 vs. DNBS.
Figure 13:
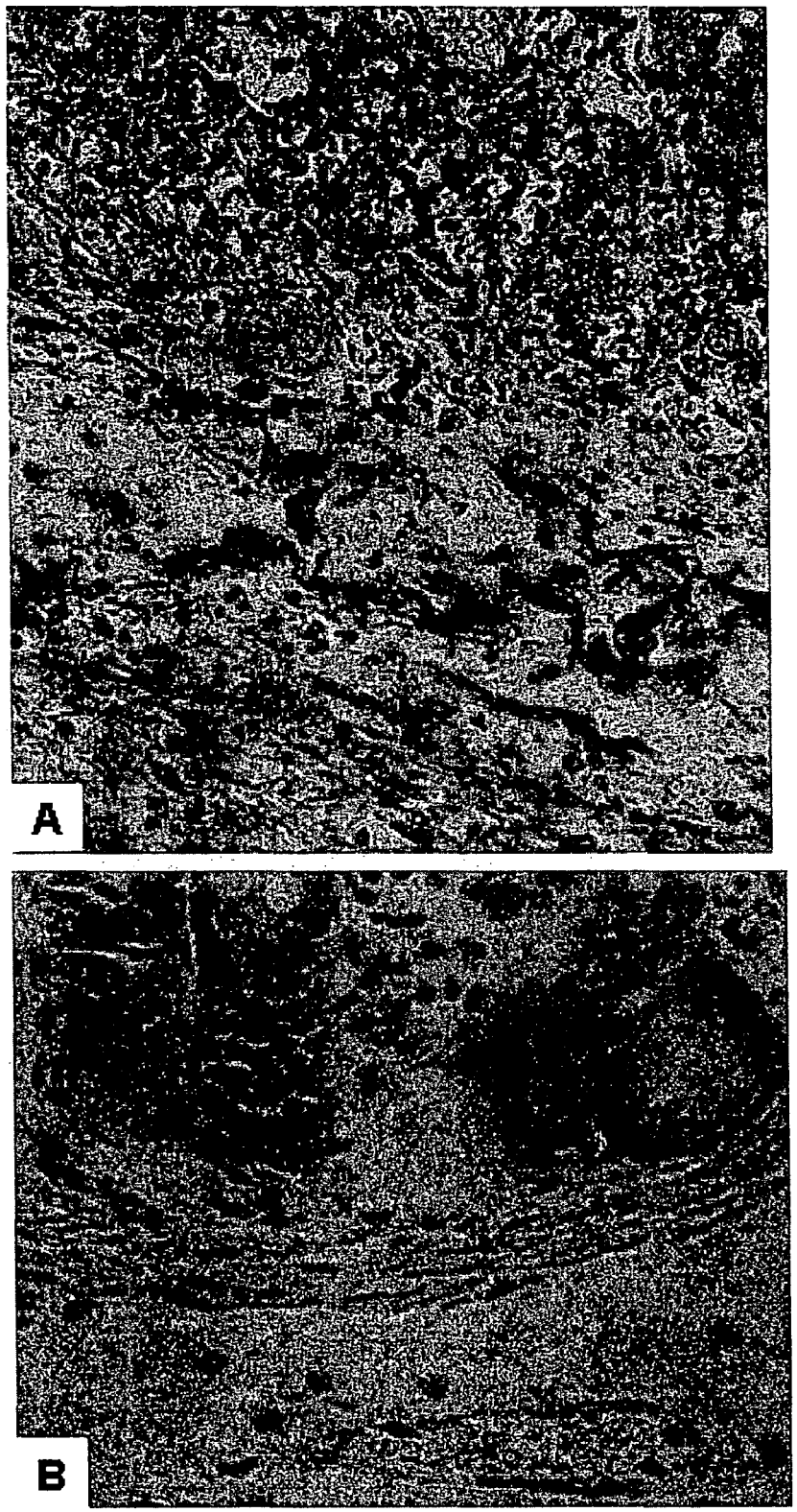
FIG. 13 shows immunohistochemical localisation of ICAM-1 in the colon. Colon section obtained from DNBS-treated rats showed intense positive staining for ICAM-1 (A) on the vessels as well as in inflammatory cells concentrated below the epithelial layer. The degree of positive staining for ICAM-1 (B) was markedly reduced in tissue section obtained from HDL-treated rats. Original magnification: ×250. Figure is representative of at least 3 experiments performed on different experimental days.

At 4 days after DNBS treatment, sections of colon from sham-administered rats did not stain for either nitrotyrosine or PAR (FIG. 5B). Colon sections obtained from vehicle-treated DNBS rats exhibited positive staining for nitrotyrosine (FIG. 11A) and PAR (FIG. 11C), which was localised in inflammatory cells and in disrupted epithelial cells. recHDL treatment reduced the degree of immunostaining for nitrotyrosine (FIG. 11B) and PAR (FIG. 11D) in the colon of DNBS-treated rats. The presence of nitrotyrosine staining in the colon correlated positively with the increase in tissue levels of MDA, indicating an increase in lipid peroxidation (FIG. 12A). recHDL treatment significantly reduced the degree of lipid peroxidation (determined as a decrease in tissue MDA levels, FIG. 12A). The colitis caused by DNBS was also characterised by an increase in MPO activity (FIG. 12B). This finding is consistent with the observation made with light microscopy that the colon of vehicle-treated DNBS rats contained a large number of PMNs. Infiltration of PMNs into the mucosa has been suggested to contribute significantly to the tissue necrosis and mucosal dysfunction associated with colitis, as activated PMNs release large amounts of free radicals. To further elucidate the effect of recHDL treatment on PMN accumulation in the inflamed colon, we next evaluated the intestinal expression of ICAM-1. Tissue sections obtained from sham-operated rats with anti-ICAM-1 antibody showed a specific staining along the vessels, demonstrating that ICAM-1 is expressed constitutively in endothelial cells (FIG. 5B). After DNBS administration, the staining intensity substantially increased in the vessels of the lamina propria and submucosa. Immunohistochemical staining for ICAM-1 was also present in epithelial cells of injured colon and in infiltrated inflammatory cells in damaged tissues from DNBS-treated rats (FIG. 13B). Treatment of DNBS-rats with recHDL, however, significantly reduced both the degree of PMN infiltration (determined as a decrease in MPO activity, FIG. 12B) and the up-regulation of the constitutive ICAM-1, which was normally expressed in the endothelium along the vascular wall (FIG. 13B).

Discussion

This study provides evidence that treatment of rats with recHDL attenuates: (i) the development of SAO shock, (ii) the infiltration of the ileum with PMNs (histology and MPO activity), (iii) the degree of lipid peroxidation in the ileum, and (iv) the degree of ileum injury (histology) caused by ischaemia and reperfusion; (v) the development of DNBS-induced colitis, (vi) the infiltration of the colon with PMNs (histology and MPO activity), (vii) the degree of lipid peroxidation in the colon, and (viii) the degree of colon injury (histology) in rats treated with DNBS. All of these findings support the view that recHDL attenuates the degree of gut inflammation in the rat.

HDL Reduces Oxidative and Nitrosative Damage Associated with Gut Ischaemia and with DNBS-Induced Colitis Reactive oxygen and nitrogen species play a key role in gut injury associated with I/R (12,13,30) and with IBD (14,31). The important contribution to the pathophysiology of IBD of reactive oxygen or nitrogen species has been demonstrated in both animal and clinical studies. These species are cytotoxic agents, inducing lipid peroxidation and other cellular oxidative stress by cross linking proteins, lipids, and nucleic acids, which then cause cellular dysfunction, damage, and eventually death. Evidence consistent with damage caused by reactive radical species is provided by a large number of animal and clinical studies (12,13,30,31). In the present study, it has been found that the intestinal damage induced either by I/R or by intra-colonic administration of DNBS was associated with high concentrations of MDA, which is considered a good indicator of lipid peroxidation (29). Recent evidence indicates that nitration of tyrosine can result from a number of chemical actions, and can be considered as a global marker of nitrosative stress (32). Nitrotyrosine can be formed from the reaction of nitrite with hypochlorous acid or the reaction of nitrite with MPO and hydrogen peroxide (33). In these experiments, increased immunohistochemical expression of nitrotyrosine has been found mostly localised on epithelial cells and in the area of infiltrated inflammatory cells, suggesting that peroxynitrite or other nitrogen derivatives and oxidants are formed in vivo and may contribute to tissue injury. These data are consistent with previous findings that immunohistochemical staining for nitrotyrosine was localised on inflammatory cells during DNBS-induced colitis (34) and during SAO-shock (13,27). The pathogenic role of nitrogen derived species such as peroxynitrite (35) in gut inflammation is further supported by the fact that intra-colonic administration of exogenous peroxynitrite induces a severe colonic inflammation, which mimics the features of both ulcerative colitis and Crohn's disease. In the present study it was observed that ileum and colon injury was significantly less in rats treated with recHDL. Indeed, HDL treatment prevented the formation of tissue MDA and nitrotyrosine staining in SAO-shocked rats and DNBS-treated animals. ROS [reactive oxygen species] cause single-strand damage, leading to PARP activation and cell death (36). Some evidence exists to support the possible role of PARP activation in the pathophysiology of gut inflammation (37). recHDL treatment reduced PAR formation, an index of PARP activation, and this effect may well contribute to the overall protective effects of HDLs observed in these studies.

The Beneficial Effect of HDLs in SAO-Shock and in DNBS-Induced Colitis is Related to an Inhibition of Cytokines Production TNF-α and IL-1β are clearly involved in the pathogenesis of I/R and colitis and these cytokines are present in the colon during inflammation (13,27,38). Direct evidence that TNF-α and IL-1β play a role in the pathogenesis of experimental colitis and SAO-shock has been obtained in animal models in which blocking of the action of these cytokines has been shown to delay the onset of gut injury and suppress the associated inflammatory response (13,27). A role for TNF-α in human disease came from recent studies using Infliximab (38), a chimeric anti-TNF antibody, and CDP571, a humanised monoclonal antibody to TNF-α, and membrane-bound TNF without fixing complement nor mediating antibody-dependent cellular cytotoxicity (40). In both cases, significant reduction in Crohn's disease activity index (CDAI) as well as attenuation of histopathological and endoscopic inflammation in Crohn's disease patients was observed.

As the present study demonstrates that recHDL significantly reduces the release of TNF-α and IL-1β associated with SAO-shock and with DNBS-induced colitis, and without wishing to be bound by any one theory, it is postulated by the present inventors that the inhibition of the formation of TNF-α and IL-1β plays an important role in the overall beneficial effects observed with HDL. These results are in agreement with previous observations, which show that HDL also attenuates the release of pro-inflammatory cytokines (including TNF-α) caused by small doses of intravenously administered LPS (10).

The Beneficial Effects of HDL in SAO-Shock and in DNBS-Induced Colitis are Related to an Alteration in PMN Recruitment.

PMNs play a crucial role in the development and full manifestation of gastrointestinal inflammation, as they represent a major source of free radicals in the inflamed intestinal mucosa (41). PMN infiltration into inflamed tissues plays a crucial role in the destruction of foreign antigens and in the breakdown and remodelling of injured tissue (42). The interactions of PMNs with the endothelium are regulated by various adhesion molecules including the selectins, the Beta2 integrins and adhesion molecules of the immunoglobulin superfamily (43). A firm adherence of the PMN to the endothelial surface is required for transendothelial migration (21). This firm adherence involves the interaction of Beta2 integrins (i.e., CD11/CD18) on the PMN surface and ICAM-1 on the endothelial cell surface (44).

A major finding of this study was that, not only did the recHDL-treated rats show a remarkable recovery of the intestinal injury associated with a reduction in oxidative and nitrosative damage after I/R as well as after DNBS administration, but also in recHDL-treated rats, infiltration of PMNs into the colon was significantly reduced. Furthermore, ICAM-1 was expressed in endothelial and epithelial cells, and PMNs both in the ileum from SAO-shocked rats and in the distal colon from DNBS-treated rats. recHDL treatment was associated with a significant reduction of ICAM-1 expression in endothelial and epithelial cells. These results clearly demonstrate that recHDLs can interrupt the cascade of events leading to the interaction between PMNs and endothelial cells in the late firm adhesion phase mediated by ICAM-1, and these findings are in agreement with other previously published studies (9,10).

CONCLUSIONS

These results clearly demonstrate that recHDLs are protective in SAO-shock and in experimental colitis, and that inhibition of TNF-α and IL-1β formation (amongst other effects which include inhibition of PMN infiltration) in the injured tissue probably accounts for the beneficial effects.

REFERENCES

1. Cockerill G W, Reed S: High-density lipoprotein: Multipotent effects on cells of the vasculature. *Int. Rev. Cytol.* 188: 257-297, 1999.
2. Nanjee M N, Doran J E, Lerch P G, Miller N E: Acute effects of intravenous infusion of apolipoprotein A-I/phosphatidylcholine discs on plasma lipoproteins in human. *Arterioscler. Thromb. Vasc. Biol.* 19: 979-989, 1999.
3. Gordon D J, Probsfield J L, Garrison R J: High density lipoprotein cholesterol and cardiovascular disease: four prospective American studies, *Circulation* 79:8-15, 1989.
4. Paszty C., Maeda N., Verstuyft J., Rubin, E. M., Apolipoprotein A1 transgene corrects apoliproprotein E-deficiency-induced atherosclerosis in mice. *J. Clin. Invest.* 94:899-903, 1994.
5. Tangirala R K, Tsukamoto K, Chun S H, Usher D, Pure E, Rader D J: Regression of atherosclerosis induced by liver-directed gene transfer of apolipoprotein A-1 in mice. *Circulation* 100: 1816-1822, 1999.
6. McDonald M C, Dhadly P, Cockerill G W, Cuzzocrea S, Mota-Filipe H, Hinds C J, Miller N E, Thiemermann C. Reconstituted High-Density Lipoprotein Attenuates Organ Injury and Adhesion Molecule Expression in a Rodent Model of Endotoxic Shock. *Shock.* 20: 551-557, 2003.
7. Cockerill G W, McDonald M C, Mota-Filipe H, Cuzzocrea S, Miller N E, Thiemermann C: High density lipoproteins reduce organ injury and organ dysfunction in a rat model of haemorrhagic shock. *FASEB J.* 15: 1941-1952, 2001.
8. Van Leeuwen H J, van Beek A P, Dallinga-Thie G M, van Strijp J A, Verhoef J, van Kessel K P: The role of high density lipoprotein in sepsis. *Neth. J. Med.* 59: 102-110, 2001.
9. Cockerill G W, Huehns T Y, Weerasinghe A., Stocker C., Lerch P G, Miller N E, Haskard D O: Eleation of plasma high-density lipoprotein concentration reduces interleukin-1-induced expression of E-selectin in an in vivo model of acute inflammation. *Circulation* 103: 108-112, 2001.
10. Pajkrt D, Doran J E, Koster F, Lerch P G, Arnet B, van der Poll T, ten Cate J W, van Deventer S J: Antiinflammatory effects of reconstituted high-density lipoprotein during human endotoxaemia. *J. Exp. Med.* 184: 1601-1608, 1996.

11. Thiemermann C, Patel N S A, Kvale E O, Cockerill G W, Brown P A, Stewart K N, Cuzzocrea S, Britti D, Mota-Filipe H, Chatterjee P K: High density lipoprotein (HDL) reduces renal ischaemia/reperfusion injury. *J. Am. Soc. Nephrol.* 14: 1833-43, 2003.
12. Cuzzocrea S, Riley D P, Caputi A P, Salvemini D: Antioxidant therapy: a new pharmacological approach in shock, inflammation, and ischaemia/reperfusion injury. *Pharmacol. Rev.* 53: 135-59, 2001.
13. Cuzzocrea S, Chatterjee P K, Mazzon E, Dugo L, De Sarro A, Van de Loo F A, Caputi A P, Thiemermann C. Role of induced nitric oxide in the initiation of the inflammatory response after postischemic injury. *Shock.* 18: 169-76, 2002.
14. Cuzzocrea S, Mazzon E, Dugo L, Caputi A P, Riley D P, Salvemini D: Protective effects of M40403, a superoxide dismutase mimetic, in a rodent model of colitis. *Eur. J. Pharmacol.* 432: 79-89, 2001.
15. Parks D A: Oxygen radicals: mediators of gastrointestinal pathophysiology. *Gut* 30: 293-298, 1989.
16. Kitahora, T., Suzuki, K., Asakura, H., Yoshida, T., Suematsu, M., Watanabe, M., Aiso, S., Tsuchiya, M. (1988) Active oxygen species generated by monocytes and polymorphonuclear cells in Crohn's disease. *Dig. Dis. Sci.* 33, 951-955.
17. Mahida Y R, Wu K C, Jewell D P: Respiratory burst activity of intestinal macrophages in normal and inflammatory bowel disease. *Gut* 30: 1362-1370, 1989.
18. Verspaget H W, Pena A S, Weterman I T, Lamers C B: Diminished neutrophil function in Crohn's disease and ulcerative colitis identified by decreased oxidative metabolism and low superoxide dismutase content. *Gut* 29: 223-228, 1988.
19. Crama-Bohbouth G E, Arndt J W, Pena A S, Verspaget H W, Tjon A Tham R T, Weterman I T, Pauwels E K, Lamers C B: Value of indium-111 granulocyte scintigraphy in the assessment of Crohn's disease of the small intestine: prospective investigation. *Digestion* 40: 227-236, 1988.
20. Grisham M B, Granger D N, Neutrophil-mediated mucosal injury. Role of reactive oxygen metabolites. *Dig. Dis. Sci.* 33: 6-15, 1988.
21. Butcher E C: Specificity of leukocyte-endothelial interactions and diapedesis: physiologic and therapeutic implications of an active decision process. *Res. Immunol.* 144: 695-698, 1993.
22. Wertheimer S J, Myers C L, Wallace R W, Parks T P: Intercellular adhesion molecule-1 gene expression in human endothelial cells. *J. Biol. Chem.* 267: 12030-12035, 1992.
23. Wallace J L, Keenan C M, Gale D, Shoupe T S: Exacerbation of experimental colitis by nonsteroidal anti-inflammatory drugs is not related to elevated leukotriene B4 synthesis. *Gastroenterology* 102: 18-27, 1992.
24. Matz, C. E., Jonas, A. Micellar complexes of human apolipoprotein A-I with phosphatidylcholines and cholesterol prepared from cholate-lipid dispersion. *J. Biol. Chem.* 257: 4535-4540, 1982.
25. Lerch, P. G., Fortsch, V., Hodler, G., Bolli, R. Production and characterisation of a reconstituted high-density lipoprotein for therapeutic applications. *Vox Sang* 71: 155-164, 1996.
26. Morris G P, Beck P L, Herridge M S, Depew W T, Szewczuk M R, Wallace J L: Hapten induced model of chronic inflammation and ulceration in the rat. *Gastroenterology* 96: 795-803, 1989.
27. Cuzzocrea S, Misko T P, Costantino G, E Micali A, Caputi A P, Macarthur H, Salvemini D: Beneficial effects of peroxynitrite decomposition catalyst in a rat model of splanchnic artery occlusion and reperfusion. *FASEB J.* 14: 1061-72, 2000.
28. Mullane K M, Kraemer R, Smith B: Myeloperoxidase activity as a quantitative assessment of neutrophil infiltration into ischaemic myocardium. *J. Pharmacol. Meth.* 14: 157-167, 1985.
29. Ohkawa H, Ohishi N, Yagi K: Assay for lipid peroxides in animal tissues by thiobarbituric acid reaction. *Anal. Biochem.* 95: 351-358, 1979.
30. Cuzzocrea S, McDonald M C, Mazzon E, Filipe H M, Costantino G, Caputi A P, Thiemermann C. Beneficial effects of tempol, a membrane-permeable radical scavenger, in a rodent model of splanchnic artery occlusion and reperfusion. *Shock.* 14: 150-6, 2000.
31. Grisham M B: Oxidants and free radicals in inflammatory bowel disease. *Lancet* 344: 859-861, 1994.
32. Halliwell B: What nitrates tyrosine? Is nitrotyrosine specific as a biomarker of peroxynitrite formation in vivo? *FEBS Lett.* 411: 157-160, 1997.
33. Eiserich J P, Hristova M, Cross C E, Jones A D, Freeman B A, Halliwell B, van der Vlie A: Formation of nitric oxide-derived inflammatory oxidants by myeloperoxidase in neutrophils. *Nature* 391, 393-397, 1998.
34. Cuzzocrea S, McDonald M C, Mazzon E, Mota-Filipe H, Centorrino T, Terranova M L, Ciccolo A, Britti D, Caputi A P, Thiemerman C: Calpain inhibitor I reduces colon injury caused by dinitrobenzene sulphonic acid in the rat. *Gut* 48: 478-88, 2001.
35. Ischiropoulos H, Zhu L, Beckman J S: Peroxynitrite formation from microphage-derived nitric oxide. *Arch. Biochem. Biophys.* 298: 446-451, 1992.
36. Szabó C, Dawson V L: Role of poly(ADP-ribose) synthetase in inflammation and ischaemiareperfusion. *Trends Pharmacol. Sci.* 19: 287-298, 1998.
37. Mazzon E, Dugo L, De S A, Li J H, Caputi A P, Zhang J, Cuzzocrea S. Beneficial effects of GPI 6150, an inhibitor of poly(ADP-ribose) polymerase in a rat model of splanchnic artery occlusion and reperfusion. *Shock.* 17: 222-7, 2002.
38. Grotz M R, Ding J, Guo W, Huang Q, Deitch E A. Comparison of plasma cytokine levels in rats subjected to superior mesenteric artery occlusion or haemorrhagic shock. *Shock.* 3: 362-8, 1995.
39. Present D H, Rutgeerts P, Targan S, S B Mayer L, van Hogez and R A, Podolsky D K, Sands B E, Braakman T, DeWoody K L, Schaible T F, van Deventer S J: Infliximab for the treatment of fistulas in patients with Crohn's disease. *N. Engl. J. Med.* 340: 1398-1405, 1999.
40. Stack W A, Mann S D, Roy A J, Heath P, Sopwith M, Freeman J, Holmes G, Long R, Forbes A, Kamm M A: Randomized controlled trial of CDP571 antibody to tumor necrosis factor-alpha in Crohn's disease. *Lancet* 349: 521-524, 1997.
41. Grisham M B: Oxidants and free radicals in inflammatory bowel disease. *Lancet* 344: 859-861, 1994.
42. Lefer A M, Lefer D J: Pharmacology of the endothelium in ischaemia-reperfusion and circulatory shock. *Ann. Rev. Pharmacol. Toxicol.* 33: 71-90, 1993.
43. Geng J G, Bevilacqua M P, Moore K L: Rapid neutrophil adhesion to activated endothelium mediated by GMP-140. *Nature* 343: 757-760, 1990.
44. Koizumi M, King N, Lobb R, Benjamin C, Podolsky D K: Expression of vascular adhesion molecules in inflammatory bowel. *Gastroenterology* 103: 840-847, 1992.

The invention claimed is:

1. A method for the treatment of ischaemia/reperfusion (I/R) injury of the intestine, inflammatory bowel disease, acute infective colitis or pseudomembranous colitis of a patient, which comprises parenteral administration to said patient of an effective amount of high density lipoprotein.

2. The method of claim 1, wherein said patient is a human.

3. The method of claim 1, wherein said HDL is selected from the group consisting of nascent HDL, reconstituted HDL, and recombinant HDL.

4. The method of claim 3, wherein said HDL is reconstituted HDL.

5. The method of claim 1, wherein said HDL is administered in a dosage range of from 0.1-200 mg per kg body weight of the patient per treatment, preferably in a dosage range of from 10-80 mg per kg body weight per treatment.

6. The method of claim 1, wherein said parenteral administration is selected from the group consisting of intravenous, intraarterial, intramuscular and subcutaneous injection or infusion.

7. The method of claim 6, wherein said parenteral administration is intravenous injection or infusion.

8. The method of claim 3, wherein said HDL is nascent HDL.

9. The method of claim 3, wherein said HDL is recombinant HDL.

10. The method of claim 1, wherein said patient has ischaemia/reperfusion (I/R) injury of the intestine.

11. The method of claim 1, wherein said patient has inflammatory bowel disease.

12. The method of claim 1, wherein said HDL is an HDL analogue comprising:

(i) a 22 to 29-residue peptide or peptide analogue which forms an amphipathic α helix in the presence of lipids and which comprises formula (I):

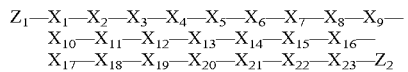

(I)

or a pharmaceutically acceptable salt thereof, wherein:

$X_1$ is Pro (P), Ala (A), Gly (G), Gln (O), Asn (N), Asp (D) or D-Pro (p);

$X_2$ is an aliphatic residue;

$X_3$ is Leu (L) or Phe (F);

$X_4$ is an acidic residue;

$X_5$ is Leu (L) or Phe (F);

$X_6$ is Leu (L) or Phe (F);

$X_7$ is a hydrophilic residue;

$X_8$ is an acidic or a basic residue;

$X_9$ is Leu (L) or Gly (G);

$X_{10}$ is Leu (L), Trp (W) or Gly (G);

$X_{11}$ is a hydrophilic residue;

$X_{12}$ is a hydrophilic residue;

$X_{13}$ is Gly (G) or an aliphatic residue;

$X_{14}$ is Leu (L), Trp (W), Gly (G) or NaI;

$X_{15}$ is a hydrophilic residue;

$X_{16}$ is a hydrophobic residue;

$X_{17}$ is a hydrophobic residue;

$X_{18}$ is Gln (O), Asn (N) or a basic residue;

$X_{19}$ is Gln (O), Asn (N) or a basic residue;

$X_{20}$ is a basic residue;

$X_{21}$ is an aliphatic residue;

$X_{22}$ is a basic residue;

$X_{23}$ is absent or a basic residue;

$Z_1$ is $H_2N$— or RC(O)NH—;

$Z_2$ is —C(O)NRR, —C(O)OR or —C(O)OH or a salt thereof;

each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl or a 1 to 7-residue peptide or peptide analogue in which one or more bonds between residues 1-7 are independently a substituted amide, an isostere of an amide or an amide mimetic; and each "—" between residues $X_1$ through $X_{23}$ independently designates an amide linkage, a substituted amide linkage, an isostere of an amide or an amide mimetic; or (ii) an altered form of formula (I) in which at least one of residues $X_1$, $X_2$, $X_3$, $X_4$, $X_5$, $X_6$, $X_7$, $X_8$, $X_9$, $X_{10}$, $X_{11}$, $X_{12}, X_{13}, X_{14}, X_{15}, X_{16}, X_{17}, X_{18}, X_{19}, X_{20}, X_{21}, X_{22}, X_{23}$ is conservatively substituted with another residue.

13. The method of claim 1, wherein said HDL is an HDL analogue comprising:
(i) an 18 to 22-residue peptide or peptide analogue which forms an amphipathic α helix in the presence of lipids and which comprises formula (II):

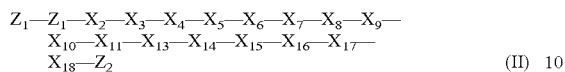
(II)

or a pharmaceutically acceptable salt thereof, wherein:
$X_1$ is Pro (P), Ala (A), Gly (G), Gln (O), Asn (N), or D-Pro (p);
$X_2$ is an aliphatic amino acid;
$X_3$ is Leu (L);
$X_4$ is an acidic amino acid;
$X_5$ is Leu (L) or Phe (F);
$X_6$ is Leu (L) or Phe (F);
$X_7$ is a basic amino acid;
$X_8$ is an acidic amino acid;
$X_9$ is Leu (L) or Trp (W);
$X_{10}$ is Leu (L) or Trp (W);
$X_{11}$ is an acidic amino acid or Asn (N);
$X_{12}$ is an acidic amino acid;
$X_{13}$ is Leu (L), Trp (W) or Phe (F);
$X_{14}$ is a basic amino acid or Leu (L);
$X_{15}$ is Gln (O) or Asn (N);
$X_{16}$ is a basic amino acid;
$X_{17}$ is a Leu (L);
$X_{18}$ is a basic amino acid;
$Z_1$ is $H_2N$— or RC(O)NH—;
$Z_2$ is —C(O)NRR, —C(O)OR or —C(O)OH or a salt thereof;
each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl or a 1 to 4-residue peptide or peptide analogue in which one or more bonds between residues 1-7 are independently a substituted amide, an isotere of an amide or an amide mimetic; and
each "—" between residues $X_1$ through $X_{18}$ independently designates an amide linkage, a substituted amide linkage, an isostere of an amide or an amide mimetic; or
(ii) an altered form of formula (II) in which at least one of residues $X_1, X_2, X_3, X_4, X_5, X_6, X_7, X_8, X_9, X_{10}, X_{11}, X_{12}, X_{13}, X_{14}, X_{15}, X_{16}, X_{17}$, or $X_{18}$ is conservatively substituted with another residue.

14. The method of claim 1, wherein said HDL is an HDL analogue comprising:
a 15 to 22-residue peptide or peptide analogue which forms an amphipathic α-helix in the presence of lipids and which comprises formula (II):

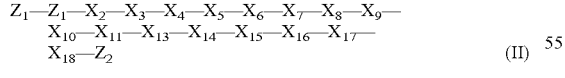
(II)

or a pharmaceutically acceptable salt thereof; wherein
$X_1$ is Pro (P), Ala (A), Gly (G), Gln (O), Asn (N), or D-Pro (p);
$X_2$ is an aliphatic amino acid;
$X_3$ is Leu (L);
$X_4$ is an acidic amino acid;
$X_5$ is Leu (L) or Phe (F);
$X_6$ is Leu (L) or Phe (F);
$X_7$ is a basic amino acid;
$X_8$ is an acidic amino acid;
$X_9$ is Leu (L) or Trp (W);

$X_{10}$ is Leu (L) or Trp (W);
$X_{11}$ is an acidic amino acid or Asn (N);
$X_{12}$ is an acidic amino acid;
$X_{13}$ is Leu (L), Trp (W) or Phe (F);
$X_{14}$ is a basic amino acid or Leu (L);
$X_{15}$ is Gln (O) or Asn (N);
$X_{16}$ is a basic amino acid;
$X_{17}$ is a Leu (L);
$X_{18}$ is a basic amino acid;
$Z_1$ is $H_2N$— or RC(O)NH—;
$Z_2$ is —C(O)NRR, —C(O)OR or —C(O)OH or a salt thereof;
each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl or a 1 to 4-residue peptide or peptide analogue;
each "—" between residues $X_1$ through $X_{18}$ independently designates an amide linkage, a substituted amide linkage, an isostere of an amide or an amide mimetic; and
(ii) up to eight of residues $X_1, X_2, X_3, X_4, X_5, X_6, X_7, X_8, X_9, X_{10}, X_{11}, X_{12}, X_{13}, X_{14}, X_{15}, X_{16}, X_{17}$, or $X_{18}$ are optionally deleted.

15. The method of claim 1, wherein said HDL is an HDL analogue comprising:
(i) a 15 to 26-residue peptide or peptide analogue which forms an amphipathic α-helix in the presence of lipids and exhibits at least about 38% LCAT activation activity as compared with human APOA-I wherein the peptide or peptide analogue comprises a variant of formula (I) wherein one or two helical turns are deleted from formula (I), wherein a helical turn consists of 3 to 4 consecutive residues selected from residues $X_1$ to $X_{23}$ of formula (I):

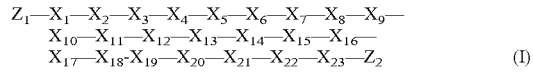
(I)

or a pharmaceutically acceptable salt thereof, wherein:
$X_1$ is Pro (P), Ala (A), Gly (G), Gln (O), Asn (N), Asp (D) or D-Pro (p);
$X_2$ is an aliphatic residue;
$X_3$ is Leu (L) or Phe (F);
$X_4$ is an acidic residue;
$X_5$ is Leu (L) or Phe (F);
$X_6$ is Leu (L) or Phe (F);
$X_7$ is a hydrophilic residue;
$X_8$ is an acidic or a basic residue;
$X_9$ is Leu (L) or Gly (G);
$X_{10}$ is Leu (L), Trp (W) or Gly (G);
$X_{11}$ is a hydrophilic residue;
$X_{12}$ is a hydrophilic residue;
$X_{13}$ is Gly (G) or an aliphatic residue;
$X_{14}$ is Leu (L), Trp (W), Gly (G) or NaI;
$X_{15}$ is a hydrophilic residue;
$X_{16}$ is a hydrophobic residue;
$X_{17}$ is a hydrophobic residue;
$X_{18}$ is Gln (O), Asn (N) or a basic residue;
$X_{19}$ is Gln (O), Asn (N) or a basic residue;
$X_{20}$ is a basic residue;
$X_{21}$ is an aliphatic residue;
$X_{22}$ is a basic residue;
$X_{23}$ is absent or a basic residue;
$Z_1$ is $H_2N$— or RC(O)NR'—;
$Z_2$ is —C(O)NRR, —C(O)OR or —C(O)OH or a salt thereof;
each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl or a 1 to 7-residue peptide or peptide analogue in which one or more bonds between residues 1-7 are independently a substituted amide, an isotere of an amide or an amide mimetic; and each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl; and each "—" between residues $X_1$ through $X_{23}$ independently designates an amide linkage, a substituted amide linkage, an isotere of an amide or an amide mimetic; or an N-terminally blocked form, a C-terminally blocked form, or an N- and C-terminally blocked form of formula (I).

16. The method of claim 1, wherein said HDL is an HDL analogue comprising:

(i) an 18 to 22-residue peptide or peptide analogue which forms an amphipathic α-helix in the presence of lipids and which comprises formula (II):

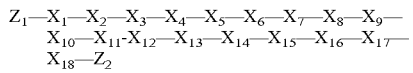

or a pharmaceutically acceptable salt thereof, wherein:

$X_1$ is Pro (P), Ala (A), Gly (G), Gln (O), Asn (N), or D-Pro (p);
$X_2$ is an aliphatic residue;
$X_3$ is Leu (L);
$X_4$ is an acidic residue;
$X_5$ is Leu (L) or Phe (F);
$X_6$ is Leu (L) or Phe (F);
$X_7$ is a basic residue;
$X_8$ is an acidic residue;
$X_9$ is Leu (L) or Trp (W);
$X_{10}$ is Leu (L) or Trp (W);
$X_{11}$ is an acidic residue or Asn (N);
$X_{12}$ is an acidic residue;
$X_{13}$ is Gly (G), Trp (W) or Phe (F);
$X_{14}$ is a basic residue or Leu (L);
$X_{15}$ is Gln (O) or Asn (N);
$X_{16}$ is a basic residue;
$X_{17}$ is Leu (L);
$X_{18}$ is a basic residue;

wherein at least one L-enantiomeric residue of formula (II) other than Pro (P) at $X_1$ is replaced with an identical D-enantiomeric residue $Z_1$ is $H_2N$— or RC(O)NR—;
$Z_2$ is —C(O)NRR, —C(O)OR or —C(O)OH, or a salt thereof;

each R is independently —H, $(C_1-C_6)$ alkyl, $(C_1-C_6)$ alkenyl, $(C_1-C_6)$ alkynyl, $(C_5-C_{20})$ aryl, $(C_6-C_{26})$ alkaryl, 5-20 membered heteroaryl, 6-26 membered alkheteroaryl or a 1 to 4-residue peptide or peptide analogue in which one or more bonds between residues 1-4 are independently a substituted amide, an isotere of an amide or an amide mimetic; and each "—" between residues $X_1$ through $X_{18}$ independently designates an amide linkage, a substituted amide linkage, an isotere of an amide or an amide mimetic; or (ii) a 14 to 21-residue deleted peptide or peptide analogue according to formula (II) in which at least one and up to eight of residues $X_1, X_2, X_3, X_4, X_5, X_6, X_7, X_8, X_9, X_{10}, X_{11}, X_{12}, X_{13}, X_{14}, X_{15}, X_{16}, X_{17}$, or $X_{18}$ are optionally deleted and wherein at least one remaining L-enantiomeric residue of formula (II) is replaced with an identical D-enantiomeric residue; or (iii) an 18 to 22-residue altered peptide or peptide analogue according to formula (II) in which at least one and up to eight of residues $X_1, X_2, X_3, X_4, X_5, X_6, X_7, X_8, X_9, X_{10}, X_{11}, X_{12}, X_{13}, X_{14}, X_{15}, X_{16}, X_{17}$, or $X_{18}$ is conservatively substituted and wherein at least one L-enantiomeric residue of the resulting altered peptide or peptide analogue is replaced with an identical D-enantiomeric residue; or (iv) an N-terminally blocked form, a C-terminally blocked form, or an N- and C-terminally blocked form of formula (II).

* * * * *

SEQUENCE LISTING

<160> NUMBER OF SEQ ID NOS: 258

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Naphthylalanine

<400> SEQUENCE: 1

Pro Val Leu Asp Leu Phe Arg Glu Leu Leu Asn Glu Leu Leu Glu Xaa
1               5                   10                  15

Leu Lys Gln Lys Leu Lys
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Val Leu Asp Leu Phe Arg Glu Leu Leu Asn Glu Leu Leu Glu Trp
1               5                   10                  15

Leu Lys Gln Lys Leu Lys
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 5
<211> LENGTH: 23

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro

<400> SEQUENCE: 5

Pro Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 6

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 9
<211> LENGTH: 22
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 9

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Naphthylalanine

<400> SEQUENCE: 10

Pro Val Leu Asp Leu Phe Arg Glu Leu Leu Asn Glu Leu Leu Glu Ala
1               5                   10                  15

Xaa Lys Gln Lys Leu Lys
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Val Leu Asp Leu Phe Lys Glu Leu Leu Gln Glu Leu Leu Glu Ala
1               5                   10                  15

Leu Lys Gln Lys Leu Lys
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Val Leu Asp Leu Phe Arg Glu Leu Leu Asn Glu Leu Leu Glu Ala
1               5                   10                  15

Gly Lys Gln Lys Leu Lys
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Val Leu Asp Leu Phe Arg Glu Leu Leu Asn Glu Gly Leu Glu Ala
1               5                   10                  15

Leu Lys Gln Lys Leu Lys
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Ornithine
<220> FEATURE:
<221> NAME/KEY: MOD_RES
<222> LOCATION: (20)..(20)
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 14

Pro Val Leu Asp Leu Phe Arg Glu Leu Leu Asn Glu Leu Leu Glu Ala
1               5                   10                  15

Leu Xaa Gln Xaa Leu Xaa
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Val Leu Asp Leu Phe Arg Glu Leu Trp Asn Glu Leu Leu Glu Ala
1               5                   10                  15

Leu Lys Gln Lys Leu Lys
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Val Leu Glu Leu Phe Lys Glu Leu Leu Gln Glu Leu Leu Glu Ala

```
                1               5                  10                 15

Leu Lys Gln Lys Leu Lys
            20

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Val Leu Asp Leu Phe Arg Glu Leu Leu Asn Glu Leu Leu Glu Ala
1               5                   10                  15

Leu Lys Gln Lys Leu Lys
            20

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro

<400> SEQUENCE: 19

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro

<400> SEQUENCE: 21

Pro Val Leu Asp Leu Phe Arg Glu Leu Leu Asn Glu Leu Leu Glu Ala
1               5                   10                  15

Leu Lys Gln Lys Leu Lys
```

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 25

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 26
<211> LENGTH: 22
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 26

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Naphthylalanine

<400> SEQUENCE: 27

Pro Val Leu Asp Leu Phe Arg Glu Leu Leu Asn Glu Leu Xaa Glu Ala
1               5                   10                  15

Leu Lys Gln Lys Leu Lys
            20

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Val Leu Asp Leu Phe Arg Glu Leu Leu Asn Glu Leu Trp Glu Ala
1               5                   10                  15

Leu Lys Gln Lys Leu Lys
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Val Leu Asp Leu Phe Arg Glu Leu Leu Asn Glu Leu Leu Glu Ala
1               5                   10                  15

Leu Lys Gln Lys Leu Lys
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Val Leu Asp Leu Phe Arg Glu Leu Leu Asn Glu Leu Leu Glu Ala
```

```
1               5                   10                  15
```

Leu Lys Gln Lys Leu Lys
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 31

Pro Val Leu Asp Leu Phe Leu Glu Leu Leu Asn Glu Xaa Leu Glu Ala
1               5                   10                  15

Leu Lys Gln Lys Leu Lys
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-aminoisobutyric acid

<400> SEQUENCE: 32

Xaa Val Leu Asp Leu Phe Arg Glu Leu Leu Asn Glu Leu Leu Glu Ala
1               5                   10                  15

Leu Lys Gln Lys Leu Lys
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Val Leu Asp Leu Phe Arg Glu Lys Leu Asn Glu Leu Leu Glu Ala
1               5                   10                  15

Leu Lys Gln Lys Leu Lys
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Naphthylalanine

<400> SEQUENCE: 34

```
Pro Val Leu Asp Xaa Phe Arg Glu Leu Leu Asn Glu Leu Leu Glu Ala
1               5                   10                  15

Leu Lys Gln Lys Leu Lys
            20

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Val Leu Asp Trp Phe Arg Glu Leu Leu Asn Glu Leu Leu Glu Ala
1               5                   10                  15

Leu Lys Gln Lys Leu Lys
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Leu Leu Glu Leu Leu Lys Glu Leu Leu Gln Glu Leu Leu Glu Ala
1               5                   10                  15

Leu Lys Gln Lys Leu Lys
            20

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Val Leu Asp Leu Phe Arg Glu Trp Leu Asn Glu Leu Leu Glu Ala
1               5                   10                  15

Leu Lys Gln Lys Leu Lys
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 38

Pro Val Leu Asp Leu Phe Arg Glu Leu Leu Asn Glu Xaa Leu Glu Ala
1               5                   10                  15

Trp Lys Gln Lys Leu Lys
            20
```

```
<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Val Leu Asp Leu Phe Arg Glu Leu Leu Glu Glu Leu Leu Lys Ala
1               5                   10                  15

Leu Lys Lys Lys Leu Lys
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Val Leu Asp Leu Phe Asn Glu Leu Leu Arg Glu Leu Leu Glu Ala
1               5                   10                  15

Leu Gln Lys Lys Leu Lys
            20

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 41

Pro Val Leu Asp Leu Trp Arg Glu Leu Leu Asn Glu Xaa Leu Glu Ala
1               5                   10                  15

Leu Lys Gln Lys Leu Lys
            20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 42

Pro Val Leu Asp Glu Phe Arg Glu Lys Leu Asn Glu Xaa Trp Glu Ala
1               5                   10                  15

Leu Lys Gln Lys Leu Lys
            20

<210> SEQ ID NO 43
<211> LENGTH: 22
<212> TYPE: PRT
```

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 43

Pro Val Leu Asp Glu Phe Arg Glu Lys Leu Trp Glu Xaa Leu Glu Ala
1               5                   10                  15

Leu Lys Gln Lys Leu Lys
            20

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: D-Asp
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: D-Lys
<220> FEATURE:
<221> NAME/KEY: MOD_RES
<222> LOCATION: (10)..(10)
<223> OTHER INFORMATION: D-Leu
<220> FEATURE:
<221> NAME/KEY: MOD_RES
<222> LOCATION: (11)..(11)
<223> OTHER INFORMATION: D-Asn
<220> FEATURE:
<221> NAME/KEY: MOD_RES
<222> LOCATION: (12)..(12)
<223> OTHER INFORMATION: D-Glu
<220> FEATURE:
<221> NAME/KEY: MOD_RES
<222> LOCATION: (13)..(13)
<223> OTHER INFORMATION: Alpha-aminoisobutyric acid
<220> FEATURE:
<221> NAME/KEY: MOD_RES

```
<222> LOCATION: (14)..(14)
<223> OTHER INFORMATION: D-Leu
<220> FEATURE:
<221> NAME/KEY: MOD_RES
<222> LOCATION: (15)..(15)
<223> OTHER INFORMATION: D-Glu
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Leu
<220> FEATURE:
<221> NAME/KEY: MOD_RES
<222> LOCATION: (18)..(18)
<223> OTHER INFORMATION: D-Lys
<220> FEATURE:
<221> NAME/KEY: MOD_RES
<222> LOCATION: (19)..(19)
<223> OTHER INFORMATION: D-Gln
<220> FEATURE:
<221> NAME/KEY: MOD_RES
<222> LOCATION: (20)..(20)
<223> OTHER INFORMATION: D-Lys
<220> FEATURE:
<221> NAME/KEY: MOD_RES
<222> LOCATION: (21)..(21)
<223> OTHER INFORMATION: D-Leu
<220> FEATURE:
<221> NAME/KEY: MOD_RES
<222> LOCATION: (22)..(22)
<223> OTHER INFORMATION: D-Lys

<400> SEQUENCE: 44

Pro Val Leu Asp Glu Phe Arg Glu Lys Leu Asn Glu Xaa Leu Glu Ala
1               5                   10                  15

Leu Lys Gln Lys Leu Lys
            20

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 45

Pro Val Leu Asp Glu Phe Arg Glu Lys Leu Asn Glu Xaa Leu Glu Ala
1               5                   10                  15

Leu Lys Gln Lys Leu Lys
            20

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 46
```

```
Pro Val Leu Asp Leu Phe Arg Glu Lys Leu Asn Glu Xaa Leu Glu Ala
1               5                   10                  15

Leu Lys Gln Lys Leu Lys
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Leu Asp Leu Phe Arg Glu Leu Leu Asn Glu Gly Leu Glu Ala Leu
1               5                   10                  15

Lys Gln Lys Leu Lys
            20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Val

<400> SEQUENCE: 48

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Val Leu Asp Leu Phe Arg Asn Leu Leu Glu Lys Leu Leu Glu Ala
1               5                   10                  15

Leu Glu Gln Lys Leu Lys
            20

<210> SEQ ID NO 50
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 50
```

```
Pro Val Leu Asp Leu Phe Arg Glu Leu Leu Trp Glu Xaa Leu Glu Ala
1               5                   10                  15

Leu Lys Gln Lys Leu Lys
            20
```

<210> SEQ ID NO 51
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 51

```
Pro Val Leu Asp Leu Phe Trp Glu Leu Leu Asn Glu Xaa Leu Glu Ala
1               5                   10                  15

Leu Lys Gln Lys Leu Lys
            20
```

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 52

```
Pro Val Trp Asp Glu Phe Arg Glu Lys Leu Asn Glu Xaa Leu Glu Ala
1               5                   10                  15

Leu Lys Gln Lys Leu Lys
            20
```

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Val Val Leu Asp Leu Phe Arg Glu Leu Leu Asn Glu Leu Leu Glu Ala
1               5                   10                  15

Leu Lys Gln Lys Leu Lys
            20
```

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Pro Val Leu Asp Leu Phe Arg Glu Leu Leu Asn Glu Trp Leu Glu Ala
1               5                   10                  15
```

```
Leu Lys Gln Lys Leu Lys
            20

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Leu Phe Arg Glu Leu Leu Asn Glu Leu Leu Glu Ala Leu Lys Gln
1               5                   10                  15

Lys Leu Lys

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Val Leu Asp Leu Phe Arg Glu Leu Leu Asn Glu Leu Leu Glu Ala
1               5                   10                  15

Leu Lys Gln Lys Lys Lys
            20

<210> SEQ ID NO 57
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Val Leu Asp Leu Phe Arg Asn Leu Leu Glu Glu Leu Leu Lys Ala
1               5                   10                  15

Leu Glu Gln Lys Leu Lys
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 58

Pro Val Leu Asp Glu Phe Arg Glu Lys Leu Asn Glu Xaa Leu Glu Ala
1               5                   10                  15

Leu Lys Gln Lys Leu
            20

<210> SEQ ID NO 59
<211> LENGTH: 22
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 59

Leu Val Leu Asp Leu Phe Arg Glu Leu Leu Asn Glu Leu Leu Glu Ala
1               5                   10                  15

Leu Lys Gln Lys Leu Lys
            20

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Val Leu Asp Leu Phe Arg Glu Leu Leu Asn Glu Leu Leu Glu Ala
1               5                   10                  15

Leu Lys Gln

<210> SEQ ID NO 61
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 61

Pro Val Leu Asp Glu Phe Arg Trp Lys Leu Asn Glu Xaa Leu Glu Ala
1               5                   10                  15

Leu Lys Gln Lys Leu Lys
            20

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 62

Pro Val Leu Asp Glu Trp Arg Glu Lys Leu Asn Glu Xaa Leu Glu Ala
1               5                   10                  15

Leu Lys Gln Lys Leu Lys
            20

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide -continued

```
<220> FEATURE:
<221> NAME/KEY: MOD_RES
<222> LOCATION: (13)..(13)
<223> OTHER INFORMATION: Alpha-aminoisobutyric acid

<400> SEQUENCE: 63

Pro Val Leu Asp Phe Phe Arg Glu Lys Leu Asn Glu Xaa Leu Glu Ala
1               5                   10                  15
Leu Lys Gln Lys Leu Lys
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 64

Pro Trp Leu Asp Glu Phe Arg Glu Lys Leu Asn Glu Xaa Leu Glu Ala
1               5                   10                  15
Leu Lys Gln Lys Leu Lys
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Alpha-aminoisobutyric acid

<400> SEQUENCE: 65

Val Leu Asp Glu Phe Arg Glu Lys Leu Asn Glu Xaa Leu Glu Ala Leu
1               5                   10                  15
Lys Gln Lys Leu Lys
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Val Leu Asp Leu Phe Arg Asn Leu Leu Glu Glu Leu Leu Glu Ala
1               5                   10                  15
Leu Gln Lys Lys Leu Lys
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
                            -continued
        peptide

<400> SEQUENCE: 67

Val Leu Asp Leu Phe Arg Glu Leu Leu Asn Glu Leu Leu Glu Ala Leu
1               5                   10                  15

Lys Gln Lys Leu Lys
            20

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 68

Pro Val Leu Asp Glu Phe Arg Glu Leu Leu Lys Glu Xaa Leu Glu Ala
1               5                   10                  15

Leu Lys Gln Lys Leu Lys
            20

<210> SEQ ID NO 69
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 69

Pro Val Leu Asp Glu Phe Arg Lys Lys Leu Asn Glu Xaa Leu Glu Ala
1               5                   10                  15

Leu Lys Gln Lys Leu Lys
            20

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 70

Pro Val Leu Asp Glu Phe Arg Glu Leu Leu Tyr Glu Xaa Leu Glu Ala
1               5                   10                  15

Leu Lys Gln Lys Leu Lys
            20

<210> SEQ ID NO 71
<211> LENGTH: 22
<212> TYPE: PRT
<213> ORGANISM: Artificial Sequence
<220> FEATURE:
```

<223> OTHER INFORMATION: Description of Artificial Sequence: Synthetic
       peptide
<220> FEATURE:
<221> NAME/KEY: MOD_RES
<222> LOCATION: (14)..(14)
<223> OTHER INFORMATION: Alpha-aminoisobutyric acid

<400> SEQUENCE: 71

Pro Val Leu Asp Glu Phe Arg Glu Lys Leu Asn Glu Leu Xaa Glu Ala
1               5                   10                  15

Leu Lys Gln Lys Leu Lys
            20

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 72

Pro Val Leu Asp Leu Phe Arg Glu Leu Leu Asn Glu Xaa Leu Trp Ala
1               5                   10                  15

Leu Lys Gln Lys Leu Lys
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 73

Pro Val Leu Asp Glu Phe Trp Glu Lys Leu Asn Glu Xaa Leu Glu Ala
1               5                   10                  15

Leu Lys Gln Lys Leu Lys
            20

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 74

Pro Val Leu Asp Lys Phe Arg Glu Lys Leu Asn Glu Xaa Leu Glu Ala
1               5                   10                  15

Leu Lys Gln Lys Leu Lys
            20

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 76

Pro Val Leu Asp Glu Phe Arg Glu Leu Leu Phe Glu Xaa Leu Glu Ala
1               5                   10                  15

Leu Lys Gln Lys Leu Lys
            20

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 77

Pro Val Leu Asp Glu Phe Arg Glu Lys Leu Asn Lys Xaa Leu Glu Ala
1               5                   10                  15

Leu Lys Gln Lys Leu Lys
            20

<210> SEQ ID NO 78
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 78

Pro Val Leu Asp Glu Phe Arg Asp Lys Leu Asn Glu Xaa Leu Glu Ala
1               5                   10                  15

Leu Lys Gln Lys Leu Lys
            20

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Val Leu Asp Glu Phe Arg Glu Leu Leu Asn Glu Leu Leu Glu Ala
1               5                   10                  15

Leu Lys Gln Lys Leu Lys
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Pro Val Leu Asp Leu Phe Glu Arg Leu Leu Asn Glu Leu Leu Glu Ala
1               5                   10                  15

Leu Gln Lys Lys Leu Lys
            20

<210> SEQ ID NO 81
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 81

Pro Val Leu Asp Glu Phe Arg Glu Lys Leu Asn Trp Xaa Leu Glu Ala
1               5                   10                  15

Leu Lys Gln Lys Leu Lys
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Alpha-aminoisobutyric acid

<400> SEQUENCE: 82

Leu Asp Glu Phe Arg Glu Lys Leu Asn Glu Xaa Leu Glu Ala Leu Lys
1               5                   10                  15

Gln Lys Leu Lys
            20

<210> SEQ ID NO 83
<211> LENGTH: 22

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 83

Pro Val Leu Asp Glu Phe Arg Glu Lys Leu Asn Glu Xaa Leu Glu Ala
1               5                   10                  15

Leu Trp Gln Lys Leu Lys
            20

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Val Leu Asp Glu Phe Arg Glu Lys Leu Asn Glu Leu Leu Glu Ala
1               5                   10                  15

Leu Lys Gln Lys Leu Lys
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Leu Asp Leu Phe Arg Glu Leu Leu Asn Glu Leu Leu Glu Ala Leu
1               5                   10                  15

Lys Gln Lys Leu Lys
            20

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Pro Val Leu Glu Leu Phe Glu Arg Leu Leu Asp Glu Leu Leu Asn Ala
1               5                   10                  15

Leu Gln Lys Lys Leu Lys
            20

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: D-Pro
<220> FEATURE:
<221> NAME/KEY: MOD_RES
<222> LOCATION: (2)..(3)
<223> OTHER INFORMATION: D-Leu
<220> FEATURE:
<221> NAME/KEY: MOD_RES
<222> LOCATION: (4)..(4)
<223> OTHER INFORMATION: D-Glu
<220> FEATURE:
<221> NAME/KEY: MOD_RES
<222> LOCATION: (5)..(6)
<223> OTHER INFORMATION: D-Leu
<220> FEATURE:
<221> NAME/KEY: MOD_RES
<222> LOCATION: (7)..(7)
<223> OTHER INFORMATION: D-Lys
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(10)
<223> OTHER INFORMATION: D-Leu
<220> FEATURE:
<221> NAME/KEY: MOD_RES
<222> LOCATION: (11)..(11)
<223> OTHER INFORMATION: D-Gln
<220> FEATURE:
<221> NAME/KEY: MOD_RES
<222> LOCATION: (12)..(12)
<223> OTHER INFORMATION: D-Glu
<220> FEATURE:
<221> NAME/KEY: MOD_RES
<222> LOCATION: (13)..(14)
<223> OTHER INFORMATION: D-Leu
<220> FEATURE:
<221> NAME/KEY: MOD_RES
<222> LOCATION: (15)..(15)
<223> OTHER INFORMATION: D-Glu
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Leu
<220> FEATURE:
<221> NAME/KEY: MOD_RES
<222> LOCATION: (18)..(18)
<223> OTHER INFORMATION: D-Lys
<220> FEATURE:
<221> NAME/KEY: MOD_RES
<222> LOCATION: (19)..(19)
<223> OTHER INFORMATION: D-Gln
<220> FEATURE:
<221> NAME/KEY: MOD_RES
<222> LOCATION: (20)..(20)
<223> OTHER INFORMATION: D-Lys
<220> FEATURE:
<221> NAME/KEY: MOD_RES
<222> LOCATION: (21)..(21)
<223> OTHER INFORMATION: D-Leu
<220> FEATURE:
<221> NAME/KEY: MOD_RES
<222> LOCATION: (22)..(22)
<223> OTHER INFORMATION: D-Lys

<400> SEQUENCE: 87

Pro Leu Leu Glu Leu Leu Lys Glu Leu Leu Gln Glu Leu Leu Glu Ala
1               5                   10                  15

Leu Lys Gln Lys Leu Lys
            20
```

-continued

<210> SEQ ID NO 88
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 88

Pro Val Leu Asp Lys Phe Arg Glu Leu Leu Asn Glu Xaa Leu Glu Ala
1               5                   10                  15

Leu Lys Gln Lys Leu Lys
            20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 89

Pro Val Leu Asp Glu Phe Arg Glu Lys Leu Asn Glu Xaa Leu Trp Ala
1               5                   10                  15

Leu Lys Gln Lys Leu Lys
            20

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Alpha-aminoisobutyric acid

<400> SEQUENCE: 90

Asp Glu Phe Arg Glu Lys Leu Asn Glu Xaa Leu Glu Ala Leu Lys Gln
1               5                   10                  15

Lys Leu Lys

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 91

Pro Val Leu Asp Glu Phe Arg Glu Leu Leu Asn Glu Xaa Leu Glu Ala
1               5                   10                  15

```
Leu Lys Gln Lys Leu Lys
            20

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 92

Pro Val Leu Asp Glu Phe Arg Glu Leu Tyr Asn Glu Xaa Leu Glu Ala
1               5                   10                  15

Leu Lys Gln Lys Leu Lys
            20

<210> SEQ ID NO 93
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 93

Pro Val Leu Asp Glu Phe Arg Glu Lys Leu Asn Glu Xaa Leu Lys Ala
1               5                   10                  15

Leu Lys Gln Lys Leu Lys
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Val Leu Asp Glu Phe Arg Glu Lys Leu Asn Glu Ala Leu Glu Ala
1               5                   10                  15

Leu Lys Gln Lys Leu Lys
            20

<210> SEQ ID NO 95
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 95

Pro Val Leu Asp Leu Phe Arg Glu Leu Leu Asn Leu Xaa Leu Glu Ala
```

-continued

```
1               5                  10                 15
Leu Lys Gln Lys Leu Lys
            20

<210> SEQ ID NO 96
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: D-Asp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(10)
<223> OTHER INFORMATION: D-Leu
<220> FEATURE:
<221> NAME/KEY: MOD_RES
<222> LOCATION: (11)..(11)
<223> OTHER INFORMATION: D-Asn
<220> FEATURE:
<221> NAME/KEY: MOD_RES
<222> LOCATION: (12)..(12)
<223> OTHER INFORMATION: D-Glu
<220> FEATURE:
<221> NAME/KEY: MOD_RES
<222> LOCATION: (13)..(13)
<223> OTHER INFORMATION: Alpha-aminoisobutyric acid
<220> FEATURE:
<221> NAME/KEY: MOD_RES
<222> LOCATION: (14)..(14)
<223> OTHER INFORMATION: D-Leu
<220> FEATURE:
<221> NAME/KEY: MOD_RES
<222> LOCATION: (15)..(15)
<223> OTHER INFORMATION: D-Glu
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Leu
<220> FEATURE:
<221> NAME/KEY: MOD_RES
```

```
<222> LOCATION: (18)..(18)
<223> OTHER INFORMATION: D-Lys
<220> FEATURE:
<221> NAME/KEY: MOD_RES
<222> LOCATION: (19)..(19)
<223> OTHER INFORMATION: D-Gln
<220> FEATURE:
<221> NAME/KEY: MOD_RES
<222> LOCATION: (20)..(20)
<223> OTHER INFORMATION: D-Lys
<220> FEATURE:
<221> NAME/KEY: MOD_RES
<222> LOCATION: (21)..(21)
<223> OTHER INFORMATION: D-Leu
<220> FEATURE:
<221> NAME/KEY: MOD_RES
<222> LOCATION: (22)..(22)
<223> OTHER INFORMATION: D-Lys

<400> SEQUENCE: 96

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Val Leu Asp Leu Phe Arg Glu Leu Leu Asn Glu Leu Leu Glu
1               5                   10                  15

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Pro Val Leu Asp Leu Phe Arg Glu Leu Leu Asn Glu Glu Leu Glu Ala
1               5                   10                  15

Leu Lys Gln Lys Leu Lys
            20

<210> SEQ ID NO 99
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 100
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: D-Asp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(10)
<223> OTHER INFORMATION: D-Leu
<220> FEATURE:
<221> NAME/KEY: MOD_RES
<222> LOCATION: (11)..(11)
<223> OTHER INFORMATION: D-Asn
<220> FEATURE:
<221> NAME/KEY: MOD_RES
<222> LOCATION: (12)..(12)
<223> OTHER INFORMATION: D-Glu
<220> FEATURE:
<221> NAME/KEY: MOD_RES
<222> LOCATION: (13)..(14)
<223> OTHER INFORMATION: D-Leu
<220> FEATURE:
<221> NAME/KEY: MOD_RES
<222> LOCATION: (15)..(15)
<223> OTHER INFORMATION: D-Glu
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Leu
<220> FEATURE:
<221> NAME/KEY: MOD_RES
<222> LOCATION: (18)..(18)
<223> OTHER INFORMATION: D-Lys
<220> FEATURE:
<221> NAME/KEY: MOD_RES
<222> LOCATION: (19)..(19)
<223> OTHER INFORMATION: D-Gln
<220> FEATURE:
<221> NAME/KEY: MOD_RES
<222> LOCATION: (20)..(20)
<223> OTHER INFORMATION: D-Lys
<220> FEATURE:
<221> NAME/KEY: MOD_RES
<222> LOCATION: (21)..(21)
```

```
<223> OTHER INFORMATION: D-Leu
<220> FEATURE:
<221> NAME/KEY: MOD_RES
<222> LOCATION: (22)..(22)
<223> OTHER INFORMATION: D-Lys

<400> SEQUENCE: 100

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 101

Pro Val Leu Asp Leu Phe Arg Glu Leu Leu Asn Trp Xaa Leu Glu Ala
1               5                   10                  15

Leu Lys Gln Lys Leu Lys
            20

<210> SEQ ID NO 102
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 102

Pro Val Leu Asp Leu Phe Arg Glu Leu Leu Asn Leu Xaa Leu Glu Ala
1               5                   10                  15

Leu Lys Glu Lys Leu Lys
            20

<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Val Leu Asp Glu Phe Arg Glu Leu Leu Asn Glu Glu Leu Glu Ala
1               5                   10                  15

Leu Lys Gln Lys Leu Lys
            20

<210> SEQ ID NO 104
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 104

Pro Leu Leu Asn Glu Leu Leu Glu Ala Leu Lys Gln Lys Leu Lys
1               5                   10                  15

<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Ala Ala Asp Ala Phe Arg Glu Ala Ala Asn Glu Ala Ala Glu Ala
1               5                   10                  15

Ala Lys Gln Lys Ala Lys
            20

<210> SEQ ID NO 106
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Val Leu Asp Leu Phe Arg Glu Lys Leu Asn Glu Glu Leu Glu Ala
1               5                   10                  15

Leu Lys Gln Lys Leu Lys
            20

<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala
<220> FEATURE:
```

```
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(10)
<223> OTHER INFORMATION: D-Leu
<220> FEATURE:
<221> NAME/KEY: MOD_RES
<222> LOCATION: (11)..(11)
<223> OTHER INFORMATION: D-Glu
<220> FEATURE:
<221> NAME/KEY: MOD_RES
<222> LOCATION: (12)..(12)
<223> OTHER INFORMATION: D-Asn
<220> FEATURE:
<221> NAME/KEY: MOD_RES
<222> LOCATION: (13)..(14)
<223> OTHER INFORMATION: D-Leu
<220> FEATURE:
<221> NAME/KEY: MOD_RES
<222> LOCATION: (15)..(15)
<223> OTHER INFORMATION: D-Glu
<220> FEATURE:
<221> NAME/KEY: MOD_RES
<222> LOCATION: (16)..(16)
<223> OTHER INFORMATION: D-Arg
<220> FEATURE:
<221> NAME/KEY: MOD_RES
<222> LOCATION: (17)..(17)
<223> OTHER INFORMATION: D-Phe
<220> FEATURE:
<221> NAME/KEY: MOD_RES
<222> LOCATION: (18)..(18)
<223> OTHER INFORMATION: D-Leu
<220> FEATURE:
<221> NAME/KEY: MOD_RES
<222> LOCATION: (19)..(19)
<223> OTHER INFORMATION: D-Asp
<220> FEATURE:
<221> NAME/KEY: MOD_RES
<222> LOCATION: (20)..(20)
<223> OTHER INFORMATION: D-Leu
<220> FEATURE:
<221> NAME/KEY: MOD_RES
<222> LOCATION: (21)..(21)
<223> OTHER INFORMATION: D-Val
<220> FEATURE:
<221> NAME/KEY: MOD_RES
<222> LOCATION: (22)..(22)
<223> OTHER INFORMATION: D-Pro

<400> SEQUENCE: 107

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 108
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 108

Pro Val Leu Asp Leu Phe Arg Trp Leu Leu Asn Glu Xaa Leu Glu Ala
1               5                   10                  15

Leu Lys Gln Lys Leu Lys
```

<210> SEQ ID NO 109
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Val Leu Asp Glu Phe Arg Glu Lys Leu Asn Glu Arg Leu Glu Ala
1               5                   10                  15

Leu Lys Gln Lys Leu Lys
            20

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(14)
<223> OTHER INFORMATION: Alpha-aminoisobutyric acid

<400> SEQUENCE: 110

Pro Val Leu Asp Glu Phe Arg Glu Lys Leu Asn Glu Xaa Xaa Glu Ala
1               5                   10                  15

Leu Lys Gln Lys Leu Lys
            20

<210> SEQ ID NO 111
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 111

Pro Val Leu Asp Glu Phe Arg Glu Lys Leu Trp Glu Xaa Trp Glu Ala
1               5                   10                  15

Leu Lys Gln Lys Leu Lys
            20

<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 112

Pro Val Leu Asp Glu Phe Arg Glu Lys Leu Asn Glu Xaa Ser Glu Ala
1               5                   10                  15

```
Leu Lys Gln Lys Leu Lys
            20

<210> SEQ ID NO 113
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Val Leu Asp Glu Phe Arg Glu Lys Leu Asn Glu Pro Leu Glu Ala
1               5                   10                  15

Leu Lys Gln Lys Leu Lys
            20

<210> SEQ ID NO 114
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 114

Pro Val Leu Asp Glu Phe Arg Glu Lys Leu Asn Glu Xaa Met Glu Ala
1               5                   10                  15

Leu Lys Gln Lys Leu Lys
            20

<210> SEQ ID NO 115
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 115

Pro Lys Leu Asp Glu Phe Arg Glu Lys Leu Asn Glu Xaa Leu Glu Ala
1               5                   10                  15

Leu Lys Gln Lys Leu Lys
            20

<210> SEQ ID NO 116
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 116

Pro His Leu Asp Glu Phe Arg Glu Lys Leu Asn Glu Xaa Leu Glu Ala
1               5                   10                  15
```

```
Leu Lys Gln Lys Leu Lys
            20

<210> SEQ ID NO 117
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 117

Pro Glu Leu Asp Glu Phe Arg Glu Lys Leu Asn Glu Xaa Leu Glu Ala
1               5                   10                  15

Leu Lys Gln Lys Leu Lys
            20

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Alpha-aminoisobutyric acid

<400> SEQUENCE: 118

Pro Val Leu Asp Glu Phe Arg Glu Lys Leu Asn Glu Xaa Leu Glu Ala
1               5                   10                  15

Leu Glu Gln Lys Leu Lys
            20

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Alpha-aminoisobutyric acid

<400> SEQUENCE: 119

Pro Val Leu Asp Glu Phe Arg Glu Lys Leu Asn Glu Glu Leu Glu Ala
1               5                   10                  15

Xaa Lys Gln Lys Leu Lys
            20

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Alpha-aminoisobutyric acid
```

```
<400> SEQUENCE: 120

Pro Val Leu Asp Glu Phe Arg Glu Lys Leu Asn Glu Glu Leu Glu Xaa
1               5                   10                  15

Leu Lys Gln Lys Leu Lys
            20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Val Leu Asp Glu Phe Arg Glu Lys Leu Asn Glu Glu Leu Glu Ala
1               5                   10                  15

Leu Trp Gln Lys Leu Lys
            20

<210> SEQ ID NO 122
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro Val Leu Asp Glu Phe Arg Glu Lys Leu Asn Glu Glu Leu Glu Trp
1               5                   10                  15

Leu Lys Gln Lys Leu Lys
            20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Val Leu Asp Leu Phe Arg Glu Leu Leu Asn Glu Leu Leu Glu Ala
1               5                   10                  15

Leu Lys Gln Lys Leu Lys
            20

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ornithine
<220> FEATURE:
<221> NAME/KEY: MOD_RES
<222> LOCATION: (18)..(18)
<223> OTHER INFORMATION: Ornithine
<220> FEATURE:
<221> NAME/KEY: MOD_RES
<222> LOCATION: (20)..(20)
```

```
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 124

Pro Val Leu Asp Leu Phe Xaa Glu Leu Leu Asn Glu Leu Leu Glu Ala
1               5                   10                  15

Leu Xaa Gln Xaa Leu Xaa
            20

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Val Leu Asp Leu Phe Arg Glu Leu Leu Asn Glu Leu Leu Glu Ala
1               5                   10                  15

Leu Lys Gln Lys Leu Lys
            20

<210> SEQ ID NO 126
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Val Leu Asp Leu Phe Arg Glu Leu Leu Asn Glu Leu Gly Glu Ala
1               5                   10                  15

Leu Lys Gln Lys Leu Lys
            20

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 128
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Val Leu Asp Leu Phe Arg Glu Leu Leu Asn Glu Leu Leu Glu Phe
1               5                   10                  15
```

```
Leu Lys Gln Lys Leu Lys
            20

<210> SEQ ID NO 129
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Val Leu Glu Leu Phe Asn Asp Leu Leu Arg Glu Leu Leu Glu Ala
1               5                   10                  15

Leu Gln Lys Lys Leu Lys
            20

<210> SEQ ID NO 130
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Pro Val Leu Glu Leu Phe Asn Asp Leu Leu Arg Glu Leu Leu Glu Ala
1               5                   10                  15

Leu Lys Gln Lys Leu Lys
            20

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro Val Leu Glu Leu Phe Lys Glu Leu Leu Asn Glu Leu Leu Asp Ala
1               5                   10                  15

Leu Arg Gln Lys Leu Lys
            20

<210> SEQ ID NO 132
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Val Leu Asp Leu Phe Arg Glu Leu Leu Glu Asn Leu Leu Glu Ala
1               5                   10                  15

Leu Gln Lys Lys Leu Lys
            20

<210> SEQ ID NO 133
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 133

Pro Val Leu Glu Leu Phe Glu Arg Leu Leu Glu Asp Leu Leu Gln Ala
1               5                   10                  15

Leu Asn Lys Lys Leu Lys
            20

<210> SEQ ID NO 134
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Pro Val Leu Glu Leu Phe Glu Arg Leu Leu Glu Asp Leu Leu Lys Ala
1               5                   10                  15

Leu Asn Gln Lys Leu Lys
            20

<210> SEQ ID NO 135
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Val Leu Asp Leu Phe Arg Glu Leu Leu Asn Glu Leu Leu Glu Ala
1               5                   10                  15

Leu Lys Gln Lys Leu Lys
            20

<210> SEQ ID NO 136
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Ala Leu Glu Leu Phe Lys Asp Leu Leu Gln Glu Leu Leu Glu Ala
1               5                   10                  15

Leu Lys Gln Lys Leu Lys
            20

<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Naphthylalanine

<400> SEQUENCE: 137

Pro Val Leu Asp Leu Phe Arg Glu Leu Leu Asn Glu Gly Leu Glu Ala
1               5                   10                  15

Xaa Lys Gln Lys Leu Lys
```

<210> SEQ ID NO 138
<211> LENGTH: 22
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 138

Pro Val Leu Asp Leu Phe Arg Glu Leu Leu Asn Glu Gly Leu Glu Trp
1               5                   10                  15

Leu Lys Gln Lys Leu Lys
            20

<210> SEQ ID NO 139
<211> LENGTH: 22
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 139

Pro Val Leu Asp Leu Phe Arg Glu Leu Trp Asn Glu Gly Leu Glu Ala
1               5                   10                  15

Leu Lys Gln Lys Leu Lys
            20

<210> SEQ ID NO 140
<211> LENGTH: 22
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (18)..(18)
<223> OTHER INFORMATION: Ornithine
<220> FEATURE:
<221> NAME/KEY: MOD_RES
<222> LOCATION: (20)..(20)
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 140

Pro Val Leu Asp Leu Phe Arg Glu Leu Leu Asn Glu Gly Leu Glu Ala
1               5                   10                  15

Leu Xaa Gln Xaa Leu Xaa
            20

<210> SEQ ID NO 141
<211> LENGTH: 22
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 141

Pro Val Leu Asp Phe Phe Arg Glu Leu Leu Asn Glu Gly Leu Glu Ala
1               5                   10                  15

```
<210> SEQ ID NO 142
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Pro Val Leu Glu Leu Phe Arg Glu Leu Leu Asn Glu Gly Leu Glu Ala
1               5                   10                  15

Leu Lys Gln Lys Leu Lys
            20

<210> SEQ ID NO 143
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 144
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro

<400> SEQUENCE: 144

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 145
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Val Leu Glu Leu Phe Glu Asn Leu Leu Glu Arg Leu Leu Asp Ala
1               5                   10                  15

Leu Gln Lys Lys Leu Lys
            20

<210> SEQ ID NO 146
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 146

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 147
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro Val Leu Glu Leu Phe Glu Asn Leu Leu Glu Arg Leu Phe Asp Ala
1               5                   10                  15

Leu Gln Lys Lys Leu Lys
            20

<210> SEQ ID NO 148
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Pro Val Leu Glu Leu Phe Glu Asn Leu Leu Glu Arg Leu Gly Asp Ala
1               5                   10                  15

Leu Gln Lys Lys Leu Lys
            20

<210> SEQ ID NO 149
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Pro Val Leu Glu Leu Phe Glu Asn Leu Trp Glu Arg Leu Leu Asp Ala
1               5                   10                  15

Leu Gln Lys Lys Leu Lys
            20

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Leu Leu Glu Leu Phe Glu Asn Leu Leu Glu Arg Leu Leu Asp Ala
1               5                   10                  15

Leu Gln Lys Lys Leu Lys
```

-continued

```
            20

<210> SEQ ID NO 151
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Pro Val Leu Glu Leu Phe Glu Asn Leu Gly Glu Arg Leu Leu Asp Ala
1               5                   10                  15

Leu Gln Lys Lys Leu Lys
            20

<210> SEQ ID NO 152
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Val Phe Glu Leu Phe Glu Asn Leu Leu Glu Arg Leu Leu Asp Ala
1               5                   10                  15

Leu Gln Lys Lys Leu Lys
            20

<210> SEQ ID NO 153
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Val Leu Glu Leu Phe Glu Asn Leu Leu Glu Arg Leu Leu Asp Ala
1               5                   10                  15

Leu Gln Lys Lys Leu Lys
            20

<210> SEQ ID NO 154
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Val Leu Glu Leu Phe Glu Asn Leu Leu Glu Arg Gly Leu Asp Ala
1               5                   10                  15

Leu Gln Lys Lys Leu Lys
            20

<210> SEQ ID NO 155
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 155

Pro Val Leu Glu Leu Phe Leu Asn Leu Trp Glu Arg Leu Leu Asp Ala
1               5                   10                  15

Leu Gln Lys Lys Leu Lys
            20

<210> SEQ ID NO 156
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Val Leu Glu Leu Phe Leu Asn Leu Leu Glu Arg Leu Leu Asp Ala
1               5                   10                  15

Leu Gln Lys Lys Leu Lys
            20

<210> SEQ ID NO 157
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Pro Val Leu Glu Phe Phe Glu Asn Leu Leu Glu Arg Leu Leu Asp Ala
1               5                   10                  15

Leu Gln Lys Lys Leu Lys
            20

<210> SEQ ID NO 158
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Pro Val Leu Glu Leu Phe Leu Asn Leu Leu Glu Arg Leu Leu Asp Trp
1               5                   10                  15

Leu Gln Lys Lys Leu Lys
            20

<210> SEQ ID NO 159
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Val Leu Asp Leu Phe Glu Asn Leu Leu Glu Arg Leu Leu Asp Ala
1               5                   10                  15

Leu Gln Lys Lys Leu Lys
            20

<210> SEQ ID NO 160
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Pro Val Leu Glu Leu Phe Glu Asn Leu Leu Glu Arg Leu Leu Asp Trp
1               5                   10                  15

Leu Gln Lys Lys Leu Lys
            20

<210> SEQ ID NO 161
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Pro Val Leu Glu Leu Phe Glu Asn Leu Leu Glu Arg Leu Leu Glu Ala
1               5                   10                  15

Leu Gln Lys Lys Leu Lys
            20

<210> SEQ ID NO 162
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Val Leu Glu Leu Phe Glu Asn Trp Leu Glu Arg Leu Leu Asp Ala
1               5                   10                  15

Leu Gln Lys Lys Leu Lys
            20

<210> SEQ ID NO 163
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Pro Val Leu Glu Leu Phe Glu Asn Leu Leu Glu Arg Leu Trp Asp Ala
1               5                   10                  15

Leu Gln Lys Lys Leu Lys
            20

<210> SEQ ID NO 164
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Pro Val Leu Glu Leu Phe Glu Asn Leu Leu Glu Arg Leu Leu Asp Ala
1               5                   10                  15
```

-continued

Trp Gln Lys Lys Leu Lys
            20

<210> SEQ ID NO 165
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Val Leu Glu Leu Phe Glu Asn Leu Leu Glu Arg Leu Leu Asp Leu
1               5                   10                  15

Leu Gln Lys Lys Leu Lys
            20

<210> SEQ ID NO 166
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Val Leu Glu Leu Phe Leu Asn Leu Leu Glu Lys Leu Leu Asp Ala
1               5                   10                  15

Leu Gln Lys Lys Leu Lys
            20

<210> SEQ ID NO 167
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Pro Val Leu Glu Leu Phe Glu Asn Gly Leu Glu Arg Leu Leu Asp Ala
1               5                   10                  15

Leu Gln Lys Lys Leu Lys
            20

<210> SEQ ID NO 168
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Val Leu Glu Leu Phe Glu Gln Leu Leu Glu Lys Leu Leu Asp Ala
1               5                   10                  15

Leu Gln Lys Lys Leu Lys
            20

<210> SEQ ID NO 169
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 169

Pro Val Leu Glu Leu Phe Glu Asn Leu Leu Glu Lys Leu Leu Asp Ala
1               5                   10                  15

Leu Gln Lys Lys Leu Lys
            20

<210> SEQ ID NO 170
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ornithine
<220> FEATURE:
<221> NAME/KEY: MOD_RES
<222> LOCATION: (19)..(20)
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 170

Pro Val Leu Glu Leu Phe Glu Asn Leu Leu Glu Xaa Leu Leu Asp Ala
1               5                   10                  15

Leu Gln Xaa Xaa Leu Xaa
            20

<210> SEQ ID NO 171
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Val Leu Glu Leu Phe Glu Asn Leu Leu Glu Lys Leu Leu Asp Leu
1               5                   10                  15

Leu Gln Lys Lys Leu Lys
            20

<210> SEQ ID NO 172
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Pro Val Leu Glu Leu Phe Leu Asn Leu Leu Glu Arg Leu Gly Asp Ala
1               5                   10                  15

Leu Gln Lys Lys Leu Lys
            20

<210> SEQ ID NO 173
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Pro Val Leu Asp Leu Phe Asp Asn Leu Leu Asp Arg Leu Leu Asp Leu
1               5                   10                  15

Leu Asn Lys Lys Leu Lys
            20

<210> SEQ ID NO 174
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: D-Glu
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (7)..(7)
<223> OTHER INFORMATION: D-Glu
<220> FEATURE:
<221> NAME/KEY: MOD_RES
<222> LOCATION: (8)..(8)
<223> OTHER INFORMATION: D-Asn
<220> FEATURE:
<221> NAME/KEY: MOD_RES
<222> LOCATION: (9)..(10)
<223> OTHER INFORMATION: D-Leu
<220> FEATURE:
<221> NAME/KEY: MOD_RES
<222> LOCATION: (11)..(11)
<223> OTHER INFORMATION: D-Glu
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(14)
<223> OTHER INFORMATION: D-Leu
<220> FEATURE:
<221> NAME/KEY: MOD_RES
<222> LOCATION: (15)..(15)
<223> OTHER INFORMATION: D-Asp
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Leu
<220> FEATURE:

```
<221> NAME/KEY: MOD_RES
<222> LOCATION: (18)..(18)
<223> OTHER INFORMATION: D-Gln
<220> FEATURE:
<221> NAME/KEY: MOD_RES
<222> LOCATION: (19)..(20)
<223> OTHER INFORMATION: D-Lys
<220> FEATURE:
<221> NAME/KEY: MOD_RES
<222> LOCATION: (21)..(21)
<223> OTHER INFORMATION: D-Leu
<220> FEATURE:
<221> NAME/KEY: MOD_RES
<222> LOCATION: (22)..(22)
<223> OTHER INFORMATION: D-Lys

<400> SEQUENCE: 174

Pro Val Leu Glu Leu Phe Glu Asn Leu Leu Glu Arg Leu Leu Asp Ala
1               5                   10                  15
Leu Gln Lys Lys Leu Lys
            20

<210> SEQ ID NO 175
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Pro Val Leu Glu Leu Phe Glu Asn Leu Leu Glu Arg Leu Leu Glu Leu
1               5                   10                  15
Leu Asn Lys Lys Leu Lys
            20

<210> SEQ ID NO 176
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Pro Val Leu Glu Leu Trp Glu Asn Leu Leu Glu Arg Leu Leu Asp Ala
1               5                   10                  15
Leu Gln Lys Lys Leu Lys
            20

<210> SEQ ID NO 177
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Val Leu Glu Leu Phe Leu Asn Leu Leu Glu Arg Leu Leu Asp Ala
1               5                   10                  15
Leu Gln Lys Lys Leu Lys
            20

<210> SEQ ID NO 178
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 178

Pro Val Leu Glu Leu Phe Asp Asn Leu Leu Glu Lys Leu Leu Glu Ala
1               5                   10                  15

Leu Gln Lys Lys Leu Arg
            20

<210> SEQ ID NO 179
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Pro Val Leu Glu Leu Phe Asp Asn Leu Leu Glu Arg Leu Leu Asp Ala
1               5                   10                  15

Leu Gln Lys Lys Leu Lys
            20

<210> SEQ ID NO 180
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Pro Val Leu Glu Leu Phe Asp Asn Leu Leu Asp Lys Leu Leu Asp Ala
1               5                   10                  15

Leu Gln Lys Lys Leu Arg
            20

<210> SEQ ID NO 181
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Pro Val Leu Glu Leu Phe Glu Asn Leu Leu Glu Arg Trp Leu Asp Ala
1               5                   10                  15

Leu Gln Lys Lys Leu Lys
            20

<210> SEQ ID NO 182
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Pro Val Leu Glu Leu Phe Glu Asn Leu Leu Glu Lys Leu Leu Glu Ala
1               5                   10                  15

Leu Gln Lys Lys Leu Lys
```

```
<210> SEQ ID NO 183
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Pro Leu Leu Glu Leu Phe Glu Asn Leu Leu Glu Lys Leu Leu Asp Ala
1               5                   10                  15

Leu Gln Lys Lys Leu Lys
            20

<210> SEQ ID NO 184
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Pro Val Leu Glu Leu Phe Leu Asn Leu Leu Glu Arg Leu Leu Asp Ala
1               5                   10                  15

Trp Gln Lys Lys Leu Lys
            20

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(20)
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 185

Pro Val Leu Glu Leu Phe Glu Asn Leu Leu Glu Arg Leu Leu Asp Ala
1               5                   10                  15

Leu Gln Xaa Xaa Leu Xaa
            20

<210> SEQ ID NO 186
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Pro Val Leu Glu Leu Phe Glu Gln Leu Leu Glu Arg Leu Leu Asp Ala
1               5                   10                  15

Leu Gln Lys Lys Leu Lys
            20
```

```
<210> SEQ ID NO 187
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Pro Val Leu Glu Leu Phe Glu Asn Leu Leu Glu Arg Leu Leu Asp Ala
1               5                   10                  15

Leu Asn Lys Lys Leu Lys
            20

<210> SEQ ID NO 188
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Pro Val Leu Glu Leu Phe Glu Asn Leu Leu Asp Arg Leu Leu Asp Ala
1               5                   10                  15

Leu Gln Lys Lys Leu Lys
            20

<210> SEQ ID NO 189
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Val Leu Glu Leu Phe Glu Asn Leu Leu Glu Arg Leu Leu Asp Ala
1               5                   10                  15

Leu Gln Lys Lys Leu Lys
            20

<210> SEQ ID NO 190
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Pro Val Leu Glu Phe Trp Asp Asn Leu Leu Asp Lys Leu Leu Asp Ala
1               5                   10                  15

Leu Gln Lys Lys Leu Arg
            20

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Pro Val Leu Asp Leu Leu Arg Glu Leu Leu Glu Glu Leu Lys Gln Lys
```

-continued

```
                1               5                  10                 15
Leu Lys

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Pro Val Leu Asp Leu Phe Lys Glu Leu Leu Glu Glu Leu Lys Gln Lys
1               5                  10                 15

Leu Lys

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Pro Val Leu Asp Leu Phe Arg Glu Leu Leu Glu Glu Leu Lys Gln Lys
1               5                  10                 15

Leu Lys

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Pro Val Leu Glu Leu Phe Arg Glu Leu Leu Glu Glu Leu Lys Gln Lys
1               5                  10                 15

Leu Lys

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Pro Val Leu Glu Leu Phe Lys Glu Leu Leu Glu Glu Leu Lys Gln Lys
1               5                  10                 15

Leu Lys

<210> SEQ ID NO 196
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196
```

-continued

```
Pro Val Leu Asp Leu Phe Arg Glu Leu Leu Glu Glu Leu Lys Asn Lys
1               5                   10                  15

Leu Lys

<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Pro Leu Leu Asp Leu Phe Arg Glu Leu Leu Glu Glu Leu Lys Gln Lys
1               5                   10                  15

Leu Lys

<210> SEQ ID NO 198
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Val Leu Asp Leu Phe Arg Glu Leu Leu Glu Glu Leu Lys Gln Lys
1               5                   10                  15

Leu Lys

<210> SEQ ID NO 199
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Pro Val Leu Asp Leu Phe Arg Glu Leu Trp Glu Glu Leu Lys Gln Lys
1               5                   10                  15

Leu Lys

<210> SEQ ID NO 200
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asn Val Leu Asp Leu Phe Arg Glu Leu Leu Glu Glu Leu Lys Gln Lys
1               5                   10                  15

Leu Lys

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201
```

```
Pro Leu Leu Asp Leu Phe Lys Glu Leu Leu Glu Glu Leu Lys Gln Lys
1               5                   10                  15

Leu Lys

<210> SEQ ID NO 202
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Pro Ala Leu Glu Leu Phe Lys Asp Leu Leu Glu Glu Leu Arg Gln Lys
1               5                   10                  15

Leu Arg

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Val Leu Asp Leu Phe Arg Glu Leu Leu Glu Glu Leu Lys Gln Lys
1               5                   10                  15

Leu Lys

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Val Leu Asp Phe Phe Arg Glu Leu Leu Glu Glu Leu Lys Gln Lys
1               5                   10                  15

Leu Lys

<210> SEQ ID NO 205
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Pro Val Leu Asp Leu Phe Arg Glu Trp Leu Glu Glu Leu Lys Gln Lys
1               5                   10                  15

Leu Lys

<210> SEQ ID NO 206
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 206

Pro Leu Leu Glu Leu Leu Lys Glu Leu Leu Glu Glu Leu Lys Gln Lys
1               5                   10                  15

Leu Lys

<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Pro Val Leu Glu Leu Leu Lys Glu Leu Leu Glu Glu Leu Lys Gln Lys
1               5                   10                  15

Leu Lys

<210> SEQ ID NO 208
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Pro Ala Leu Glu Leu Phe Lys Asp Leu Leu Glu Glu Leu Arg Gln Arg
1               5                   10                  15

Leu Lys

<210> SEQ ID NO 209
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Pro Val Leu Asp Leu Phe Arg Glu Leu Leu Asn Glu Leu Leu Gln Lys
1               5                   10                  15

Leu Lys

<210> SEQ ID NO 210
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Val Leu Asp Leu Phe Arg Glu Leu Leu Glu Glu Leu Lys Gln Lys
1               5                   10                  15

Leu Lys

<210> SEQ ID NO 211
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (14)..(14)
<223> OTHER INFORMATION: Ornithine
<220> FEATURE:
<221> NAME/KEY: MOD_RES
<222> LOCATION: (16)..(16)
<223> OTHER INFORMATION: Ornithine
<220> FEATURE:
<221> NAME/KEY: MOD_RES
<222> LOCATION: (18)..(18)
<223> OTHER INFORMATION: Ornithine

<400> SEQUENCE: 211

Pro Val Leu Asp Leu Phe Arg Glu Leu Leu Glu Glu Leu Xaa Gln Xaa
1               5                   10                  15

Leu Xaa

<210> SEQ ID NO 212
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ornithine
<220> FEATURE:
<221> NAME/KEY: MOD_RES
<222> LOCATION: (14)..(14)
<223> OTHER INFORMATION: Ornithine
<220> FEATURE:
<221> NAME/KEY: MOD_RES
<222> LOCATION: (16)..(16)
<223> OTHER INFORMATION: Ornithine

<400> SEQUENCE: 212

Pro Val Leu Asp Leu Phe Xaa Glu Leu Leu Glu Glu Leu Xaa Gln Xaa
1               5                   10                  15

Leu Lys

<210> SEQ ID NO 213
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Pro Ala Leu Glu Leu Phe Lys Asp Leu Leu Glu Glu Phe Arg Gln Arg
1               5                   10                  15

Leu Lys

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pro

<400> SEQUENCE: 214
```

```
Pro Val Leu Asp Leu Phe Arg Glu Leu Leu Glu Glu Leu Lys Gln Lys
1               5                   10                  15

Leu Lys

<210> SEQ ID NO 215
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Pro Val Leu Asp Leu Phe Arg Glu Leu Leu Glu Glu Trp Lys Gln Lys
1               5                   10                  15

Leu Lys

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Pro Val Leu Glu Leu Phe Lys Glu Leu Leu Glu Glu Leu Lys Gln Lys
1               5                   10                  15

Leu Lys

<210> SEQ ID NO 217
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Pro Val Leu Asp Leu Phe Arg Glu Leu Leu Glu Leu Leu Lys Gln Lys
1               5                   10                  15

Leu Lys

<210> SEQ ID NO 218
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Pro Val Leu Asp Leu Phe Arg Glu Leu Leu Asn Glu Leu Leu Gln Lys
1               5                   10                  15

Leu Lys

<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219
```

Pro Val Leu Asp Leu Phe Arg Glu Leu Leu Asn Glu Leu Trp Gln Lys
1               5                   10                  15

Leu Lys

<210> SEQ ID NO 220
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Pro Val Leu Asp Leu Phe Arg Glu Leu Leu Glu Glu Leu Gln Lys Lys
1               5                   10                  15

Leu Lys

<210> SEQ ID NO 221
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asp Val Leu Asp Leu Phe Arg Glu Leu Leu Glu Glu Leu Lys Gln Lys
1               5                   10                  15

Leu Lys

<210> SEQ ID NO 222
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Pro Val Leu Asp Ala Phe Arg Glu Leu Leu Glu Ala Leu Leu Gln Leu
1               5                   10                  15

Lys Lys

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Pro Val Leu Asp Ala Phe Arg Glu Leu Leu Glu Ala Leu Ala Gln Leu
1               5                   10                  15

Lys Lys

<210> SEQ ID NO 224
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 224

Pro Val Leu Asp Leu Phe Arg Glu Gly Trp Glu Glu Leu Lys Gln Lys
1               5                   10                  15

Leu Lys

<210> SEQ ID NO 225
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Pro Val Leu Asp Ala Phe Arg Glu Leu Ala Glu Ala Leu Ala Gln Leu
1               5                   10                  15

Lys Lys

<210> SEQ ID NO 226
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Pro Val Leu Asp Ala Phe Arg Glu Leu Gly Glu Ala Leu Leu Gln Leu
1               5                   10                  15

Lys Lys

<210> SEQ ID NO 227
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Pro Val Leu Asp Leu Phe Arg Glu Leu Gly Glu Glu Leu Lys Gln Lys
1               5                   10                  15

Leu Lys

<210> SEQ ID NO 228
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Pro Val Leu Asp Leu Phe Arg Glu Gly Leu Glu Glu Leu Lys Gln Lys
1               5                   10                  15

Leu Lys

<210> SEQ ID NO 229
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 229

Pro Val Leu Asp Leu Phe Arg Glu Leu Leu Glu Gly Lys Gln Lys
1               5                   10                  15
Leu Lys

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Pro Val Leu Glu Leu Phe Glu Arg Leu Leu Glu Asp Leu Gln Lys Lys
1               5                   10                  15
Leu Lys

<210> SEQ ID NO 231
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Pro Val Leu Asp Leu Phe Arg Glu Leu Leu Glu Lys Leu Glu Gln Lys
1               5                   10                  15
Leu Lys

<210> SEQ ID NO 232
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Pro Leu Leu Glu Leu Phe Lys Glu Leu Leu Glu Glu Leu Lys Gln Lys
1               5                   10                  15
Leu Lys

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236
```

```
<400> SEQUENCE: 236

000

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Asp Asp Leu Leu Gln Lys Trp Ala Glu Ala Phe Asn Gln Leu Leu
1               5                   10                  15

Lys Lys

<210> SEQ ID NO 238
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Trp Leu Lys Ala Phe Tyr Glu Lys Val Leu Glu Lys Leu Lys Glu
1               5                   10                  15

Leu Phe

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Glu Trp Leu Glu Ala Phe Tyr Lys Lys Val Leu Glu Lys Leu Lys Glu
1               5                   10                  15

Leu Phe

<210> SEQ ID NO 240
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Trp Leu Lys Ala Phe Tyr Asp Lys Val Ala Glu Lys Leu Lys Glu
1               5                   10                  15

Ala Phe

<210> SEQ ID NO 241
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241
```

Asp Trp Phe Lys Ala Phe Tyr Asp Lys Val Phe Glu Lys Phe Lys Glu
1               5                   10                  15

Phe Phe

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Ile Lys Lys Phe Leu Gly Ser Ile Trp Lys Phe Ile Lys Ala Phe
1               5                   10                  15

Val Gly

<210> SEQ ID NO 243
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Trp Phe Lys Ala Phe Tyr Asp Lys Val Ala Glu Lys Phe Lys Glu
1               5                   10                  15

Ala Phe

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Trp Leu Lys Ala Phe Tyr Asp Lys Val Ala Glu Lys Leu Lys Glu
1               5                   10                  15

Ala Phe

<210> SEQ ID NO 245
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Trp Leu Lys Ala Phe Tyr Asp Lys Val Phe Glu Lys Phe Lys Glu
1               5                   10                  15

Phe Phe

<210> SEQ ID NO 246
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 246

Glu Trp Leu Glu Ala Phe Tyr Lys Lys Val Leu Glu Lys Leu Lys Glu
1               5                   10                  15

Leu Phe

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Trp Phe Lys Ala Phe Tyr Asp Lys Phe Phe Glu Lys Phe Lys Glu
1               5                   10                  15

Phe Phe

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Trp Leu Lys Ala Phe Tyr Glu Lys Val Leu Glu Lys Leu Lys Glu
1               5                   10                  15

Leu Phe

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Glu Trp Leu Lys Ala Glu Tyr Glu Lys Val Glu Glu Lys Leu Lys Glu
1               5                   10                  15

Leu Phe

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Trp Leu Lys Ala Glu Tyr Glu Lys Val Leu Glu Lys Leu Lys Glu
1               5                   10                  15

Leu Phe

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 251

Glu Trp Leu Lys Ala Phe Tyr Lys Lys Val Leu Glu Lys Leu Lys Glu
1               5                   10                  15

Leu Phe

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Pro Val Leu Asp Leu Phe Arg Glu Leu Leu Glu Gln Lys Leu Lys
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Pro Val Leu Asp Leu Phe Arg Glu Leu Leu Glu Glu Leu Lys Gln Lys
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Pro Val Leu Asp Leu Phe Arg Glu Leu Leu Glu Lys Leu Lys Gln Lys
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Pro Val Leu Asp Leu Phe Arg Glu Leu Leu Glu Lys Leu Gln Lys
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Pro Val Leu Asp Leu Phe Arg Glu Leu Leu Glu Ala Leu Lys Gln Lys
1               5                   10                  15
```

```
<210> SEQ ID NO 257
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Pro Val Leu Asp Leu Phe Glu Asn Leu Leu Glu Arg Leu Lys Gln Lys
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Pro Val Leu Asp Leu Phe Arg Glu Leu Leu Asn Glu Leu Lys Gln Lys
1               5                   10                  15
```